(12) United States Patent
Price

(10) Patent No.: US 7,756,305 B2
(45) Date of Patent: Jul. 13, 2010

(54) FAST 3D CYTOMETRY FOR INFORMATION IN TISSUE ENGINEERING

(75) Inventor: Jeffrey H. Price, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 1773 days.

(21) Appl. No.: 10/351,455

(22) Filed: Jan. 23, 2003

(65) Prior Publication Data

US 2003/0184730 A1 Oct. 2, 2003

Related U.S. Application Data

(60) Provisional application No. 60/351,855, filed on Jan. 23, 2002.

(51) Int. Cl.
  *G06K 9/00* (2006.01)
(52) U.S. Cl. .................................. 382/128; 128/922
(58) Field of Classification Search ......... 382/128–132, 382/100; 128/922; 378/4–27
  See application file for complete search history.

(56) References Cited

U.S. PATENT DOCUMENTS

| | | | |
|---|---|---|---|
| 5,548,661 A | 8/1996 | Price et al. | |
| 5,587,832 A | 12/1996 | Krause | |
| 5,760,950 A * | 6/1998 | Maly et al. | 359/368 |
| 5,790,692 A * | 8/1998 | Price et al. | 382/133 |
| 5,790,710 A | 8/1998 | Price et al. | |
| 5,923,466 A | 7/1999 | Krause et al. | |
| 5,995,143 A | 11/1999 | Price et al. | |
| 6,215,841 B1 * | 4/2001 | Hsieh | 378/8 |
| 7,050,620 B2 * | 5/2006 | Heckman | 382/133 |
| 7,072,515 B2 * | 7/2006 | Al-Kofahi et al. | 382/199 |
| 7,155,042 B1 * | 12/2006 | Cowan et al. | 382/128 |
| 2001/0033299 A1 | 10/2001 | Callaway et al. | |
| 2002/0001089 A1 * | 1/2002 | Price | 356/601 |
| 2002/0044346 A1 | 4/2002 | Nguyen et al. | |
| 2002/0186874 A1 | 12/2002 | Price et al. | |
| 2003/0059093 A1 * | 3/2003 | Rosania et al. | 382/128 |
| 2004/0071363 A1 * | 4/2004 | Kouri et al. | 382/276 |

FOREIGN PATENT DOCUMENTS

WO  WO 01/54061 A2  7/2001

* cited by examiner

Primary Examiner—Anand Bhatnagar
(74) Attorney, Agent, or Firm—John P. O'Banion

(57) ABSTRACT

Methods and apparatus are described for enhancing operator independent image cytometry. Aspects of the invention include enhanced tissue surface tracking which can detect both tissue surfaces. The surface detection can aid cytometry, such as by reducing the amount of image data to be stored. Segmentation is described for 3D images in which 3D least squares filtering is applied to increase contrast for simplifying the delineation of objects from backgrounds. A method of creating 3D FIR image filters based on ideal objects is also described. A data structure is defined by which 3D object data may be organized for image representations if samples. Methods of performing remote segmentation processing are also described toward centralizing the necessary processor power and applications and reducing the burden on researchers and clinicians.

9 Claims, 29 Drawing Sheets

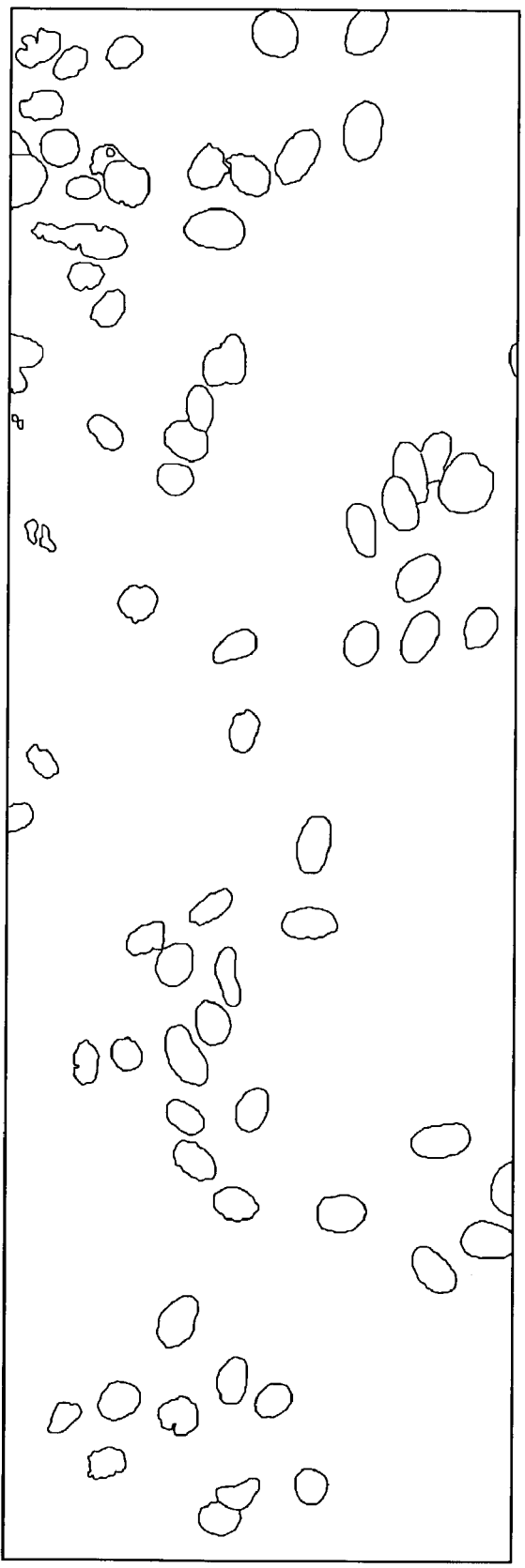
FIG. 3A  FIG. 3B

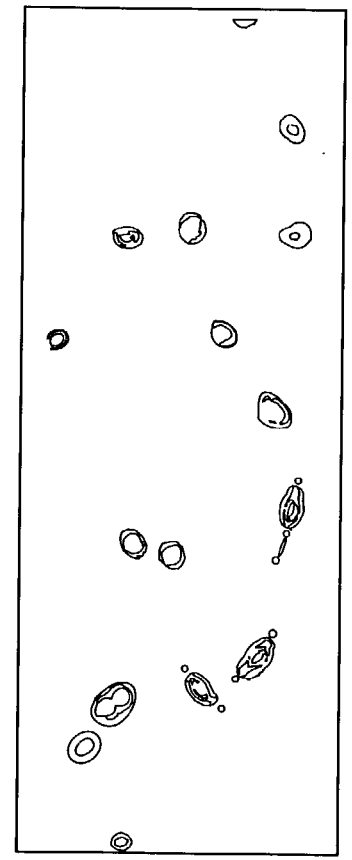
FIG. 9A
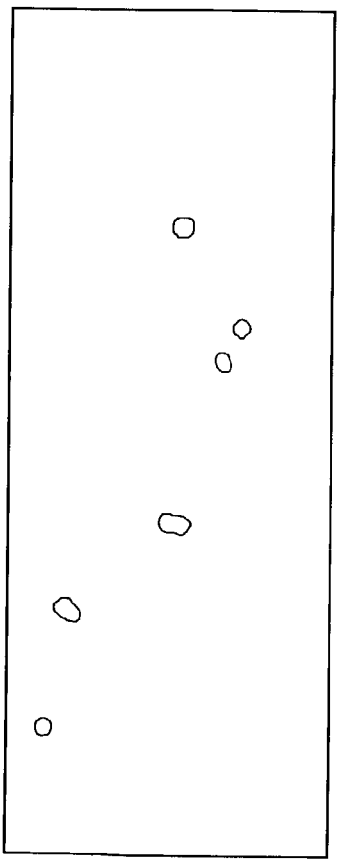
FIG. 9B
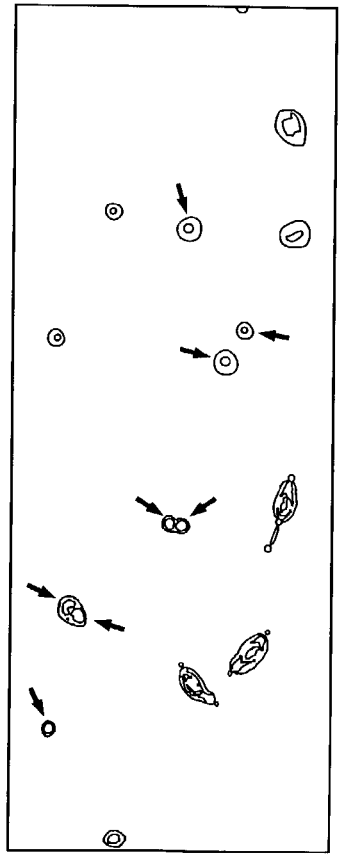
FIG. 8A
FIG. 8B

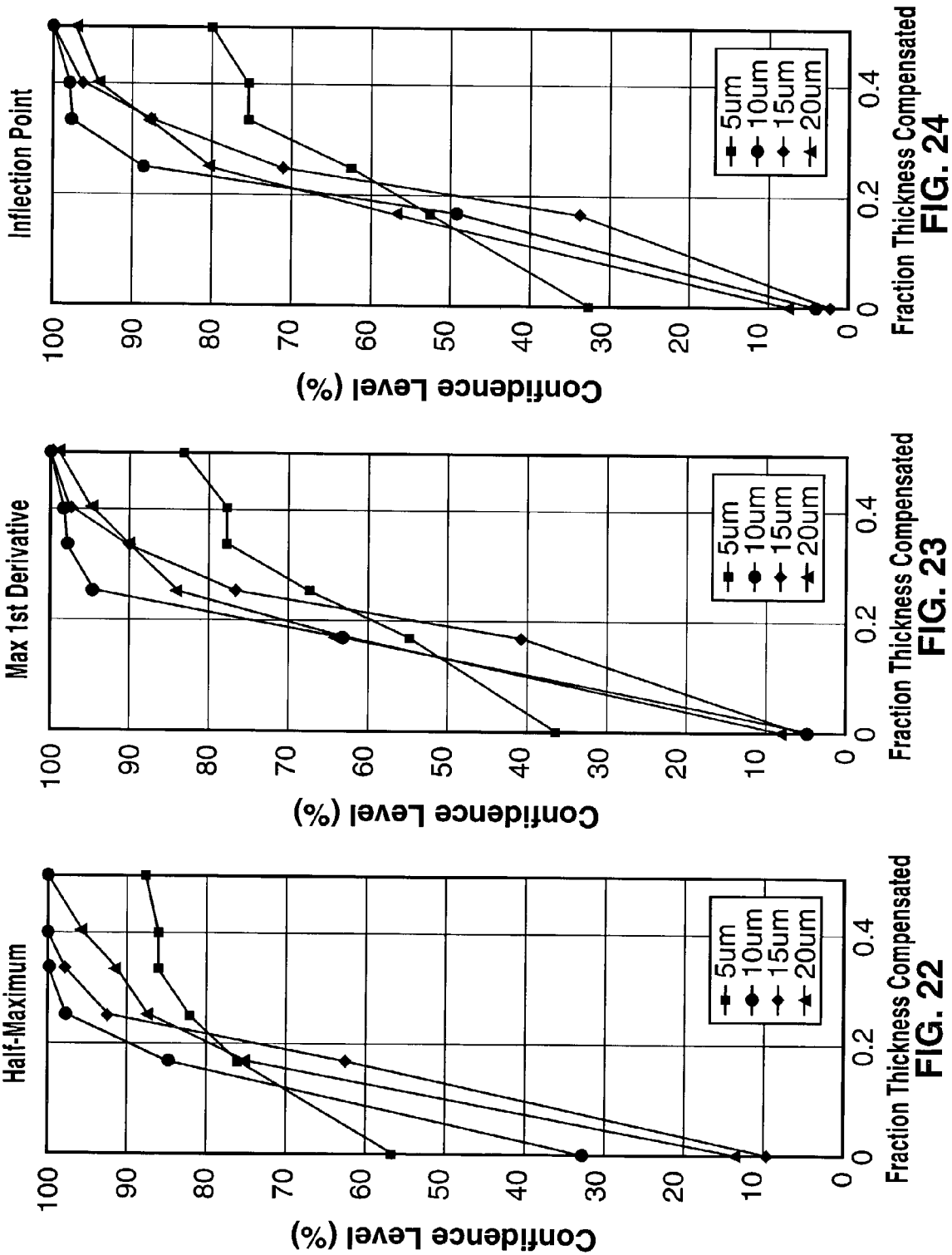

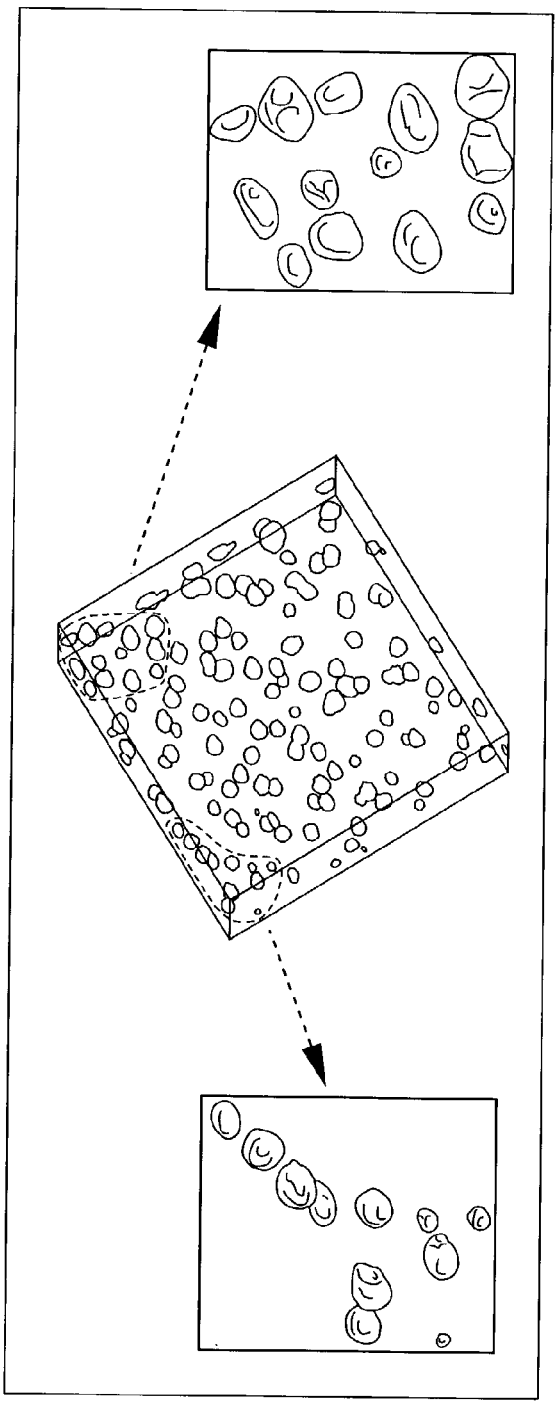 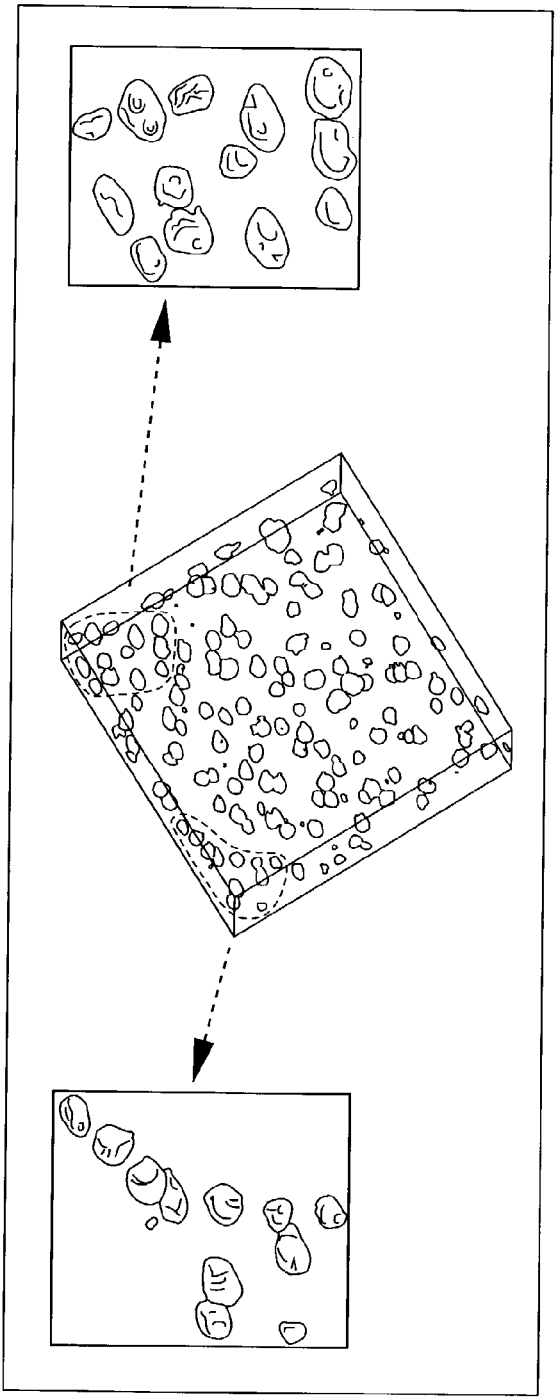
FIG. 32A  FIG. 32B

FAST 3D CYTOMETRY FOR INFORMATION IN TISSUE ENGINEERING

CROSS-REFERENCE TO RELATED APPLICATIONS

This application claims priority from U.S. provisional application Ser. No. 60/351,855 filed on Jan. 23, 2002, incorporated herein by reference.

STATEMENT REGARDING FEDERALLY SPONSORED RESEARCH OR DEVELOPMENT

This invention was made with Government support under Grant No. BES-9871365, awarded by the National Science Foundation. The Government has certain rights in this invention.

INCORPORATION-BY-REFERENCE OF MATERIAL SUBMITTED ON A COMPACT DISC

Not Applicable

BACKGROUND OF THE INVENTION

1. Field of the Invention

This invention pertains generally to the field of cytometry and more particularly to cytometry systems and methods that provide real time three dimensional image enhancement, such as segmentation, contrast, and edge sharpening in response to images gathered by high-speed confocal microscopy that may be based on surface tracking.

2. Description of Related Art

Recent microscopic techniques and systems have provided practical cytographic imaging and segmentation in two dimensions. The fully automated scanning of cells using these microscopic techniques, such as performed on an operator independent cytometer, has been found to yield important diagnostic and research information for a number of biomedical applications, in particular those involving tissue research. For example, in the case of fluorescent cytology the use of digital light processing techniques with a cytometer can yield images of cell nuclei stained with a fluorescent dye which can be analyzed to extract relevant information, such as quantities of DNA, nuclear sizes, shapes and positions.

In addition, the ability to segment objects from the background and from image artifacts has shown itself to be an important capability when studying tissues. As utilized herein the term "segmentation" refers to partitioning an image into parts ("segments") that may be individually processed. In the context of tissue research the segments of interest, which may also be referred to as "objects", are typically individual cells. The use of segmentation reduces the vagaries and overhead associated with human interpretations while increasing the speed, efficiency, and repeatability with which results are produced.

Once segmented, the binary image may be analyzed for size and shape information and overlaid on the original image to produce integrated intensity and pattern information. In many applications it is advantageous to process a large number of cells (i.e. $10^4$ to $10^6$ cells), because of the inherent biologic variability. By way of example, performing an analysis spanning a large numbers of cells is particularly important in PAP smear screening, (and tests having a similarly large sample size) in which all cells on the slide may be measured to provide an accurate analysis that is not subject to false negative diagnoses. It should be appreciated that at this level of detail analytical intervention by a human operator is generally impractical. Accurate analysis in this and other situations involving a large number of objects requires the use of operator independent automation for the thousands of images collected for each slide.

Scanning two-dimensional cytometry has therefore become a successful commercial tool for tissue engineering. Representative of these systems are the teachings found in U.S. Pat. Nos. 5,995,143; 5,790,710; 5,790,692; and 5,548,661; and publication US2002/0186874 along with US International publication WO 01/54061 which are included herein by reference. Two-dimensional cytometry techniques typically utilize a form of confocal microscopy utilizing a micromirror array, such as taught within U.S. Pat. Nos. 5,587,832 and 5,923,466 whose teachings are also included herein by reference. A multiparallel three dimensional optical microscopy system is described by J. Price in publication number US2002/0001089 which is included herein by reference.

However, it should be appreciated that relying on two-dimensional images of natively three-dimensional (3D) structures can lead to errors and mis-estimations. Obtaining 3D images, however, is generally impractical for most applications as the current methods are slow and subject to various errors.

FIG. 1 represents a conventional 3D confocal scanning technique in which vertical stacks of optical sections are collected by changing focus on the microscope. After collection of the Z-scan (images collected along the Z-direction), lateral stage motion (X and Y) is performed to move from capturing one Z-direction stack to the next. The length of time required for performing this step and repeat process on a sample is generally prohibitive for most applications. The resultant set of collected data forms an XYZ image montage from which an extended 3D image may be rendered. In a typical confocal microscope used for collecting 3D images, the user interactively sets the top and bottom limits of the Z-scan and a computer-controlled system collects optical sections using a predetermined focus increment.

Current method and system for collecting 3D images are impractically slow for most tissue study applications. Confocal microscopes are currently too slow while three-dimensional (3D) imaging tools lack the accuracy and features required for scientists and tissue engineers to analyze from millions to billions of cells in tissue volumes It should be appreciated, for example, that blood has approximately five billion cells per milliliter (5 B cells/ml).

Therefore, a need exists for a 3D imaging that allows rapid autonomous imaging while still providing image segmentation as outlined above for tissue research and clinical applications. The present invention satisfies those needs, as well as others, and overcomes the deficiencies of previously developed 3D imaging solutions.

BRIEF SUMMARY OF THE INVENTION

The present invention provides a system and method of performing three-dimensional image segmentation, which may be performed in real time, along with a system and method for controlling autofocus based on surface tracking within a confocal imaging scan. The present invention thereby provides a system and method for performing fast 3D cytometry to gather information on 3D structures. The invention is particularly well suited for use in tissue engineering, wherein the imaging objects are cellular structures.

The applications for the present system span the whole spectrum of biological hierarchy, ranging from molecular biology to whole organ level studies. One aspect of the invention is a method of controlling the autofocusing of a microscope having a focus mechanism, comprising (a) establishing an initial focal range for volume scanning of a sample by a microscope; (b) detecting a surface of the sample in response to registered optical characteristics; and (c) mapping of images from a set of optical planes in response to the location of the surface of the sample. An apparatus comprising a computer element and programming for executing the above steps can be created according to the present invention, or the method may be incorporated within other systems or hardware. It should be recognized that that registering the optical characteristics may be in response to optical energy that is reflected from, transmitted through, or the fluorescence from, the sample. The sample preferably comprises a cellular tissue sample and the surfaces being detected are either an upper or lower surface of the sample. The reflected optical characteristics being registered comprise the optical power of high spatial frequency components.

The surface detection can provide for limiting the collection of image data to objects within a cellular tissue sample imaged with microscope, comprising: (a) establishing an initial focal range for volume scanning of a sample by a microscope; (b) detecting a surface of said sample in response to registered optical characteristics; and (c) selecting images for storage that lie within said cellular tissue sample as determined in response to the positional relationship of the positions of said images with said detected surface. An apparatus comprising a computer element and programming for executing the above steps can be created according to the present invention, or the method may be incorporated within other systems or hardware.

Another aspect of the present invention is a method of performing image segmentation in which 3D objects are distinguished from a background, comprising (a) recording a 3D image of a sample volume; (b) enhancing object to background contrast ratios for said 3D image; thresholding said 3D image to delineate object boundaries; and generating information about the 3D objects based on the object boundaries. An apparatus comprising a computer element and programming for executing the above steps can be created according to the present invention, or the method may be incorporated within other systems or hardware. Information about the 3D objects may comprise image renderings, image enhancement, quantitative information, and any other desired information which may be collected in reference to three dimensional image representations.

Thresholding is performed in response to analyzing confocal volumes within said 3D images and is preferably performed by selecting a minimum after the largest background intensity peak, such as a the first minimum. Filters are preferably created based on an ideal object, a 4 µm fluorescent bead being utilized by way of example, for which least squares FIR filters are created.

A method of remotely performing image segmentation for samples is described comprising: (a) establishing communication with a remote server configured for receiving cytometry image data sets; (b) establishing a designated recipient for segmentation information; (c) transmitting an image data set to the remote server; (d) receiving the image data set by the server; (e) generating segmentation output data in response to segmenting of the image data set; and (f) transmitting segmentation output data to the designated recipient. An apparatus comprising a computer element and programming for executing the above steps can be created according to the present invention, or the method may be incorporated within other systems or hardware. In this way users having an image-collecting microscope, such as a 2D or 3D cytometer, need not have their own segmentation processing computers and application program and may send the image data sets off for remote processing.

Accordingly, there is a continuing need in the art for a device and/or method that can readily obtain and segment three dimensional tissue images. The present invention satisfies these needs, as well as others, and generally overcomes the deficiencies found in existing equipment and methods.

An aspect of the invention is to provide a 3D cytometry system capable of rapidly collecting necessary image data for 3D imaging of a tissue sample.

Another aspect of the invention is to provide a technique of focusing based on image sharpness as registered by the power of the high spatial frequency components.

Another aspect of the invention is to provide an autofocusing method capable of tracking the front surface of the tissue sample.

Another aspect of the invention is to provide an autofocusing method capable of tracking the rear surface of the tissue sample.

Another aspect of the invention is to provide an autofocusing method capable of tracking the center of the tissue sample.

Another aspect of the invention is provide tissue imaging in which stored imaging depth is performed in response to front, rear, or an intermediate tracking reference of the tissue.

Another aspect of the invention is to provide a 3D scanning cytometry system that can operate unattended.

Another aspect of the invention is to provide a 3D scanning cytometry system that can reassemble 3D fields of view collected by a scanning cytometer.

Another aspect of the invention is to provide a 3D scanning cytometry system that performs mechanized tracking of laterally undulating tissue sections.

Another aspect of the invention is to provide a 3D segmentation method capable of enhancing image definition.

Another aspect of the invention is provide a 3D segmentation capable of extracting feature information from collected 3D image data.

Another aspect of the invention is to provide a 3D segmentation method that enhances 3D object to background contrast.

Another aspect of the invention is to provide a 3D segmentation method that can provide automatic thresholding for discerning objects.

Another aspect of the invention is to provide a 3D segmentation method that provides a high detection accuracy.

Another aspect of the invention is to provide an infrastructure for identifying, storing, and retrieving 3D cell images.

Another aspect of the invention is to represent 3D image data as object on a background to eliminate the need to store background image data.

Another aspect of the invention is to store objects associated with 3D image data into a structure having a cell, slice, object hierarchy.

Another aspect of the invention is provide a system of 3D imaging that can perform image classification, such as by utilizing a neural network, or computational image processing techniques.

Another aspect of the invention is provide a 3D cytometer which can be utilized in combination with an ablation device to dispatch (kill) selected cells.

Another aspect of the invention is to provide a 3D cytometer which can be utilized in combination with a laser ablation device to dispatch (kill) selected cells.

Another aspect of the invention is to provide a 3D cytometer which can be utilized in combination with a micromanipulator for moving selected cells, such as a laser based micromanipulation device.

Another aspect of the invention is to provide a method of communicating cytometry image data sets to a remote location for segmentation and other image processing, after which information relating to the processed image data set is returned.

Another aspect of the invention is provide a method of communicating 3D cytometry image data sets to a remote location for segmentation and other image processing, after which information relating to the processed image data set is returned.

Another aspect of the invention is to provide an image segmentation method in which need not reconstruct details at high resolution, but that enhances the contrast of object edges.

Another aspect of the invention is to provide an image segmentation method in which thresholding is performed on 3D objects utilizing least squares filtering for discerning image objects.

Another aspect of the invention is to provide a method for creating 3D filters based on non-cellular "ideal" objects having a desired shape and size.

Another aspect of the invention is to provide a method for creating 3D filters based on fluorescent non-cellular "ideal" objects having a desired shape and size.

Another aspect of the invention is to provide a method for creating 3D filters based on fluorescent beads utilized as "ideal" objects.

Another aspect of the invention is provide a segmentation engine that is capable of being executed on single computers, multiprocessing computers, and banks of digital signal processors.

Another aspect of the invention is provide a method of 3D imaging in which 3D image objects are filtered utilizing a stacked series of 2D filters, such as finite impulse response (FIR) filters.

Another aspect of the invention is the utilization of automated methods of defining object boundaries.

A still further aspect of the invention is to utilize "full-width at half-maximum", maximum first derivative, and inflection detection to identify object boundaries.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 3A is an image representation a fluorescence image strip from a continuous image scan.

FIG. 3B is an image representation of a section of the fluorescence image strip shown near the arrow of FIG. 3A.

FIG. 8A is an image representation of a phase contrast image for cells prior to ablation according to an aspect of the present invention, showing arrows pointing to "contaminant" cells.

FIG. 8B is an image representation of a fluorescence image for cells prior to ablation according to an aspect of the present invention, showing model contaminant cells stained with fluorescent dye, such as CellTracker Blue.

FIG. 9A is an image representation of a phase contrast image for cells following ablation according to an aspect of the present invention, showing the dead cells appearing more opaque and being positionally displaced in response to ablation.

FIG. 9B is an image representation of a fluorescence image for cells following ablation according to an aspect of the present invention, showing the fluorescence of dead cells stained with fluorescent dye, such as PI.

FIG. 22 is a plot of confidence levels for a half-maximum detection method according to an aspect of the present invention in response to fractional thickness of the sample.

FIG. 23 is a plot of confidence levels for a maximum first derivative detection method according to an aspect of the present invention in response to fractional thickness of the sample.

FIG. 24 is a plot of confidence levels for an inflection point detection method according to an aspect of the present invention in response to fractional thickness of the sample.

FIGS. 32A, 32B are surface image representations of a plurality of nuclei from bovine cartilage tissue which have been imaged directly (raw) and after image enhancement according to an aspect of the present invention.

DETAILED DESCRIPTION OF THE INVENTION

Figure 11:
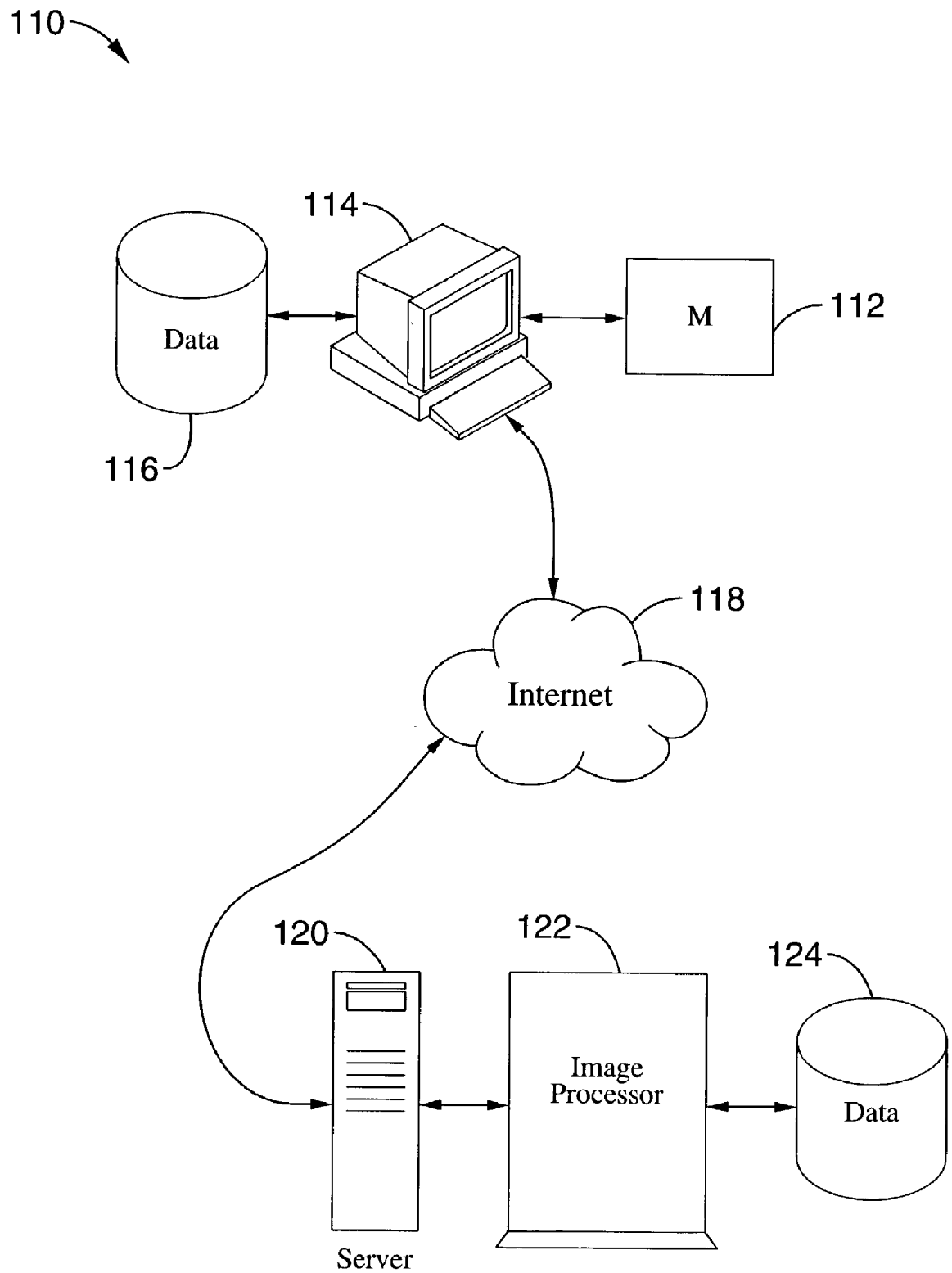
FIG. 11 is a schematic of a method of remotely processing image sets according to an aspect of the present invention, showing image data being communicated over a network for segmentation and/or other image processing prior to being returned to the originating organization.
Figure 12:
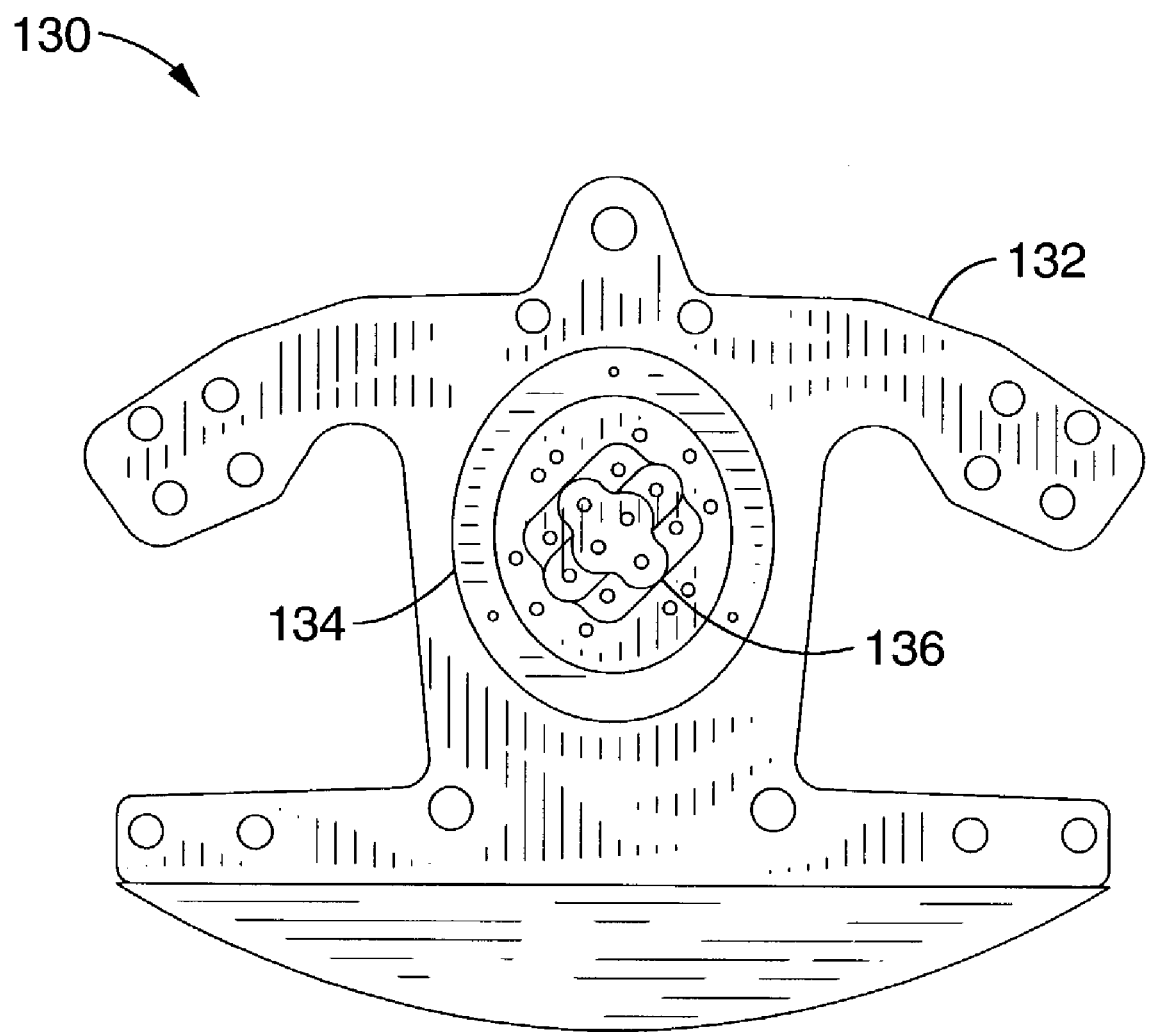
FIG. 12 is a front view of an implantable device about which tissue studies may be performed according to an aspect of the present invention, showing a sensor array placed within a portion of the window chamber of the device.
Figure 13:
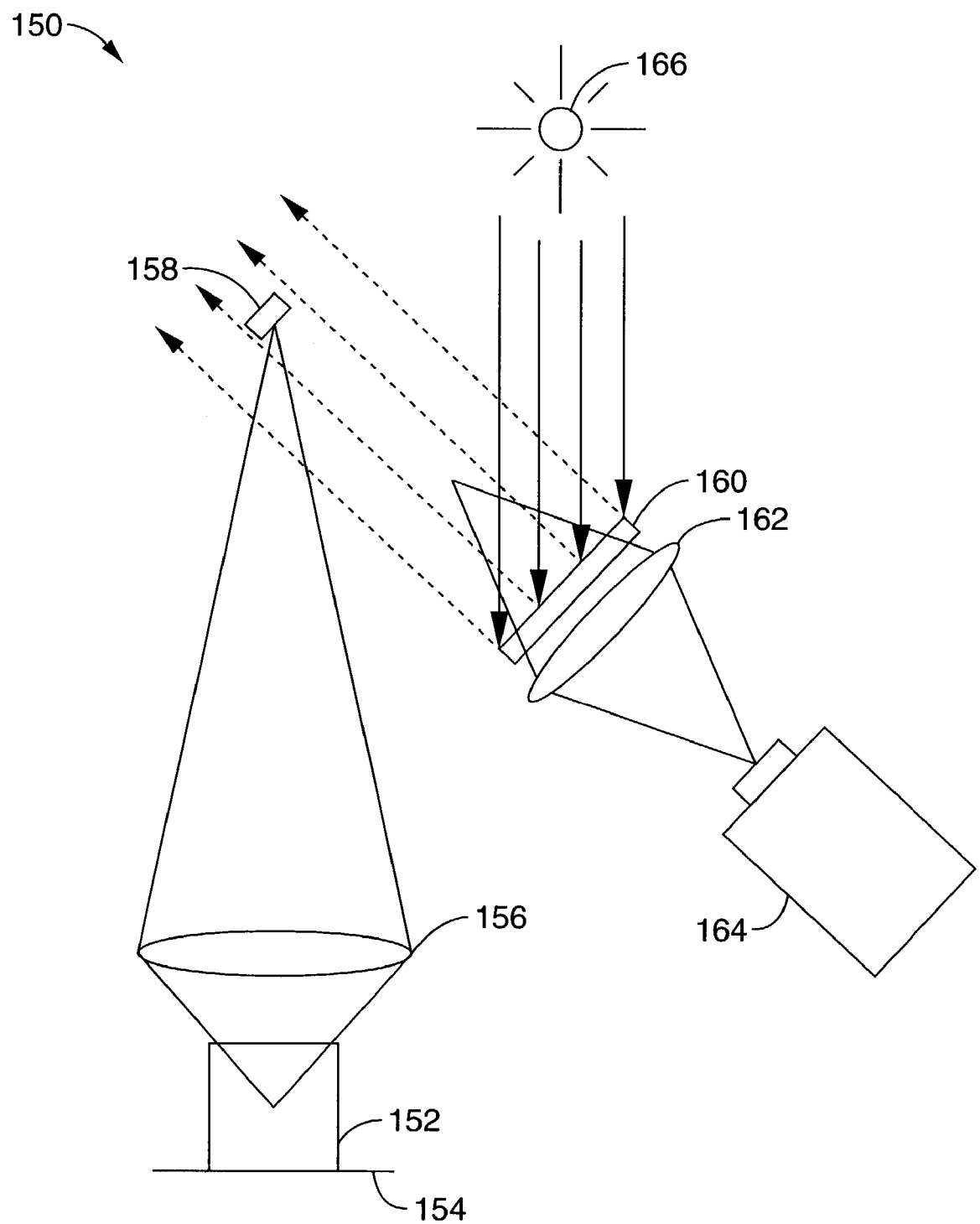
FIG. 13 is a schematic of the use of a digital micromirror device for generating spatial filtering to achieve confocal imaging according to an aspect of the present invention.
Figure 15:
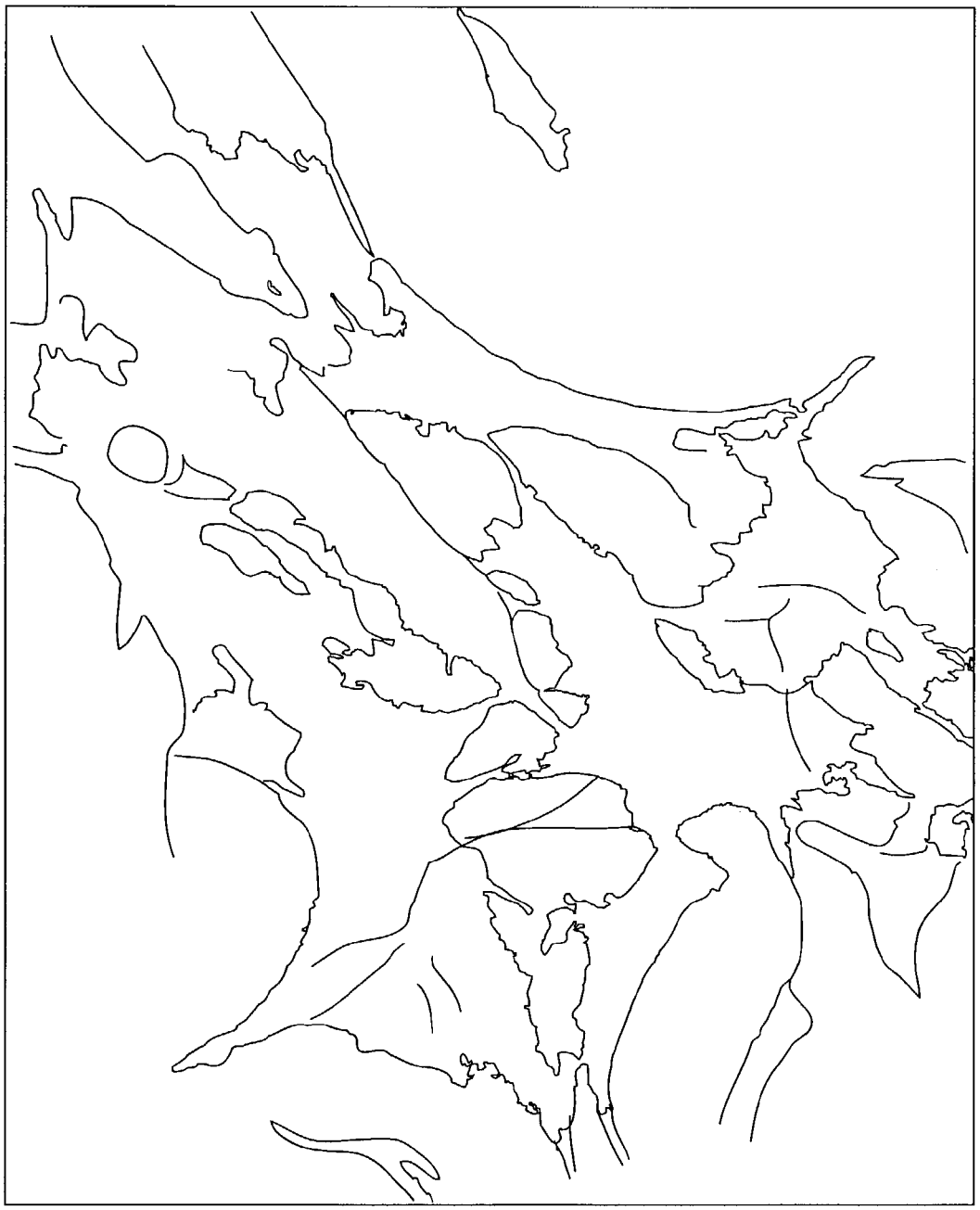
FIG. 15 is an image representation of fibroblasts with F-Actin stained with fluorescent Phalliodin being imaged by a confocal imager according to an aspect of the present invention.
Figure 16:
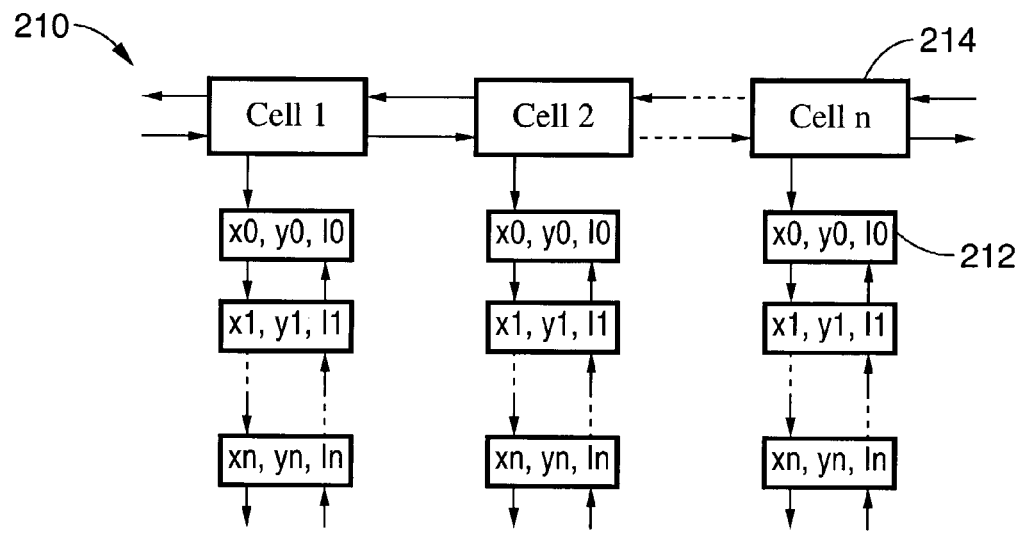
FIG. 16 is a data schema of a conventional 2D object data structure, showing cell structures with objects classified thereunder.

Referring more specifically to the drawings, for illustrative purposes the present invention is embodied in the apparatus generally shown in FIG. 2 through FIG. 33 excepting FIGS. 12, 13, and 16. It will be appreciated that the apparatus may vary as to configuration and as to details of the parts, and that the method may vary as to the specific steps and sequence, without departing from the basic concepts as disclosed herein. The present invention may be more particularly described in the following examples that are intended for illustrative purposes only, since numerous modifications, adaptations and variations will be apparent to those skilled in the art.

1. Introduction.

The present invention extends methods and systems developed for 2D and 3D image scanning to enhance the speed and accuracy of image segmentation and tracking of tissue samples using autofocusing during image collection. The present invention is generally applicable to a number of image collection systems and methods, aspects of which will be described in the following.

Enhancements for 2D cytometry have been developed toward reducing the speed impediment as a consequence of the need to focus the microscope in the Z direction as a scan proceeds in the X and/or Y direction. The development of high-performance scanning cytometry instrumentation for tissue engineering has been a highly successful imaging and confocal microscopy resource. One such system that has been commercialized based on these methods is available from Q3DM® located in San Diego, Calif. (http://www.q3dm.com). The system provides a number of improvements over prior cytometry methods and systems with a professional user-friendly GUI interface.

Figure 1:
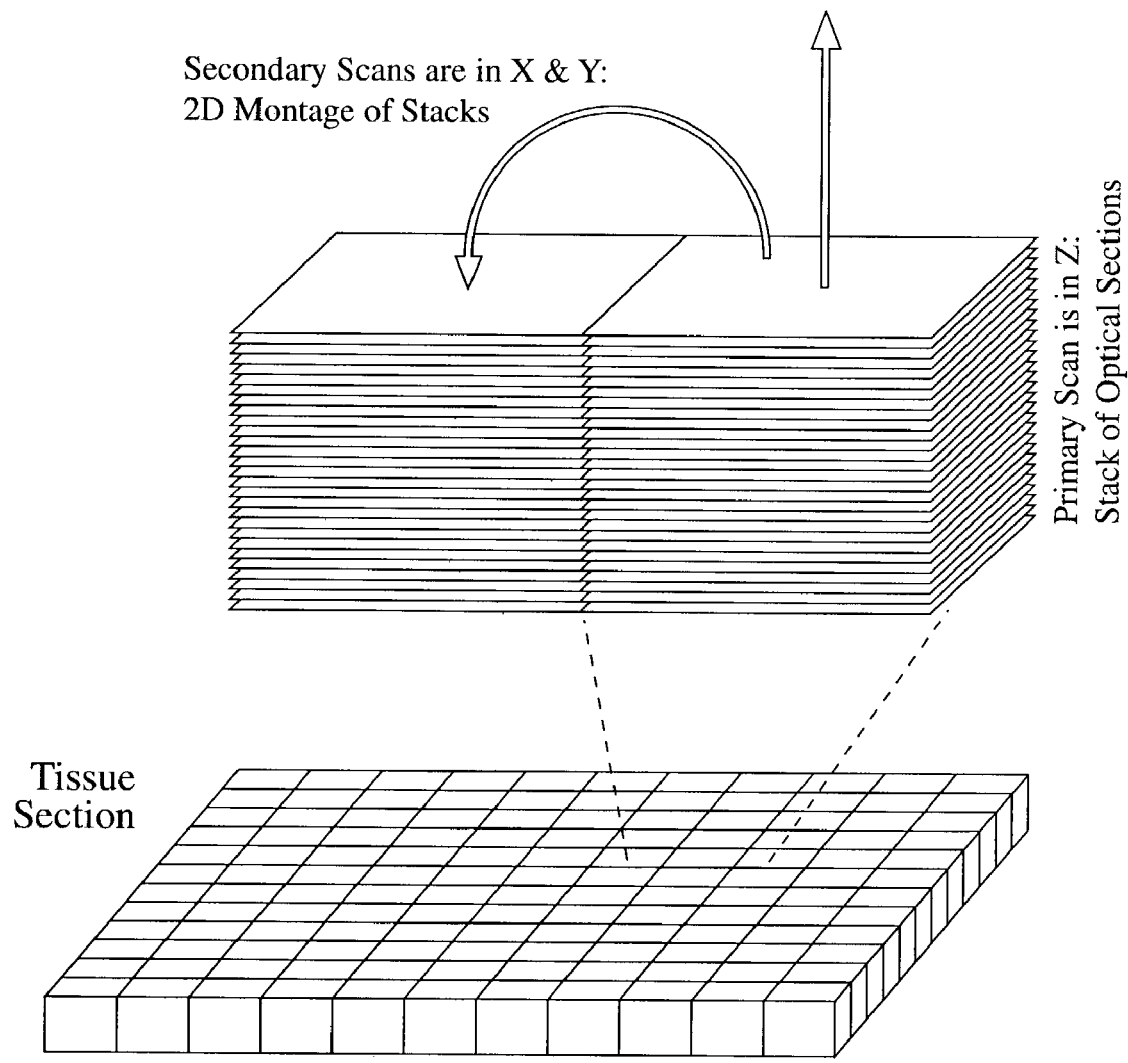
FIG. 1 is a diagram of conventional confocal scanning showing vertical (Z direction) stacks of optical images being captured in a step and repeat process.
Figure 2:
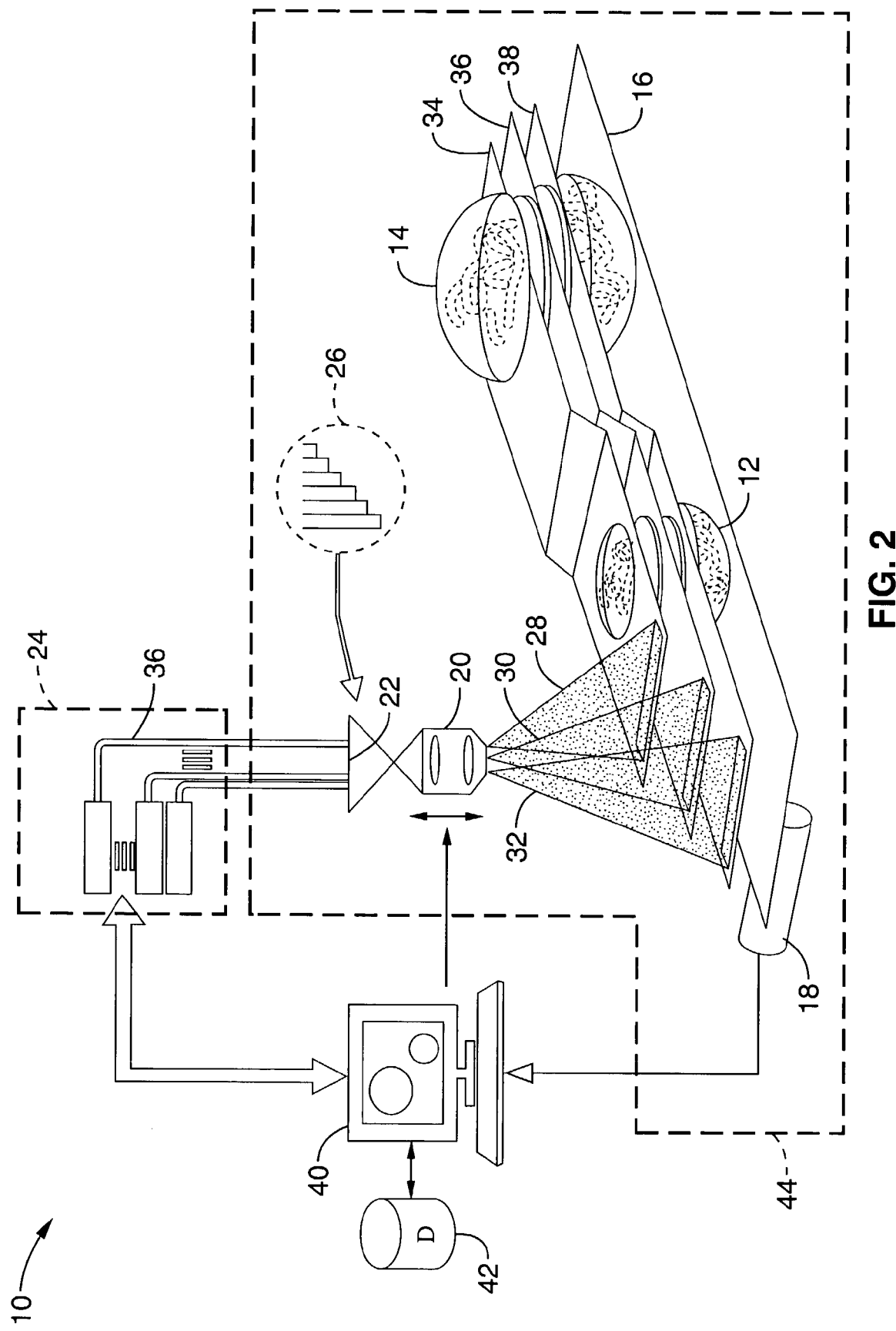
FIG. 2 is a schematic of a volume scanning microscope according to the present invention in which a series of image planes are simultaneously registered.

FIG. 2 represents an embodiment 10 of an on-the-fly autofocus and continuous scanning microscope that may be utilized for both 2D and 3D cytometry. First sample region 12 and second sample region 14 are shown on a movable stage 16. An encoder 18 is shown for registering stage motion and position. Objective lens assembly 20 receives optical energy which is directed to image plane 22. It should be appreciated that reflected, transmissive, or fluorescent optical energy may be collected by the objective lens system. An imaging array 24 is coupled to the image plane for simultaneously registering optical energy at different focal lengths. Imaging array 24 is shown by way of example comprising optical pathways extending to different lengths as shown in detail 26 within image plane 22. The focal lengths 28, 30, 32 are associated with three of these focal "steps", which respectively image paths 34, 36, 38 within first and second sample regions 12, 14. It will be appreciated that image paths are shown non-planar as a Z transition may be performed during scanning. A computer 40 is shown for receiving image data from imaging array 24 which can be stored on a storage medium 42, and for controlling stage and/or microscope movement. An environmentally controlled enclosure 44 is shown for maintaining the environment surrounding tissue samples at a desired conditions, such as temperature, humidity, and atmospheric composition.

When utilized for 2D cytometry the stepwise configuration of the optical fibers in the image plane of the objective create a stepwise set of in-focus optical planes in the specimen. The concept being that the 2D image will be substantially in focus at one of these planes at all times, wherein a separate Z translation stage for focus need not be executed during an X and/or Y scan of the sample. When utilized for 3D cytometry the image planes are collected, preferably in reference to at least one sample (i.e. tissue) surface wherein a sequence of image scans are created for use in generating 3D imaging. It will be appreciated that the number and spacing of image places determines the depth and resolutions of the volumetric scanning of the tissue.

By way of example the embodiment shown in the figure is described utilizing nine (9) time-delay-and-integrate (TDI) CCD cameras that collect the images from each plane and feed them to nine (9) autofocus circuits. These circuits feed the 9 sharpness indices to the computer (reducing the rate from 4 MHz for each TDI camera to about 100 Hz each) for on-the-fly calculation and setting of best focus. At least one additional camera may be incorporated for registering other image components. For example the inclusion of a trailing high-resolution cooled CCD camera for acquiring fluorescence images.

The volume scanning system provides high-speed continuous (on-the-fly) autofocus with target focal planes being are collected in parallel (simultaneously). Each scanning CCD camera is interfaced to one autofocus circuit allowing the focal indices for all planes to be calculated in parallel. The final best focus is calculated and set at about 100 Hz during scanning. This method speeds scanning cytometry by about an order of magnitude and allows for scanning of an entire slide in a short period of time, currently about five to ten minutes, depending on magnification.

FIG. 3A and FIG. 3B illustrate autofocus operation in obtaining a fluorescence image strip during a continuous scan of cellular tissues. The ability of the system to track focus is demonstrated by the clear focus of the objects shown in FIG. 3B as shown in detail from a section of the strip image shown in FIG. 3A. The narrow image of FIG. 3A is a 4-mm excerpt from an image of 30 mm of the microscope slide. This image was acquired with a 40×0.75 NA objective and the pixel size was 167 nm. FIG. 3B is a 0.5 mm long section blown up from an area nearby the arrow within FIG. 3A. Autofocus was update twenty four times along the 0.5 mm image section shown in FIG. 3B.

These long image strips are stored as smaller sections that can be processed directly by the same software utilized for incremental scanning. Thus, with the exception of the acquisition, stage movement and autofocus portions, the software utilized may be identical to that utilized for conventional incremental scanning. The continuous-scanning provided by this system provides numerous benefits in a number of cytometry applications. Comparable, or more rapid, imaging speeds may be provided with this technique than are provided with flow cytometry, wherein a number of applications previously thought impossible can become inexpensive and routine.

Cell-by-cell evaluation of entire microscope slides, which generates large amounts of precise cytometric data, is becoming routine. The boom of cell-based bioinformatics comes from automating access to this data. Data analysis tools that enable automated extraction of user-definable information from these cell measurements and images provide this data access. Pattern classification and data mining techniques organize the massive computer-generated information into a paradigm that can be quickly and easily managed by humans.

Figure 4:
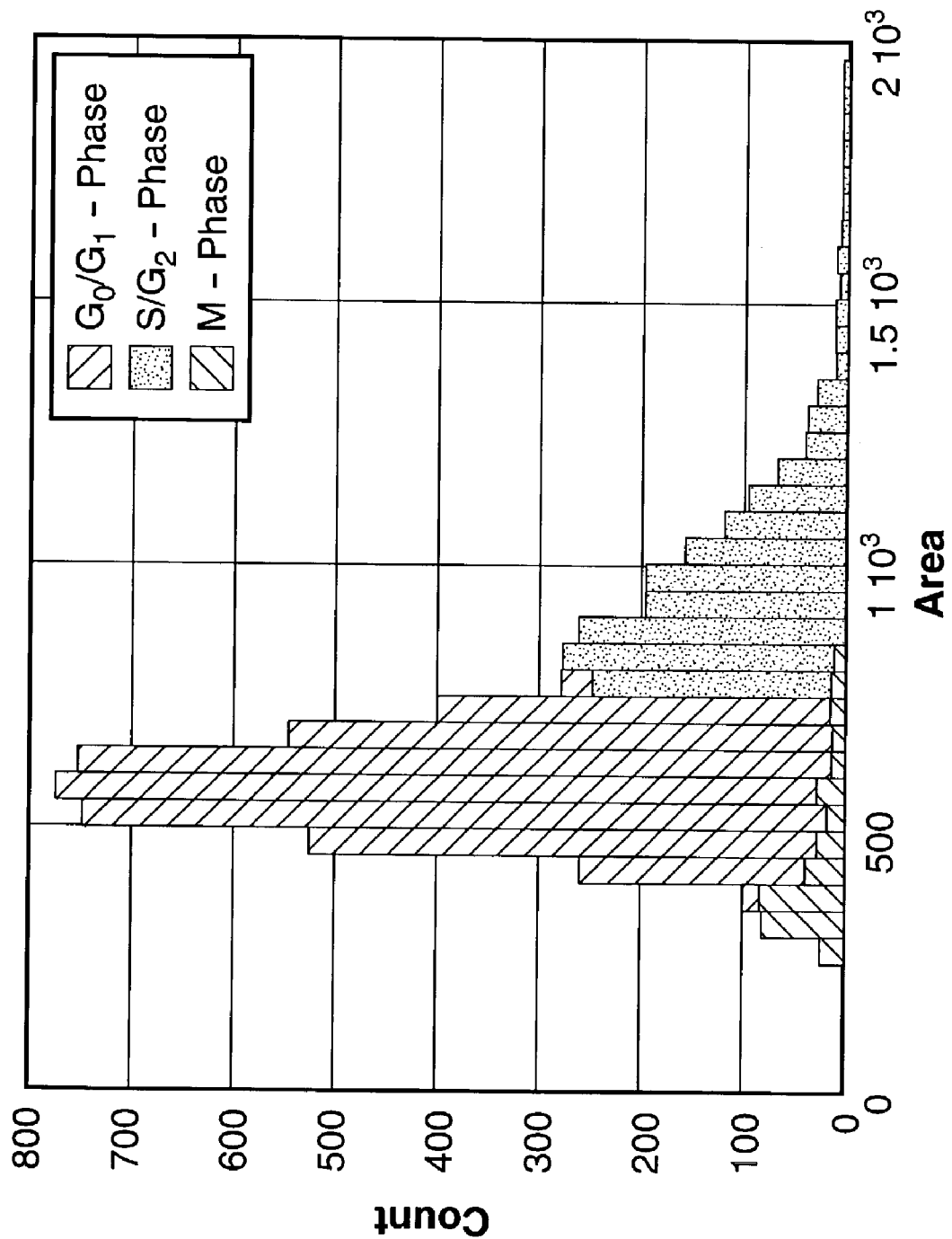
FIG. 4 is a histogram of area distributions in the $G_0/G_1$ phase, $S/G_2$ phase, and M phase as classified from image data by an artificial neural net according to an aspect of the present invention.
Figure 5:
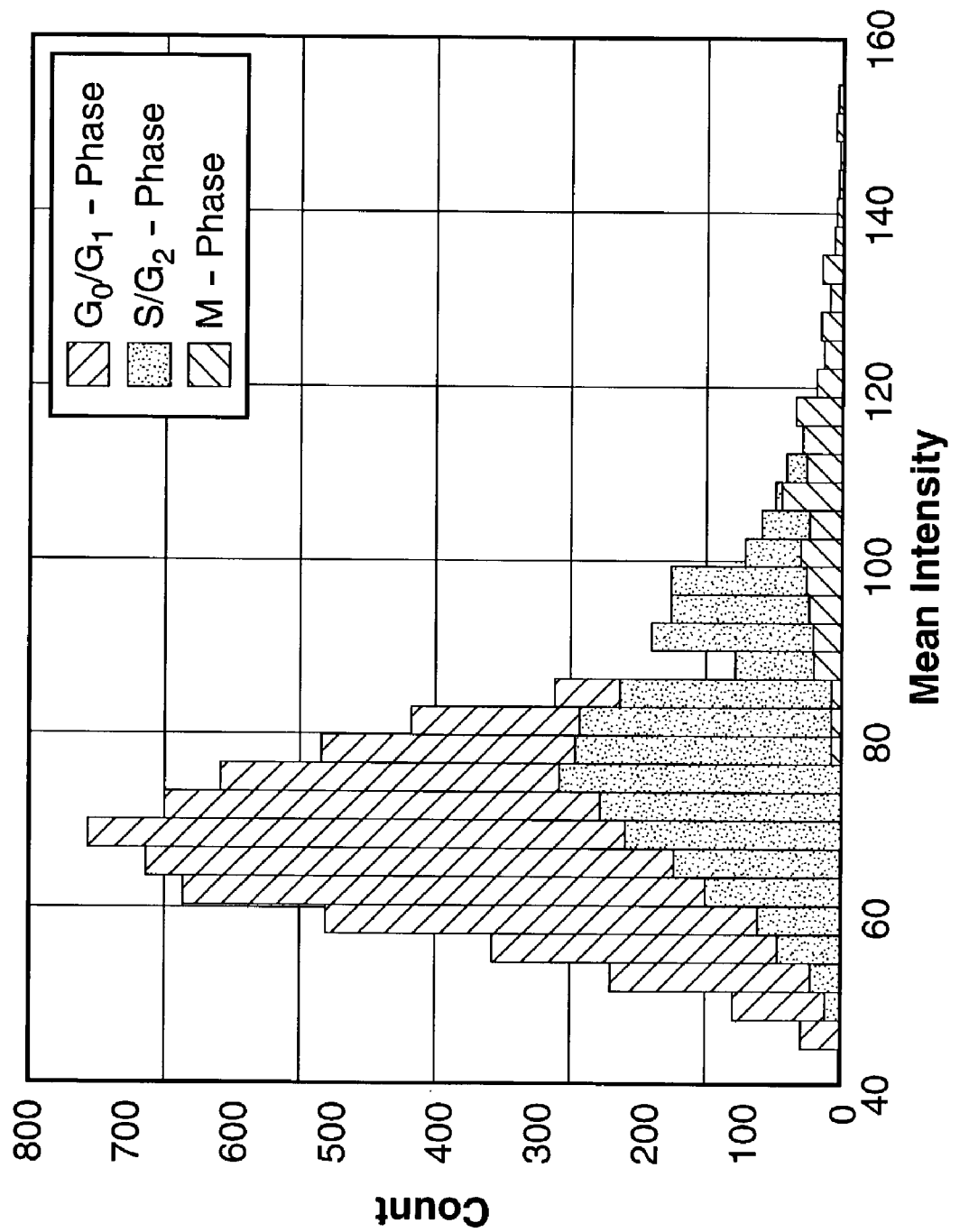
FIG. 5 is a histogram of mean intensity distributions in the $G_0/G_1$ phase, $S/G_2$ phase, and M phase as classified from image data by an artificial neural net according to an aspect of the present invention.
Figure 6:
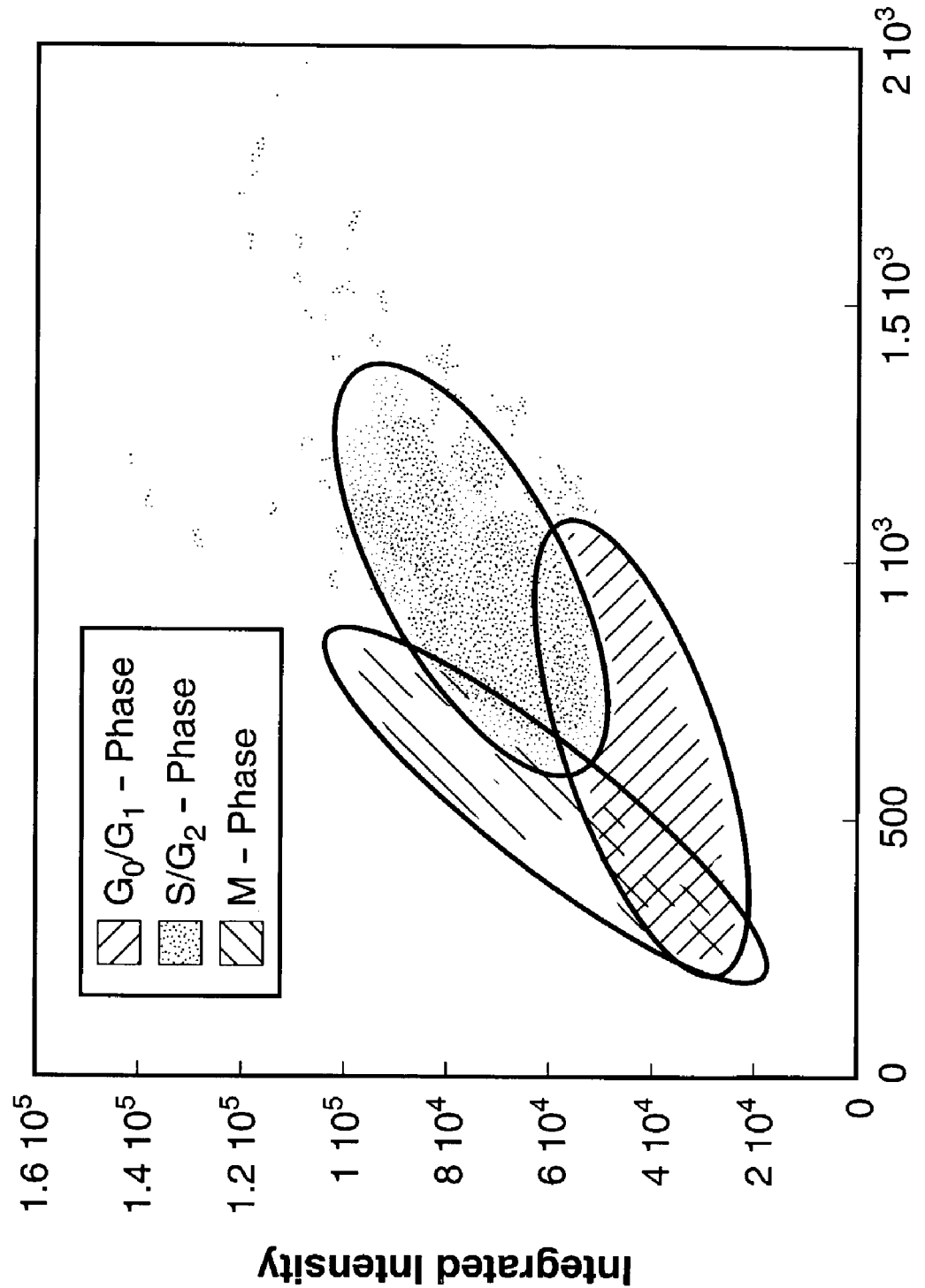
FIG. 6 is a histogram of integrated intensity in relation to area for the $G_0/G_1$ phase, $S/G_2$ phase, and M phase as classified from image data by an artificial neural net according to an aspect of the present invention.

FIG. 4, FIG. 5, and FIG. 6 demonstrate feature vectors that may be delineated using morphometry, fluorometry, and several kinds of texture analysis, such as those developed during 2D cytometry work. The figure depicts distribution and separability of features extracted from images of DAPI-stained NIH3T3 cells. The different shadings represent three cell groups separated according to cell cycle phases which are classified as $G_0/G_1$, $S/G_2$, or M phases. FIG. 4 and FIG. 5 illustrate feature histograms of area and mean intensity, respectively, while FIG. 6 is a scatter plot of a feature pair.

These feature measurements can be generally in 3D, such as demonstrated by Mackin et al. for conventional cell features. Fluorescence-stained intensity, shape and nuclear texture information are currently considered among the most reliable for classification tasks, so they are particularly appropriate for commercial development. The figure demonstrates such features by plotting nuclear area (FIG. 4) and intensity features (FIG. 5) versus cycle phase category. Separability between $G_0/G_1$ and M (mean intensity) and between $S/G_2$ and M (area) is shown. The prototype system utilized for collecting this data was not utilizing full image segmentation algorithms to improve feature separation further. For cell cycle phase analysis, the published 2D image cytometry data is of high precision and shows a CV of 4.4% for both $G_0/G_1$ and $G_2$. Analysis of the data in feature space using histograms and scatter plots can provide in depth insight of the distribution of subgroups of cell populations, along with clustering and data mining techniques that can facilitate cell classification, when no standardized testing and training sets are available. They also allow estimation of feature distributions and probability density functions for use with probability based or Baysian classifiers.

Artificial intelligence (AI) techniques have been applied to cytology for several decades now, but only with the recent advances in computing power can these approaches be applied to large data sets with reasonable speed. These classifiers are not dependent on the 2D or 3D nature of the cell image and rely on calculated feature vectors. Therefore, classifiers need to be retrained for 3D with new feature vectors, however, no change in classification methodology is generally necessary for the conversion to 3D images.

The use of different classifiers with 2D cytometry data has been explored. By way of example, preliminary data was completed using artificial neural networks (ANN) to classify phases of the cell cycle. ANNs are abstract mathematical models with the advantage that connectivity and weighting between inputs and output can be initially undetermined (weightings determined in response to training sets). However, ANNs by their nature do not provide any feedback on why a certain decision was reached and under what circumstances. By way of example the ANN for cell cycle analysis was written in Visual C++ (Windows 2000) and used a "back propagation" algorithm (gradient descent method) for use in multilayer networks. The example network comprised a three layer network with thirty five (35) input nodes, with eight (8) nodes within the hidden layer, and three possible decision outputs: M-phase cell, G-/S-phase cell, and other cell object. It should be appreciated that neural nets of various configurations may be assembled or simulated for performing the characterizations without departing from the teachings herein.

Preliminary results are shown in the confusion matrix depicted in Table 1 in which 112 cells were utilized for training the ANN, and 1061 cells were utilized for testing the performance of the ANN. Substantially larger training and testing sets should be expected to be required with this number of variables. It should be appreciated that the ANN may be retrained and utilized with other forms of cells, for example data obtained from synchronized cell cultures for each phase of the cell cycle. The results obtained during preliminary tests provide a wealth of information and are surprisingly accurate in view of the non-optimal conditions under which the cell images were acquired (i.e. no shade correction, no lamp stabilization). A similar albeit larger data set (3177 test cells, 3007 training cells) has also been employed with a simple quadratic determinant function which was programmed in Matlab™ using only two input features (mean intensity and area) to separate three cell cycle phases: $G_0/G_1$-, $S/G_2$-, and M-phase. The confusion matrix for this classifier is shown in Table 2.

Figure 7:
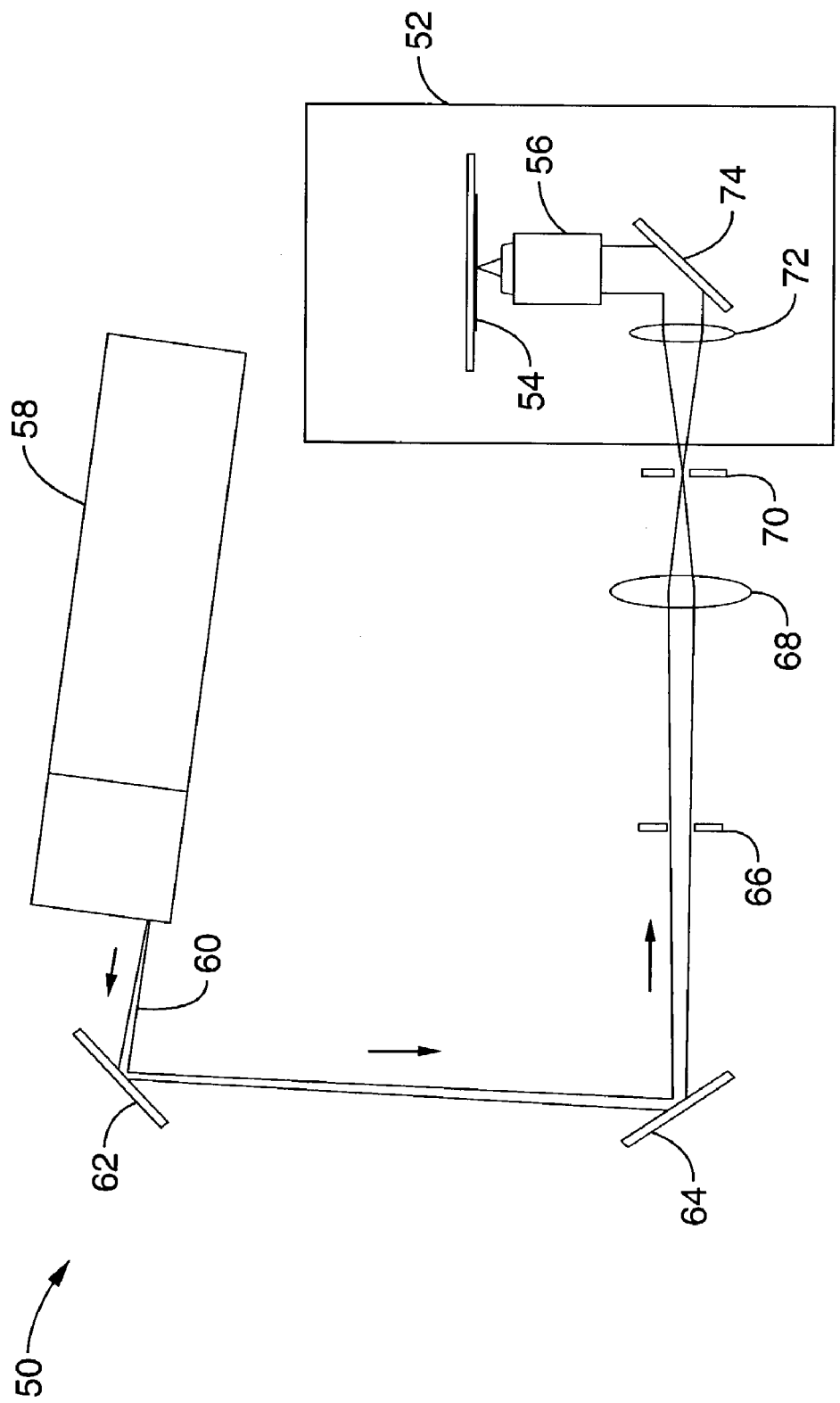
FIG. 7 is a schematic of an antivibration microscope table setup with the microscope shown in side view while the remaining equipment is shown in a top view, according to an aspect of the present invention.

FIG. 7 represents an optical system 50 incorporating an ablation system for negatively sorting out unwanted cells. For example, the ablation system preferably comprises a laser ablation system that is configured to apply a focused ultrashort laser pulse to each targeted cell. The system is shown in a preferable configuration assembled on an optical anti-vibration table. A microscope 52 in the figure is shown drawn as a side view, while the rest of the equipment is shown in a top view. The microscope 52 is shown with a cell culture on a well slide 54 over which is an objective lens capable of focusing received energy onto areas of the cell culture. A laser 58, such as a pulsed nitrogen laser (i.e. 337 nm wavelength) is directed by steering mirrors 62, 64 past iris 66, focusing lens 68, iris 70, focusing lens 72, and mirror 74 toward objective lens 56 to direct a light pulse to a focused location within the cell culture. The face of well slide 54 and iris 70 are conjugate planes. This type of system is particularly well suited for performing multi-day time-lapse sorting and data collection. The laser spot was focused to a sub-micron diameter and pulsed for a duration of 4 ns. It will be appreciated that various lasers may be utilized for this purpose, for example in reference to the figure a model VSL-337 nitrogen pumped dye laser of final wavelength 500 nm was obtained from Laser Science Incorporated® in Franklin, Mass.

In reference to the figure, the high power density ($>10^{10}$ $W/cm^2$) of the laser is available at the focal point which generates disruptive mechanical forces which are responsible for dispatching (killing) the selected cells. Fluorescently stained NIH-3T3 fibroblasts were used as model contaminant target cells in an unstained NIH-3T3 population to determine the identification-kill effectiveness. Ablation pulses were applied in frame-by-frame incremental batches to the cell culture on the microscope.

It should be appreciated that the 3D cytometer may be utilized in combination with a cell sorting and/or moving device, such as a laser based system forming optical tweezers or the like. It should also be appreciated that the 3D cytometer may be utilized in combination with a variety of MEMs devices positioned for interacting with a sample being imaged.

FIG. 8A, FIG. 8B and FIG. 9A, FIG. 9B depict results obtained from the exemplified ablation testing of NIH-3T3 cells described for the optical setup of FIG. 7. The drawings are representations of actual images taken during the ablation testing. FIG. 8A represents a phase contrast image of cells prior to ablation, with the small arrows shown pointing to the "contaminant" cells. FIG. 8B represents a fluorescent image before scanning ablation wherein model contaminant cells are shown stained with "CellTracker" Blue CMAC. FIG. 9A represents phase contrast images taken ten seconds after ablation, wherein the dead cells appear more opaque and have been subjected to movement in response to the laser pulse force. FIG. 9B represents a fluorescent image taken ten minutes after scanning ablation with the image of dead cells showing up in bright red due to staining with PI. CellTracker Blue does not bleed through the PI filter cube. It should be appreciated that all "contaminant" cells were killed by ablation during the testing while all "wanted" cells remained unharmed.

Microscopic imaging systems for use on tissues are typically implemented with an environmentally controlled enclosure, typically implemented as an "incubator". For example for use with long-term experiments (i.e. several hours or longer), such as laser ablation experiments. Incorporating an environmentally controlled enclosure allows incubating the culture during imaging operations with the microscope. It will be appreciated that due to the large number of cells involved, that a method to keep the cells viable is generally necessary. Controlling cell environment to act as an incubator for live cells allows the experiments to be conducted under controlled conditions. When performing a multi-day time-lapse test it is preferred that the station maintain the culture within desired range limits for temperature, pH, and humidity. An incubator was fabricated for tissue testing that formed a volume of ca. five cubic feet (i.e. dimensions being 30 inches×17 inches×17 inches), and incorporated an aluminum frame with acrylic covering plates. The example incubator was configured to allow adjusting the shape and dimensions of the frame to accommodate accessory position changes, or the inclusion/deletion of accessories.

The temperature within the incubator may be measured by an ungrounded thermocouple attached with silicon to the microscope stage. A controller that actuates a heating plate with a power of five watts per square inch (5 $W/in^2$), is shown being utilized for maintaining a desired temperature. To maintain the proper pH level, carbon dioxide ($CO_2$) gas may be maintained in the incubator air for buffering the culture medium. Another feedback control system, which may be implemented by a non-dispersive infrared (NDIR) sensors with diffusion sample draw, a digital control system and a $CO_2$ flow solenoid valve, may be incorporated for maintaining a five percent (5%) $CO_2$ concentration. The system described may receive test samples in any number of configurations, including open culture dishes, culture plates, and other cell chamber inserts.

2. 3D Segmentation.

The benefits provided by accurate 2D cell segmentation can be extended into three dimensions according to aspects of the present invention. Least squares finite impulse response (FIR) filters may be extended to three dimensions for use with 3D volumetric images. It should be appreciated that the 3D images according to use within the segmentation aspect of the present invention may be collected by any convenient method, including 3D scanning, step and repeat confocal microscopy, and so forth.

By way of example and not of limitation, the linear and nonlinear (perceptron criterion) versions of the least squares finite impulse response (FIR) filter design method were implemented in preliminary form using Matlab running on Windows 2000.

Figure 10:
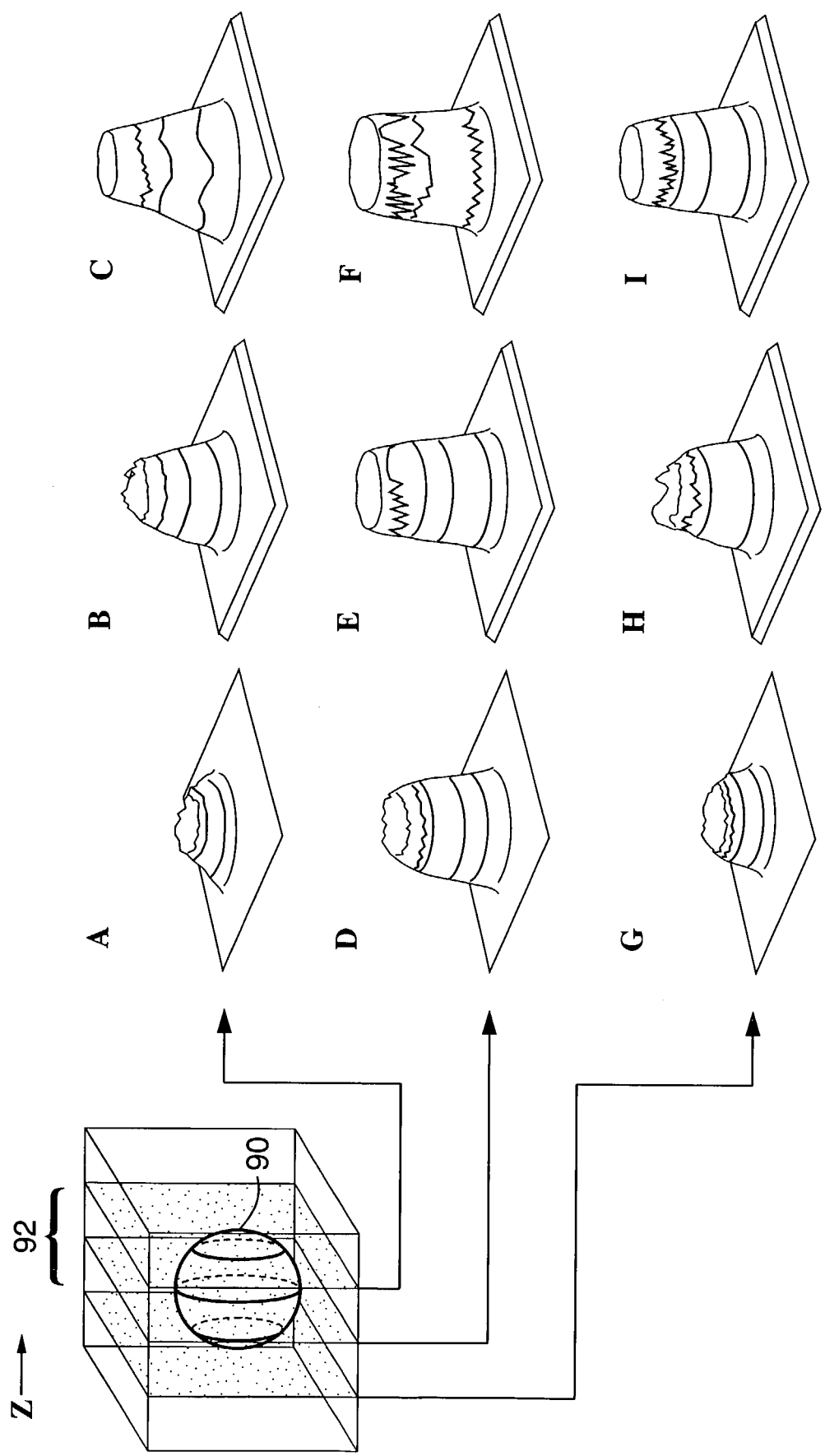
FIG. 10 are mesh plots of intensity of three optical sections of a 4 μm diameter fluorescent bead according to an aspect of the present invention, shown with sections A, D, G as the original images, sections B, E H, resulting from a 7×7×7 linear designed exact fit filter, and sections C, F, I resulting from a 7×7×7 nonlinear designed classifier fit filter.

FIG. 10 depicts intensity mesh plots representative of results generated from an embodiment of the 3D imaging system according to the present invention. Confocal images of a 4 μm fluorescent bead 90 are shown in the figure, intersected by three image planes 92 spanning a Z direction. These images were utilized for creating linear and nonlinear 7×7×7 FIR filters. Sampling was at 0.2×0.2×0.2 μm³. Sections A, D, G illustrate original images; sections B, E, H illustrate results of a 7×7×7 linearly designed exact fit filter; while sections C, F, I illustrate results of a 7×7×7 nonlinearly designed, classifier fit filter. All plots except the original images (A, D, G) were clipped at 255 (0xFF) to magnify the threshold region. This 55×53×55 voxel volume was taken from a Bio-Rad® MRC-1024UV confocal image of 4-μm fluorescent beads with a 60×1.4 NA Nikon® objective (160 mm tube length). The three optical sections represented were 17, 30, and 41.

For the linear FIR filter version (sections B, E, H) the error criterion is an exact fit, wherein object pixels are forced to a first value (i.e. 0xFF or 255 in decimal) and background pixels are forced to a second value (i.e. 0x00 or 0 in decimal). In creating the nonlinear version (classifier fit), the perceptron criterion was utilized. The classifier fit FIR filters (sections C, F, I) created substantially increased image contrast enhancement. Refer to section 7 for additional details on "Least Squares Contrast-Enhancing FIR filters".

It should be appreciated that the computation load of solving a nonlinear least squares problem for the coefficients of a 7×7×7 FIR filter on 3D data sets is considered very large by today's standards. It should also be appreciated that the implementation of the 3D filter in real time for performing image segmentation also can pose a burden, wherein special hardware is proposed as an aspect of the present invention to speed filtering. By way of example, several weeks of run-time can be required on current personal computers to design these 3D filters on appropriately-sized confocal images. Substantial reductions in processing time may be gained by the development of high-speed, parallel, software algorithms (methods). The algorithms may be configured to divide a large data set into segments whose size is efficiently processed by a single processor. Each segment may be distributed to a group of processors for performing concurrent processing. The resulting execution speed enhancement should be proportional to the number of parallel tasks less the additional overhead of task distribution and result collection. The embodiment described was implemented by way of example employing these parallel algorithms with the Message Passing Interface (MPI) standard. This standard provides high portability and scalability across a wide variety of parallel computing environments. By way of example, the development, coding, testing, and routine production runs described herein were performed on a set of seven networked Windows NT workstations with a MPI implementation developed by the Argonne National Laboratory and Mississippi State University, while large, one-time production runs were executed on a 272-processor, 154-Gflops Cray T3E which was located at the San Diego Supercomputer Center.

FIG. 11 depicts a method 110 of processing image data sets collected remotely. The system allows image data from a microscope 112 collected into a data set within computer 114, and optionally stored in a storage medium 116 (locally, offline, or remotely) to be transmitted over a communication link, such as an intranet or internet 118, to a remote image processing system 122. A server 120 is optionally shown for processing image requests from the internet which are processed by image processor 122. A storage medium 124 is shown for use during image processing and for storing image processing applications and routines.

Remote image processing system 122 is preferably configured with specialized resources such as filter algorithms, and may utilize specialized processing elements and/or architecture. It will be appreciated that this approach may be adopted for the processing of 2D images, although it is particularly well suited to the large data sets that can be created for 3D images, such as according to the present invention.

3. Related Research Activities.

The present invention can enhance interdisciplinary research tissue engineering by providing common focal points for scientific interactions. For example in studying the response of cytoskeletal organization to mechanical forces and its relation with adhesion molecules a number of different disciplines may be involved which may share the information made available by the present invention. The projects which may benefit from the invention span the whole spectrum of biological hierarchy, ranging from molecular biology to whole organ level, and entail close collaboration between bioengineering, electrical engineering, and life sciences. The following being provided by way of example and not of limitation of a small subset of research activities that may benefit from aspects of the present invention.

Study of depth-varying biomechanical properties of human articular cartilage.

Characterization of the efficiency of seeding of various chondrocte preparations onto a flat tissue surface, scanning of large volumes of seeded tissue.

Create quantitative maps of cellularity in the repair site of cartilage defects.

Categorize structural and functional properties of skeletal muscle.

Create vast subcellular 3-D mapped brain databases.

Study epithelial tubulogenesis, branching morphogenesis and cellular migration of kidney tissues over time.

Study mechanical properties and electrical activation of collagen and muscle fibers of the beating heart.

Study blood flow microcirculation in-vivo to determine oxygen transport response to biosensor implantation.

Characterize the tissue response to oxygen-dependent implants with unprecedented detail.

Study morphology and cell-cell interactions over large volumes of microfabricated hepatic tissue over increasing 3D structures.

Study the processes underlying the establishment and maintenance of regular cell patterns during plant development including the control of cell division orientations and the spatial regulation of cell expansion.

Study migratory and homing characteristics of hematopoietic stem cells (HSCs) including dynamic formation and retraction of surface extensions of pseudopodia, tenupodia and magnupodia.

Characterize time dependent, 3D deformation physiology of adherent endothelial cells in response to shear flow.

Study large scale, sub-cellular fluorescent ratioing of ex-vivo preparations and investigations into shear induced gene-transcription.

Develop an in-vitro bioartificial liver precursor using hollow fiber bioreactors.

Characterize the interplay of fluid dynamics and biological response in hollow fiber bioreactors.

The following disclose in more detail a small sampling of the recent studies that could benefit from utilization of the present invention. It should be appreciated that these studies are provided by way of example, as the method and systems of the present invention may be utilized in a number of different applications without departing from the teachings of the present invention.

3.1 Cartilage Tissue Engineering.

NIH P01 AG07996-09 (Sah, R. L.) Apr. 1, 1997-Mar. 31, 2002 Studies of Joint Aging, Osteoarthritis Biomechanics and Repair. The objective of this project is to determine the depth-varying biomechanical properties of human articular cartilage, particularly as related to human aging and degeneration. A major method of accomplished this involves micro-compression testing of cartilage, and video imaging of the sample. Currently, imaging results for the sample are limited to two dimensions. Extension of the imaging method to three dimensions with automated 3D cytometry would markedly enhance the measurement method. Currently, this is the rate limiting experimental method in these studies.

3.2 Articular Cartilage Repair.

NIH R29 AR44058-04 (Sah, R. L.) Apr. 1, 1996-Mar. 31, 2001. This study characterizes the deformation of regions of cartilage tissue near a cut edge when subjected to mechanical loading. Cellularity is expected to be lower near the cartilage surface in adult tissues. Currently, imaging of the sample pair is limited to two dimensions, and as in NIH AG07996, analysis of samples is tedious and a rate-limiting experimental procedure. Generation of stereo projections images and three dimensional characterization would speed the process while more readily conveying results. For example three-dimensional taken through 120 µm of Ethidium Homodimer (DNA fluorescent dye) stained cartilage to illustrate cell distribution with depth. The opportunity to image the response of living cartilage daily for days without photodamage as a model of cartilage wound healing is particularly compelling.

3.3 Mechanisms & Enhancement of Integrative Cartilage Repair.

NIH R01 AR 46555 (Sah, R. L.) Mar. 1, 2000-Feb. 28, 2005. The objective of this study is to determine if transplantation of chondrocytes onto a cartilage surface enhances subsequent integration with another flat cartilage surface. The proposed studies involve characterization of the efficiency of seeding of various chondrocyte preparations onto a flat tissue surface, and would benefit from more detailed morphological characterization of the cells. The availability of high-speed confocal 3D cytometry enables rapid analysis of large volumes of seeded tissue. Furthermore, with automated 3D imaging, the degree of cell flattening can be assessed. The change in cell shape is typically associated with transition from a desirable chondrocytic phenotype to an undesirable fibroblastic phenotype. Measurement of the morphology, phenotype, and migration of cells into the cartilage provide a more complete assessment of cartilage repair in this in-vitro tissue model. These studies are impractical utilizing current technology.

3.4 Circumferential Seeding of Chondrocytes using Rotating Bioreactors.

NASA NAG 8-1571 (Sah, R. L.) Jan. 1, 1999-Sep. 30, 2002. The objective of this study is to develop bioreactor technology to allow seeding of chondrocytes onto the circumferential surface of cartilage of osteochondral cores. Such osteochondral cores are currently utilized in autogenic transplantation procedures to repair cartilage defects, however, these suffer from the inability to integrate with the adjacent host cartilage. A critical aspect of this work is to rapidly characterize the location of chondrocytes seeded onto the circumferential tissue surface. Using the present invention the sample may be rotated above a microscope objective to allow characterization of the entire circumference of the sample at a given time. Rapid three-dimensional cytometry at prescribed intervals therefore greatly speeds the data acquisition and reduces temporal displacements during image scanning.

3.5 Cell Biology of Epithelial Morphogenesis.

One such study is focused on the cell biology of epithelial morphogenesis, and specifically, the identification of soluble factors and genes involved in morphogenesis, including tubulogenesis, branching and response to injury. Primarily, the study is directed at cells and tissues of the kidney, although other tissue types may be similarly studied. A number of in-vitro systems using cultured embryonic cell lines, embryonic primordial tissues (i.e., ureteric bud or metanephric mesenchyme) and whole embryonic organs are employed for these cell and molecular studies. Essential to all such projects is accurate correlation of gene and protein expression with morphological changes for which high speed confocal analysis is essential. Equally important is the need to devise reliable confocal based quantitative assays to assess how perturbation of gene function affects morphogenesis. This requires the accumulation of many images and their composite analysis. It will be appreciated, therefore, that this research would also see substantial benefit from using high-speed 3D cytometry, such as according to the present invention. It should be appreciated that the tissue under study (i.e. evolution of ureteric buds) is highly complex, and may require analyzing millions of cells. From a practical standpoint accurate testing over such as large data set requires automated instrumentation, such as provided by the present invention.

Use of the present invention, for example, could compress the scale of research, wherein research that would normally require man-years of labor could be shortened into a period of days, thereby enabling entirely new levels of bioinformatics understanding.

The ureteric bud undergoes branching morphogenesis in-vitro and develops three-dimensional tubular structures in the absence of mesenchyme. E-13 rat ureteric bud was isolated and cultured as described. After culture, the ureteric buds were fixed at different time points and processed for DB lectin staining. Three-dimensional confocal images may then be taken of. (a) A freshly isolated ureteric bud from an E-13 rat embryonic kidney with a single branched tubular structure. (b) The same ureteric bud shown in (a) cultured for 3 days. (c) The same ureteric bud shown in (a) cultured for 12 days. The collected images and data can illustrate the growth of the protrusions and repeated dichotomous branching to form structures resembling the developing collecting system of the kidney. When viewed at higher powers, the structures formed in this in-vitro culture system exhibit lumens. Phase microscopic examination and staining for markers revealed no evidence for contamination by other tissue or cells.

The cultured three-dimensional tubular structure is capable of inducing nephrogenesis when recombined with metanephric mesenchyme. The isolated ureteric bud was first cultured for 7-10 days as described in (a) above. After which the cultured ureteric bud was removed from the ECM gel and recombined with freshly isolated metanephric mesenchyme from E-13 rat kidneys. The recombinant was cultured on a Transwell filter for another five (5) days. After culture, the sample was double stained with DB lectin (FITC) and PNA lectin (TRITC) as described in (b) above. Results indicate that the in-vitro cultured ureteric bud derived structures are capable of inducing nephrogenesis in-vitro.

3.6 Tissue Studies Relating to Implantable Devices.

An important class of implantable devices requires the capability to control and design oxygen transport properties at the tissue/implant interface. These devices include: metabolically active implants based on living secretory tissue that is encapsulated by an immunoprotective synthetic polymer membrane. Implantable biosensors to monitor oxygen, glucose, lactate and other biochemicals based on enzyme electrodes that require oxygen as a co-substrate.

In both cases, sustained oxygen transport from the tissues surrounding the implant is essential for function. However, not enough is known about the factors that affect formation and permeability of the fibrous capsule that often surrounds implants, the characteristics of the implant that encourage a proximal vascular supply, and the time-course of development of these features. In one of these studies a sensor array is placed in the window chamber with the active face of the electrode array visible in the center of the frame. It should be appreciated that electrodes may serve as oxygen sensors or counter electrodes.

FIG. 12 exemplifies an implantable device 130 which may be utilized in combination with the present invention for studying tissue response to implants. The implant shown has a body 132 within window 134 containing a sensor array 136. By way of example the sensor array is shown comprising electrodes in the active face of window 134. The electrodes can serve as oxygen sensors or counter electrodes. It should be appreciated that the present invention may be utilized for studying tissues associated with any implantable device, and that a variety of sensors, MEMs devices, and other implant related elements may be incorporated upon which tissue studies may be performed with methods according to the present invention.

The 3D cytometry of the present invention can provide for low-dose live measurement of living tissue to assess this complex interaction of blood flow, vessel formation and scar development. The new technology enables a completely new paradigm of cellular informatics that will allow rapid evolution of biomaterials.

4. Description of Research Instrumentation and Needs.

Current instrumentation is not suited to the needs of tissue researchers. Confocal microscopes are generally considered too slow, while 3D imaging tools are too rudimentary, for allowing scientists and tissue engineers to analyze the millions to billions of cells that exist within a given tissue volume (e.g. blood has 5 B cells/ml).

The present invention, however, can make many tissue research projects practical, while significantly increasing the practicality of other forms of tissue research or clinical tissue microscopy. The present invention provides rapid 3D imaging segmentation. The embodiment of the invention is generally described in relation to use on a Texas Instruments® (TI) Digital Light Processing® (DLP) high-speed confocal microscopy upon which real-time 3D image segmentation has been added according to the present invention to create an automated high-speed 3D confocal cytometer. The instrumentation development objectives are to:

1. Developing high-speed multi-color fluorescence DLP confocal PAM. Multi-channel optics are to combine the three laser lines (two new lasers and one existing 532 nm laser) for multicolor fluorescence excitation. A binary formatter (i.e. manufactured by Texas Instruments) is incorporated to provide 100 Hz simultaneous imaging (optical section rate) in all three channels (with the Dalsa 4-tap CCD cameras).
2. Implementation of real-time 3D image segmentation. The research provides for automatically locating cells in 3D images. Image segmentation is fundamentally important for automating access to cellular data on millions of cells.
3. Creation of 3D cytometrics, image-and-measurement database, and classification-driven visualization. Three-dimensional run-length encode cell-image data structures are provided for fully automated measurement and storage of cell images and measurements. The cell-image-linked data is made available to the user through expert system and classification algorithms for transparent and rapid access and collating of data on large populations of cells.

Although Nipkow disk and slit-scanning confocal systems can provide imaging at high rates (hundreds of Hz), no current techniques may be as sensitive, flexible, and simple to use as the programmable array microscope (PAM) systems, such as based on recently constructed Texas Instruments™ based DLP systems. The 3D confocal cytometry system described utilizes both the DLP PAM experience and extensive 2D cytometry expertise. The advent of high-speed confocal microscopy provides the basis for 3D cytometry, with the generation of accurate, real-time image segmentation being the crux of the automated 3D cytometry challenge. The methods utilized for 2D image segmentation are extended within the present invention for providing accurate 3D segmentation that may be implemented in real time, such as on an array of high performance digital signal processors (DSPs).

The first fully automated 2D scanning cytometry instrumentation based on 2D segmentation technology was introduced by Q3DM®. Image segmentation is the basis for automatically locating cells on a slide, making measurements of the cells, and collecting the cell images and data into a virtual slide database construct for simple access. The present invention can benefit from the autofocus methods developed in 2D cytometer, and from additional autofocus enhancements described herein.

An implementation was described for a 3D confocal cytometer providing a target imaging rate with 100 Hz optical sectioning resulting in a 100 MB/s peak voxel rate. The required 3D image operations are currently intractable at this rate on conventional workstations, however, real time processing may be implemented on DSP chips, such as using C62x and C64x DSP technology from Texas Instruments®.

It should be readily appreciated that information availability is a foundation of progress. The human genome has been sequenced. And although knowledge of the base pair sequences alone do not reveal the mysteries of life, disease, and death, few would choose to venture forward without them. Understanding how those genes translate into function is extremely challenging and the tools are limited. The use of DNA arrays create a wealth of knowledge about the average cell in a population but are unable to reveal the complexities of expression across individual cells of which that population is comprised. Flow cytometers, however, can provide cell-by-cell measurements on large populations of cells, yet are unable to perform those measurements in-situ to record behaviors. Scanning (image) cytometry can make automated in-situ measurements of cells, but these are limited to two-dimensional scans. Confocal microscopy creates 3D images of intact tissue, however, the cell populations are practically constrained to tens or at most hundreds (if the operator is extremely patient) of cells that may be practically studied.

Tissue is natively 3D and studying it in its native conformation can yield tremendous information gains if that information can be rapidly acquired and easily accessed. Destroying even a very few genes within a cell can result in cell death or other easily observed changes. However, cell behavior is extremely complex, wherein changes in a single gene may result in only subtle changes in cell behavior or alterations that manifest themselves only under environmental stress. A mutation leading to cancer, for example, may not manifest as cancer for many cell generations, in which other mutations or damage is sustained to other portions of the cell mechanisms. The use of tissue imaging in 3D which provides focusing and segmentation according to the present invention is a powerful bioinformatics tool that provides direct information about the structure, organization, relationships, behavior, and expression of individual cells in a large population of cells.

FIG. 13 depicts the basic principle of DLP reflection confocal microscopy 150. A sample 152 is shown on a stage 154 imaged through objective lens 156 with image reflecting from micromirror 158 directed partially through beams splitter/dichroic mirror 160 and through lens 162 to sensor 164, such as a CCD. Conversely light is transmitted in the opposing direction through the device from light source 166 to sample 152.

In operation a single micromirror 158 is utilized to create a reflection "pinhole" that generates the spatial filtering to achieve confocal imaging. Micromirror 158 acts as both the illumination and emission pinhole. A dichroic mirror 160 directs light from the light source 166, such as a lamp or laser, to micromirror 158. Micromirror 158 selects a portion of that light and directs it to the sample 152 through the microscope optics 156.

Fluorescent light from sample 152 returns along the same path to micromirror 158 and is reflected through the dichroic mirror 160 to the sensor 164. Light from different focal planes passes by micromirror 158, and is not reflected to sensor 164. This selection by the reflection "pinhole" creates the confocal filtering. It should be appreciated that light may also be reflected off of the specimen if the dichroic mirror is replaced with a polarizing mirror.

Figure 14:
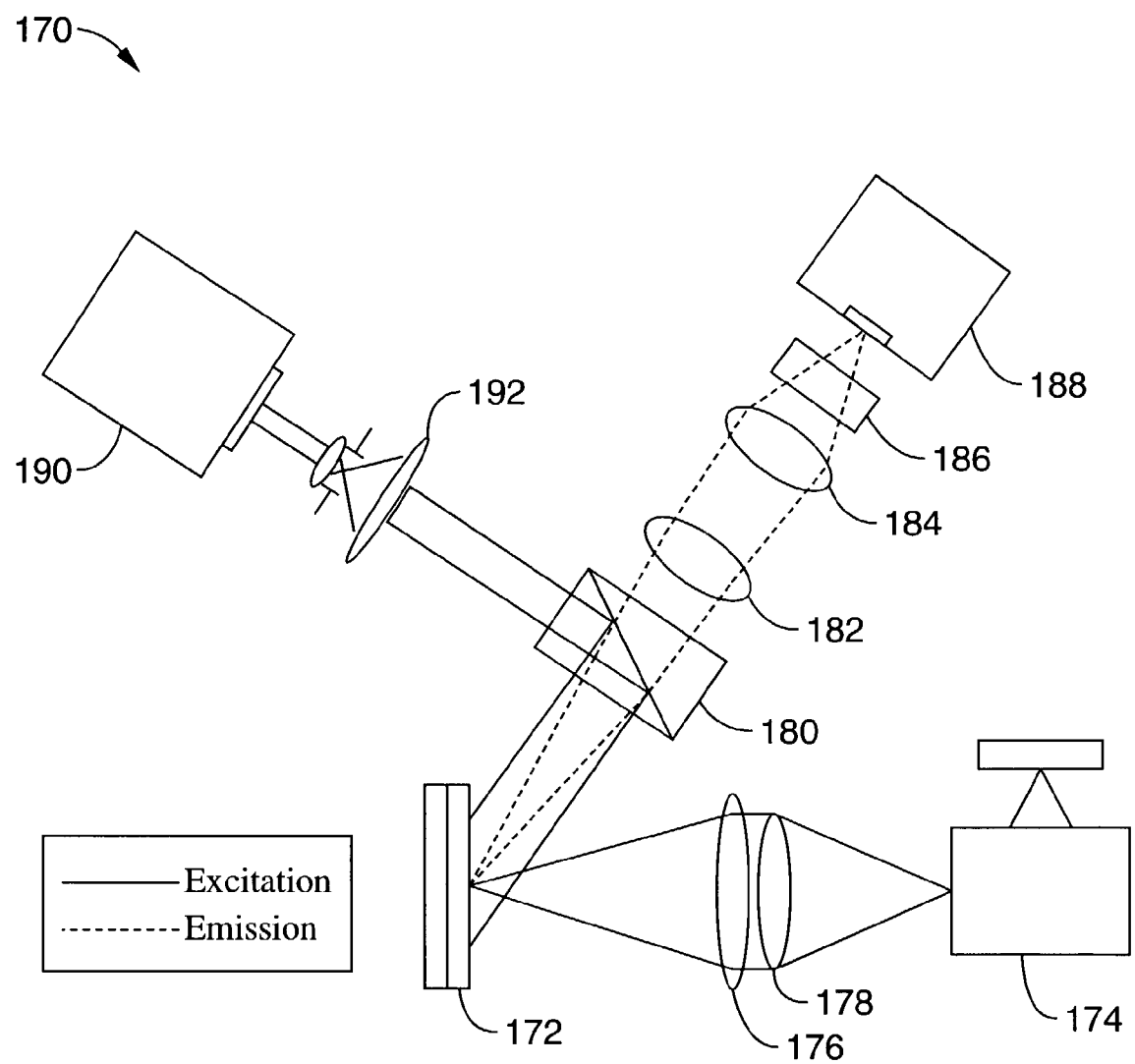
FIG. 14 is a schematic of a digital micromirror confocal optical system according to an aspect of the present invention, shown with a laser excitation source coupled through the digital micromirror array to the sample and the collection of emissions returning from the sample.

FIG. 14 depicts a diagram 170 of the embodied DLP (or digital micromirror device, DMD) confocal system. The DMD 172, containing hundreds of thousands of 16×16 μm² micromirrors is shown near the side port of the inverted microscope 174 (i.e. Nikon® TE300 microscope). A pair of lenses 176, 178 are shown between DMD 172 and microscope 174. Imaging is performed as light passed through dichroic mirror 180, lenses 182, 184, emission filter 186 into sensor 188, such as a CCD. Excitation energy is received from a light source 190 and passed through a beam expander 192 toward dichroic mirror 180 which directs the light toward the sample. DMD 172 front surface plane can be placed perpendicular to the image plane of the microscope (by using additional relay optics) or it can be tilted to compensate for the tilt of the micromirrors. A ten degree tilt in the magnified image plane results in less than a 0.2 degree tilt with a 60× objective because the vertical magnification is approximately the square of the lateral magnification. When a micromirror is flipped one direction (in the ±10° range) the light is reflected into the microscope (ON) and when it is flipped the other direction the light is reflected elsewhere (OFF). The pattern of ON and OFF mirrors determines the degree of confocality, sensitivity, and other performance parameters.

FIG. 15 represents a spot scan image of fibroblasts with F-Actin stained with Fluorescent Phalloidin (Molecular Probes Alexa series). A confocal optical section from this system of fibroblast cells is shown stained with a fluorescent dye for F-actin (a cytoskeletal protein). A high resolution image is obtained that without the confocal imaging would contain a much larger proportion of blurry light from out-of-focus regions of the cells. The original image (upon which the rendition of FIG. 15 is based) was collected with a spot scan—each being a 5×5 region of micromirrors on the DMD contained one ON mirror at any given time. The ON mirror was "moved" to each adjacent mirror in every neighborhood until every mirror had been ON for an equal amount of time to "scan" the entire image onto the CCD sensor.

To image the microvasculature, hamster window chambers were placed on male golden hamsters. This chamber preparation allows for the direct observation of the microcirculation in conscious animals over prolonged periods of time permitting multi-day longitudinal studies of the microvasculature. An arterial catheter was inserted into the left carotid artery of the hamsters to allow injection of indicator dyes. Prior to imaging, FITC-Dextran (70,000 MW) or DiI stained red blood cells were injected into the circulation via the catheter. Hamsters were imaged on days 1, 3, and 5.

A binary formatter is preferably utilized that allows confocal optical section acquisition at over several hundred Hertz (the theoretical limit for a 5×5 neighborhood spot scan being approximately 1 kHz).

The speed of the DLP PAM confocal system utilized in the described embodiment is currently limited by the need to write to the DMD chip through a VGA interface. An enhanced binary formatter with a faster interface can eliminate that speed limitation. Positioning along the Z axis is preferably performed using a piezoelectric objective positioner, such as produced by Polytec PI® of Irvine Calif.

The present invention provides real-time 3D image segmentation having the accuracy required for practical scanning cytometry. Previous methods suffer from a number of drawbacks including the need for operator interaction to correct image segmentation errors, while they generate substantial errors that propagate to cell measurements, or are impractically slow for use in analyzing large numbers of cells (i.e. that extend past the low thousands of cells and can extend up into the millions and preferably the billions.)

Accurate image segmentation was achieved by finding the best (in the least squares sense) FIR filter for increasing the sharpness and object-background contrast and simplifying the subsequent thresholding step. For image G, segment S, and spatial FIR filter K, the segmentation procedure is $$F = K * G$$

$$S = \begin{cases} C_0, F < T \\ C_1, F \geq T \end{cases} \quad (1)$$

where * is the convolution operator, F is the filtered image, T is the threshold, and $C_0$ and $C_1$ represent the two classes of segmented images (e.g., $C_0=0$ and $C_0=255$ for DAPI stained cell nuclei). This function is a two-category linear classifier implemented subsequent to the spatial FIR filter.

Given the input image G and an ideal segmented image $I_S$, it is possible to solve for the FIR filter that best maps G to $I_S$ with the choice of an appropriate error criterion. The best error criterion is one that reduces the error of thresholding. This error can be calculated by minimizing the pixel-by-pixel error from an arbitrary object-background contrast in an effort to achieve segmentation insensitive to the subsequent threshold. The perceptron criterion, widely used in classification schemes, provides this error measure. The use of a margin with the perceptron criterion incorporates the importance of achieving a minimum contrast between the background and object classes in order to reduce the errors expected in subsequent thresholding. These methods are explained by Duda and Hart. The criterion can be written as follow:

$$E = \sum \begin{cases} (I_S - F)^2; & A < F < B \\ 0; & \text{otherwise} \end{cases} \quad (2)$$

The FIR filters designed by this method dramatically enhanced object-background contrast and allowed automatic thresholding. These filter design methods were applied to ten different images and the filters designed for each image were tested on the other nine. An example of the resulting image segmentation accuracy was published using ten test images containing a total of 1,070 sub-images of cell nuclei. The technique achieved the high levels of accuracy for real-time image segmentation as required for fully automating high-speed image cytometry.

It should be appreciated that Eq. 1 and Eq. 2 are completely general in terms of image dimensionality. In theory, they can be just as easily applied to 3D images as to 2D images. The most labor-intensive step in this method is creation of the interactively defined ideal images. The embodiment will describe the use of a spherical fluorescent stained latex beads (commercially available from Molecular Probes, Eugene, Oreg. and others) of known diameter and intensity to eliminate the labor-intensive step of creating 3D segmentation standard images interactively. Utilizing beads of known size and shape, it will be possible to create standard images by locating the centroids of the beads and replacing the confocal bead images with synthetic images of the spherical objects. The performance of the FIR filters designed in this manner will be compared with those designed from a more limited set of interactively segmented cells to ensure that the simpler method achieves the appropriate accuracy. Use of the fluorescent bead method can greatly simplify and speed design of 3D FIR filters. The hypothesis on creating these filters is that a large portion of the task of an FIR filter is to perform a sharpening (similar to deconvolution) on the edge of the object. The difference is that it does not have to reconstruct the detail at high resolution, yet only needs to contrast-enhance the edge. Based on the research performed using 2D image segmentation, this assumption appears valid, while the results also tend to validate the assumption. Therefore, there is strong data to indicate that this will also provide a valid and powerful 3D image segmentation method.

Software for the least squares FIR filter design may be implemented in any desired language, such as Visual C++, and be configured to execute on any processor family, such as the proposed multiprocessor Intel PC workstation running Windows 2000, or similar. In parallel with FIR filter design, the present embodiment includes software written to perform real-time 3D image segmentation on the Coreco™ image processing hardware. The image processing work is distributed among a collection of processor resources, in this case a series of twelve digital signal processors (DSPs). The best method to be utilized will depend on both interprocessor bandwidth and processing speed. If processor speed is the limitation, then the best approach involves sending each successive optical section to a different processor, and all of the 2D FIRs that make up the 3D FIR filter would be applied to that optical section in a single processor. Adding together the appropriate 2D FIRs then creates the resulting 3D FIR. This method requires increasing bandwidth to transfer the 2D FIR results as the 3D FIR increases in the $3^{rd}$ dimension. With more limited interprocessor bandwidth, it may make more sense to break the input image stream into sub-volumes, perform the full 3D convolution on each 3D sub-image, and then reconstruct the full FIR-filtered image from the sub-images, to minimize interprocessor communication. It will be appreciated that both of these methods, or combinations thereof may be utilized for 3D. It should be noted that when implementing small kernel filters, such as is required here, the convolution operation is much faster than Fourier filters. This is especially true given that the integer, or fixed point operations required for FIR filtering are significantly less costly from an execution standpoint than the floating point operations required for executing Fourier filters.

5. Description of 3D Data Structures.

The present invention creates 3D cytometrics, an image-and-measurement database, and classification-driven visualization. This work is based on 2D cytometry and a low level database that represents the image objects (cells). The image segmentation step, as described above, creates binary image masks of each object. For the database of the objects, the object pixels are sorted into run-length encoded (RLE) linear arrays of X, Y location and length.

FIG. 16 depicts 2D representation in which each connected RLE 212 is sorted into the data structure for each cell 214. The header of each cell (or object) can also store the measurement data.

There are many details to this structure that are not shown. For example, objects sometimes contain holes (non-object pixels surrounded by object pixels). Holes can be found by creating a second image that is reversed—all object pixels converted to background pixels and background pixels to object pixels, sorting the new pixels into (background) objects, and checking to see which of these new objects does not touch the edge of the image. If a background object does not touch the edge, it is a hole inside another object. Each hole is then assigned to an object which can be tracked in 3D.

Figure 17:
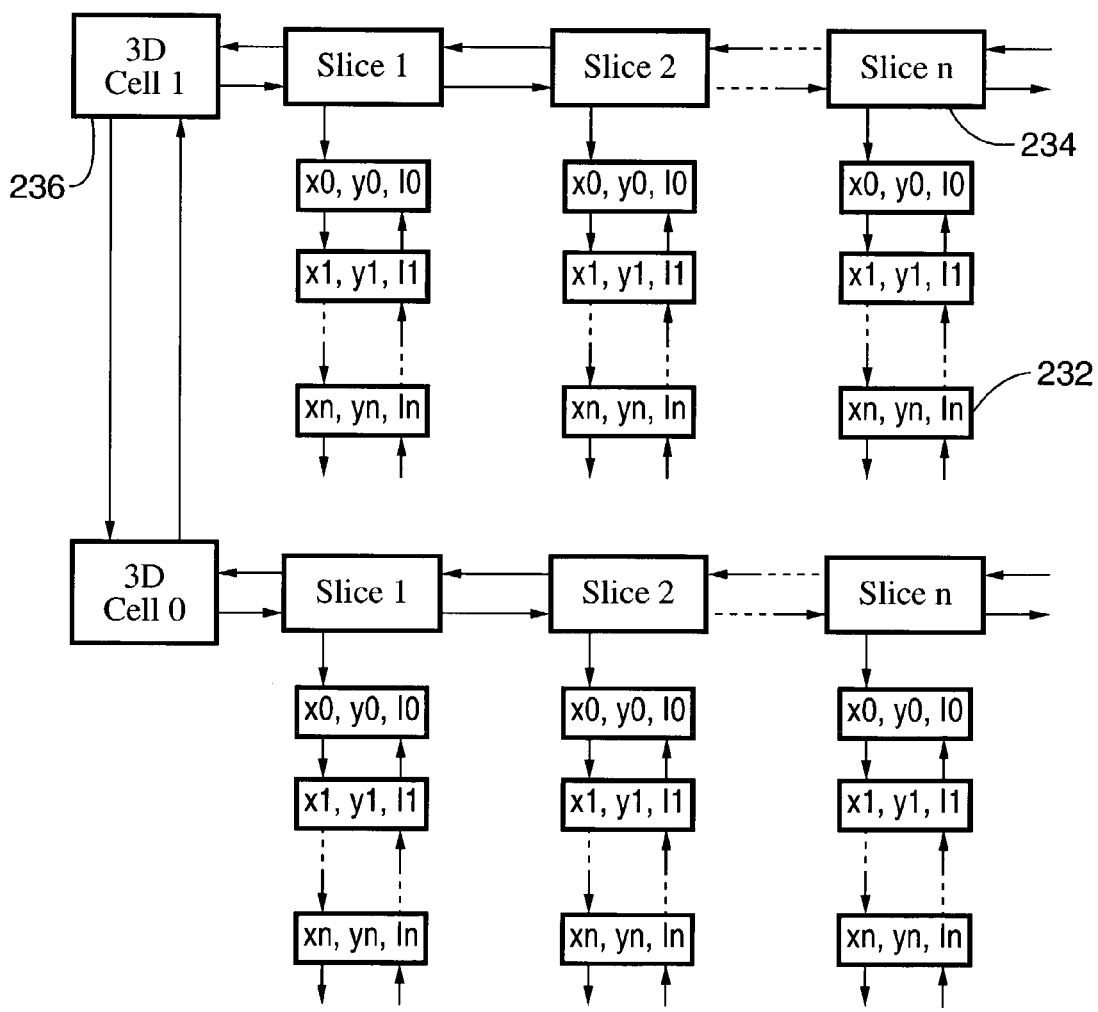
FIG. 17 is a data schema of a 3D imaging structure according to an aspect of the present invention, showing 2D cells being subdivided into slice sections under which objects are classified.

FIG. 17 depicts the extension of 2D structures into the 3D structures 230 of the present invention. Objects 232 are retained under each slice 234 which are retained for each cell 236. Each object from the 2D representation has thereby become a slice in this 3D object representation system. In this manner, much of the 2D data structure design can be reused while structural similarity is maintained. Each of the "Cell" header structures in the figure also contain pointers to a list of holes.

The 3D data structure in FIG. 17 can also be utilized to generate an image database by providing the bounding information for each cell. As the RLEs are sorted onto the object data structures, information about the objects is also collated and stored. One such piece of information is the bounding box. Although this term is often utilized in reference to 2D images, wherein perhaps a more precise term for 2D would have been "bounding square", as a "box" is a 3D structure which was previously not being implemented. Therefore, in describing the present invention, the tags "2D" and "3D" will be used for clarification. Once the bounding box is known, the region-of-interest (ROI) comprising all of the pixels (or voxels) that make up the object which can be stored. By storing only the bounding box image information, a substantial amount of empty background can be ignored, saving substantial storage space. Each of the "Cell" headers in FIG. 16 also point to a ROI image that was contained in the bounding box. In this manner, the 3D objects also automatically contain the 3D image. However, the "3D Cell" headers could also be used to point to 3D bounding boxes if access is deemed faster even though storage requirements would be somewhat larger depending on the complexity of the cells.

The real-time image segmentation generates 3D masks that define the extent of each cell in 3D space. A database for storing the underlying images and measurements in 3D (volume, pattern, intensity, morphometry, and so forth) corresponding to each cell along with the location of each cell. This allows rapid access of data and images. A complete infrastructure for identifying, storing and retrieving 3D cell images is provided. As with 2D classification research, it is contemplated that 3D efforts will proceed much more rapidly when researchers have instant access to constructs of cell-images-and-data. Once the 3D cytometer has performed the image segmentation and stored the 3D cell images, the corresponding feature database allows rapid redesign of expert system and classification techniques. Thus, the infrastructure proposed here is key for realizing the bioinformatics gains possible from extensive 3D cytometry data.

6. Tracking Tissue Section Surfaces.

The present invention introduces new aspects over 2D cytometry in developing a 3D automated XYZ imaging system. One aspect of the present invention for 3D XYZ imaging is the automated detection of the top and bottom of the tissue section. This aspect of the invention may be applied for use in various 3D imaging devices, although its use within a scanning cytometer will be primarily described by way of example. An autofocus circuit according to the invention measures the sharpness of the image as the power of the high spatial frequency components. Power drops quickly outside the tissue section, and can be utilized for automatically detecting the top and bottom of the section and for creating a 3D map for scanning in XYZ. Knowledge of tissue boundary, or boundaries can reduce storing image data for background areas to which the tissue sample does not extend.

Figure 18:
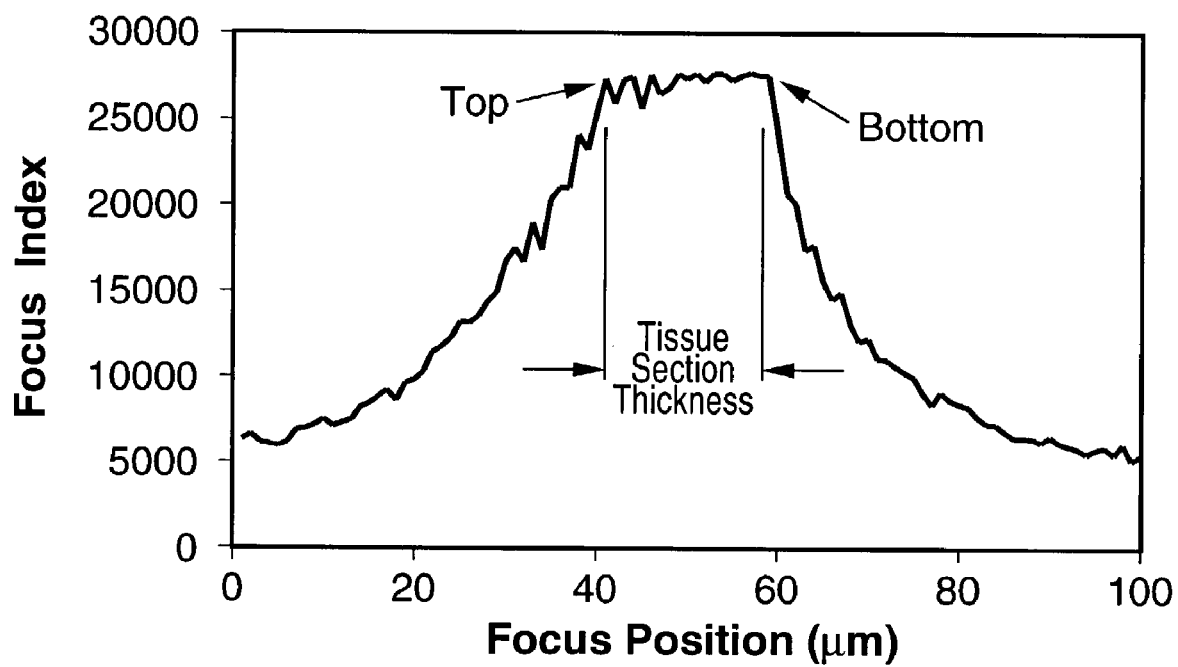
FIG. 18 is a plot of a focus index, sharpness measure, registered for a section of tissue according to an aspect of the present invention which provides for detecting tissue surface location.
Figure 19:
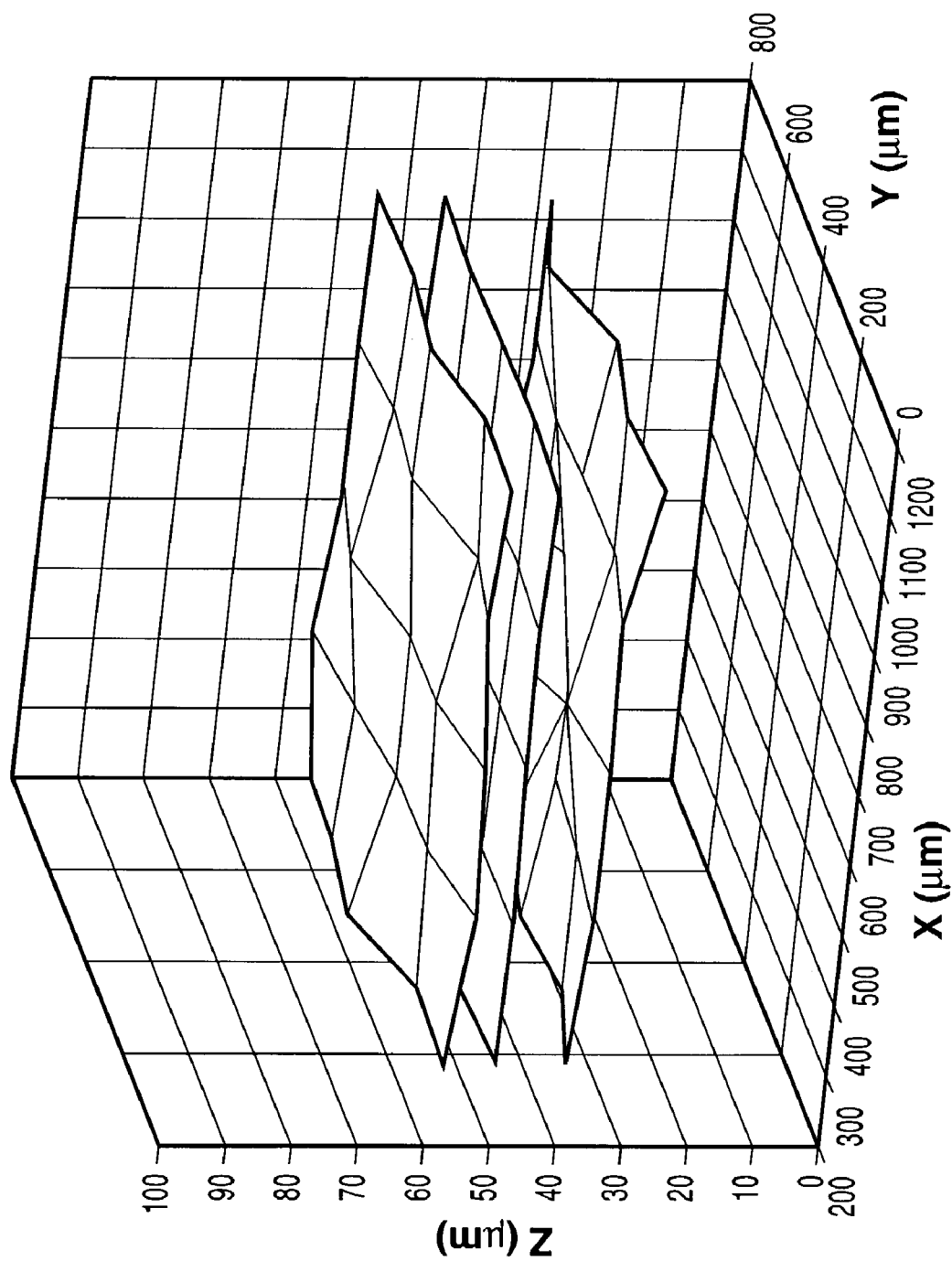
FIG. 19 is a plot of focus meshes determined according to an aspect of the present invention showing top, middle (or average best focus), and bottom of a tissue sample.

FIG. 18 and FIG. 19 depict examples of through-focusing plots on tissue samples. In FIG. 18 a through-focus plot of the focus index (sharpness measure) is shown for a 15 μm tissue section without index of refraction correction. "Top" is nearest the coverslip and up-side down on the inverted microscope (i.e. Nikon® model TE-300 microscope). In FIG. 19 surface plots of the top (blue), best focus (green), and bottom (red) of the same 15-μm tissue section as in FIG. 18 are shown over an extended view of 5×5 microscope fields. Each point depicted in the mesh plots represents a single field. The top and bottom positions identified using this autofocus circuit correlated closely with manually observed top and bottom focus positions.

It will be appreciated that three-dimensional cytometry, whereby large volumes of tissue would be measured automatically, requires a computerized method for detecting the upper and lower tissue boundaries. In conventional confocal microscopy, the user interactively sets limits for axial scanning for each field-of-view. Biological specimens vary in section thickness, thereby driving the requirement for manually setting vertical scan limits. Setting limits arbitrarily large to ensure the entire tissue is scanned results in inordinately large data sets.

Automatic surface identification within the present invention may be utilized with various imaging systems including step-and-repeat, or scanning instruments, scanning, to eliminate the storing of undue numbers of empty optical sections. Surface identification may also be utilized for the basis of lateral microscope stage motion to collect unlimited numbers of stacks. This walk-away automation of 3D confocal scanning for biological imaging is the first step towards practical, computerized reconstruction of arbitrarily large three-dimensional images from many stacks.

Initial results for automatic tissue surface tracking were obtained for phase-contrast microscopy by measuring focus sharpness. Measurements were taken from 5×5 fields-of-view from hamster liver sections, having thicknesses which varied from five to thirty microns in thickness. These images were then smoothed to lessen noise and eliminate statistical outliers. Because image sharpness (as the power of high spatial frequency components) drops across the axial boundaries of a tissue section, the full-width at half-maximum and second derivative were used to locate tissue top and bottom. Results from these tests were evaluated against manual (i.e. visual) determination of section boundaries.

Tissue was prepared in the test by excising fresh rat liver which were cut roughly into cubes and placed in a saline solution, such as Dulbecco's Phosphate-Buffered Saline (PBS). Tissue blocks were covered in O.C.T. (i.e. from Tissue-Tek) embedding medium for frozen tissue specimens and sectioned onto microscope slides in 5 μm, 10 μm, 15 μm, and 20 μm thicknesses using a cryostat, such as a Leica® model CM 3050 cryostat. The specimens were subsequently rinsed in PBS to remove excess O.C.T. and coverslips were fixed with Gel Mount biomedia with edges being sealed, such as by applying nail polish to the edges and letting it dry.

Tissue specimens were imaged under phase-contrast illumination, such as on a Nikon model Eclipse TE300 inverted microscope with a Nikon model LWD 0.52 condenser lens and Nikon Plan Fluor 40×/0.75 Ph2 DLL objective. Images were acquired, such as by a Cohu 6600 Model 3000 progressive scan camera (Cohu™ of San Diego, Calif.) attached to a Nikon CCTV 0.9-22.5× zoom lens. The images were then digitized to 640×480 pixels by a Matrox Meteor II multi-channel frame grabber (Matrox™ from Dorval, Quebec, Canada) in a 500 MHz Pentium II dual processor host computer. Lateral stage movement in X and Y directions was controlled by a stage, such as supplied by New England Affiliated Technologies stage with stepper motors (New England Affiliated Technologies™ of Lawrence, Mass.) having a microstepping driver, such as a NuDrive™ microstepper from National Instruments of Austin, Tex. The nuDrive microstepping driver is controlled by a motion control board, such as a National Instruments™ (NI) ValueMotion PCI-Step-40× motion control board. Focus was changed using an objective positioner, such as manufactured by Polytec PI or Tustin, Calif. The objective positioner utilized in this instance is a piezoelectric objective positioner (PIFOC) and E610.L0 closed-loop controller which provides a 100 μm range. PIFOC positions were controlled by the host computer via a National Instruments NiDAQ data acquisition board having a 12-bit D/A converter. Focus functions for autofocus were calculated with a Q3DM AFx-3000 autofocus circuit.

Software to record focus function data from the Q3DM autofocus circuit was written under Microsoft Visual C++ 6.0. All signal processing algorithms were developed using MATLAB 6 Release 12.

Data were obtained from 5 μm, 10 μm, 15 μm, and 20 μm (nominal) thick sections of tissue, which in this case comprised hamster liver. For each thickness of microscope slide, the microscope was initially adjusted to a plane of best focus manually so that the stage was at approximately the middle of the PIFOC's axial travel range. Once a focus position was found, images were acquired at 0.5 μm intervals 50 microns above and 50 microns below this level, i.e. through the PIFOC's total range of motion. The relationship of focus function to image intensity being previously known in the industry.

The PIFOC position was reset and, without image acquisition, ten sets of focus functions were recorded to provide statistics and a characterization of noise in the measurements. Without further manual focus adjustment, the stage was automatically moved, and the preceding imaging and focus function recording steps were repeated until data from 5×5 adjacent fields-of-view were recorded.

The images collected through the 100 μm range were used for manual identification of the boundaries of the tissue section. It was noted that noise filtering of the focus function data would be required prior to correlating with the tissue boundaries. A number of filtering methods may be utilized, including different FIR lowpass filters as well as moving window averages. Within this test a Savitzky-Golay filter design was implemented in a math CAD program (i.e. MATLAB) in which the routine can reproduce the effects of a lowpass filter and have the additional advantage of returning differentiation filters. For the purposes of this paper, the order of the polynomial approximation is K=3, and the frame size is F=11.

Figure 20:
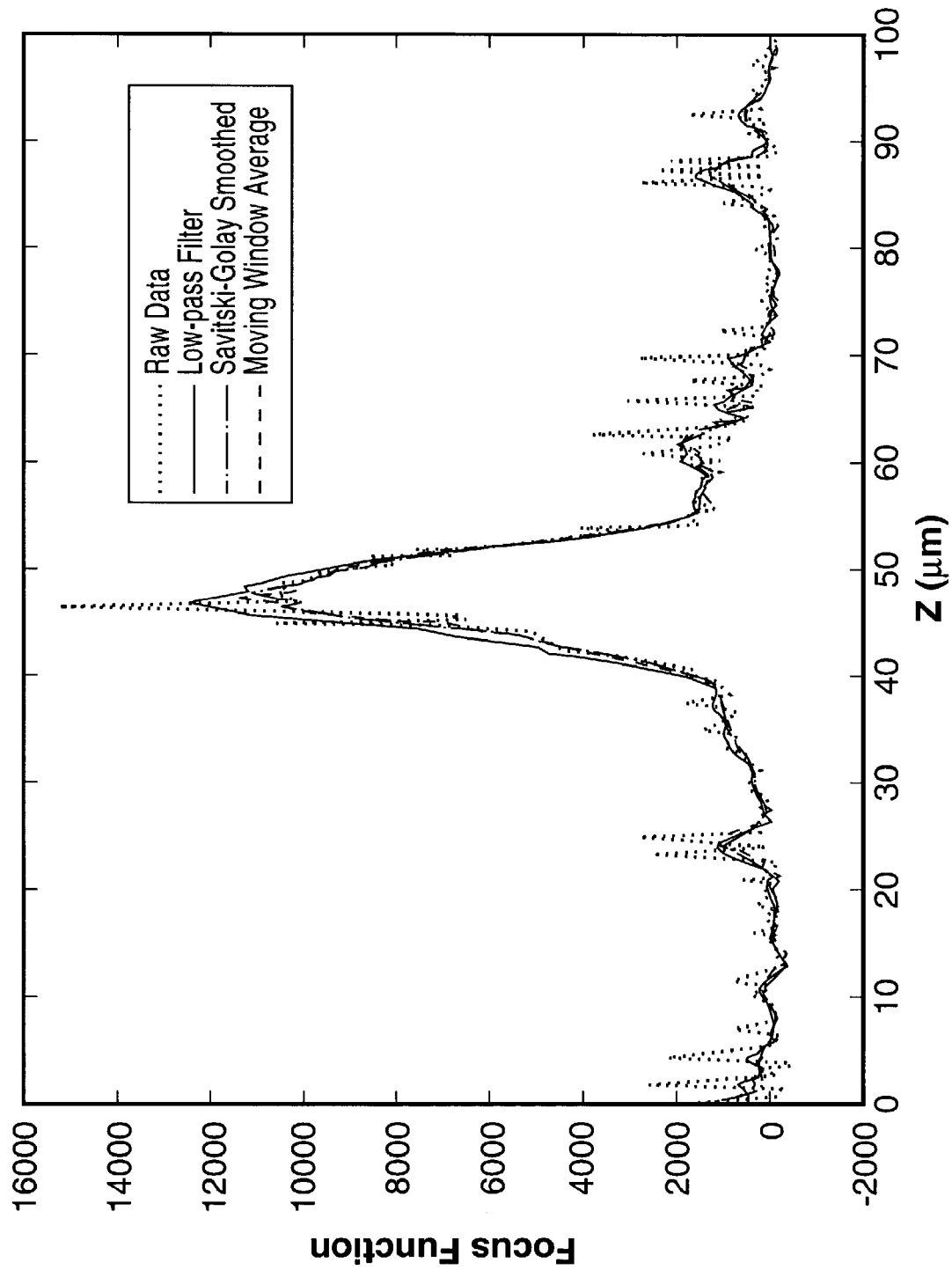
FIG. 20 is a plot of raw data compared with various filtering according to aspect of the present invention.

FIG. 20 represents focusing based on raw data in comparison to smoothed focus function curves for a typical field-of-view in a 15 μm section of hamster liver. After the data were filtered, tests to automatically identify the surface boundaries were designed. It is assumed that in this experimental setup, the focus function behaves somewhat like a sinusoidal function over half a period. When the image plane is outside the tissue thickness or the image is out of focus, the focus function is zero or small. Image intensity then increases as the "top" of the section is approached. As image content increases, as one focuses closer through the specimen, so does the focus function until a plateau is reached, after which image content decreases and tapers off as the microscope objective is moved past the "bottom" of the tissue.

In spectrometry, one measure of optical resolution is the full-width at half-maximum. The full-width at half-maximum is commonly used to describe the width of a pulse or function, so that criterion is also used on the focus function curve to determine a top and bottom tissue surface. The boundary between the slide and the tissue may be modeled as a step change in index of refraction. The properties of a Fourier series approximation of a step function motivate the use of a second derivative test to identify the top and bottom. Therefore, the location of the tissue boundary is considered to be at the inflection point.

Figure 21:
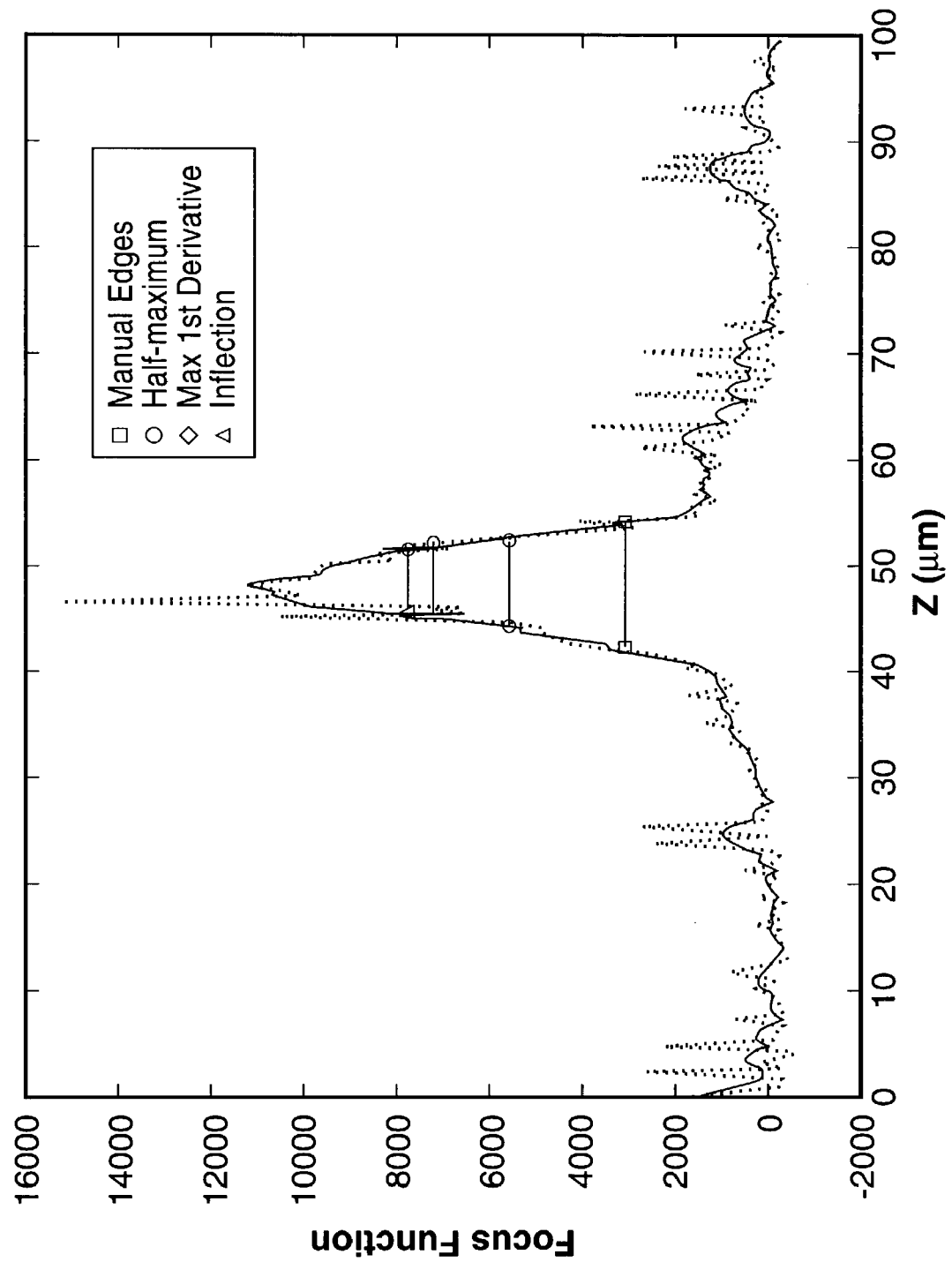
FIG. 21 is a plot of boundary locations identified by automated methods according to aspects of the present invention.

FIG. 21 provides a comparison of boundary locations identified by the automated methods with manually identified boundaries. The result of Savitzky-Golay filtering the focus function is shown for the same field-of-view as in FIG. 20, superimposed over the raw data.

Using the manually identified boundaries as references for the true tissue boundaries, the automatic methods tended to choose locations still considered inside the section for the top and bottom surfaces. Ideally, the automatic methods would select boundaries outside the true boundaries. The imaging of additional empty fields outside the tissue section helps during image processing with three-dimensional convolution filters.

To compensate for surface location errors a priori information of the tissue section's thickness was included in determining the top and bottom boundaries. Essentially, the estimates of the surface locations would be corrected outward by a certain fraction of the thickness of the specimen. To quantify the effects of the ad hoc adjustment, a confidence level is defined wherein the number of inclusions is compared to the total number of top and bottom surfaces in a given data set. An inclusion is defined, for the top surface, when the estimated axial position is less than the manually identified position. For the bottom surface, an inclusion is when the estimated axial position is greater than the manually identified position.

FIG. 22, FIG. 23, and FIG. 24 depict the variation in confidence levels for each automated method comprising half-maximum (FIG. 22), maximum first derivative (FIG. 23), inflection point (FIG. 24), as the amount of correction for each of the top and bottom locations is increased. When no correction is applied, the confidence levels for the automated methods are very low, and seen at or below 10%. Confidence levels increase as the amount of correction increases and the estimated tissue boundaries are pushed further out. Essentially the entire tissue section is included when the fraction of thickness compensated for both the top and bottom boundaries comprises a given fraction of the thickness equal to about 0.5. Stated another way, to provide high confidence it is generally necessary to collect images through a distance that is two times the thickness of a tissue specimen.

Figure 25:
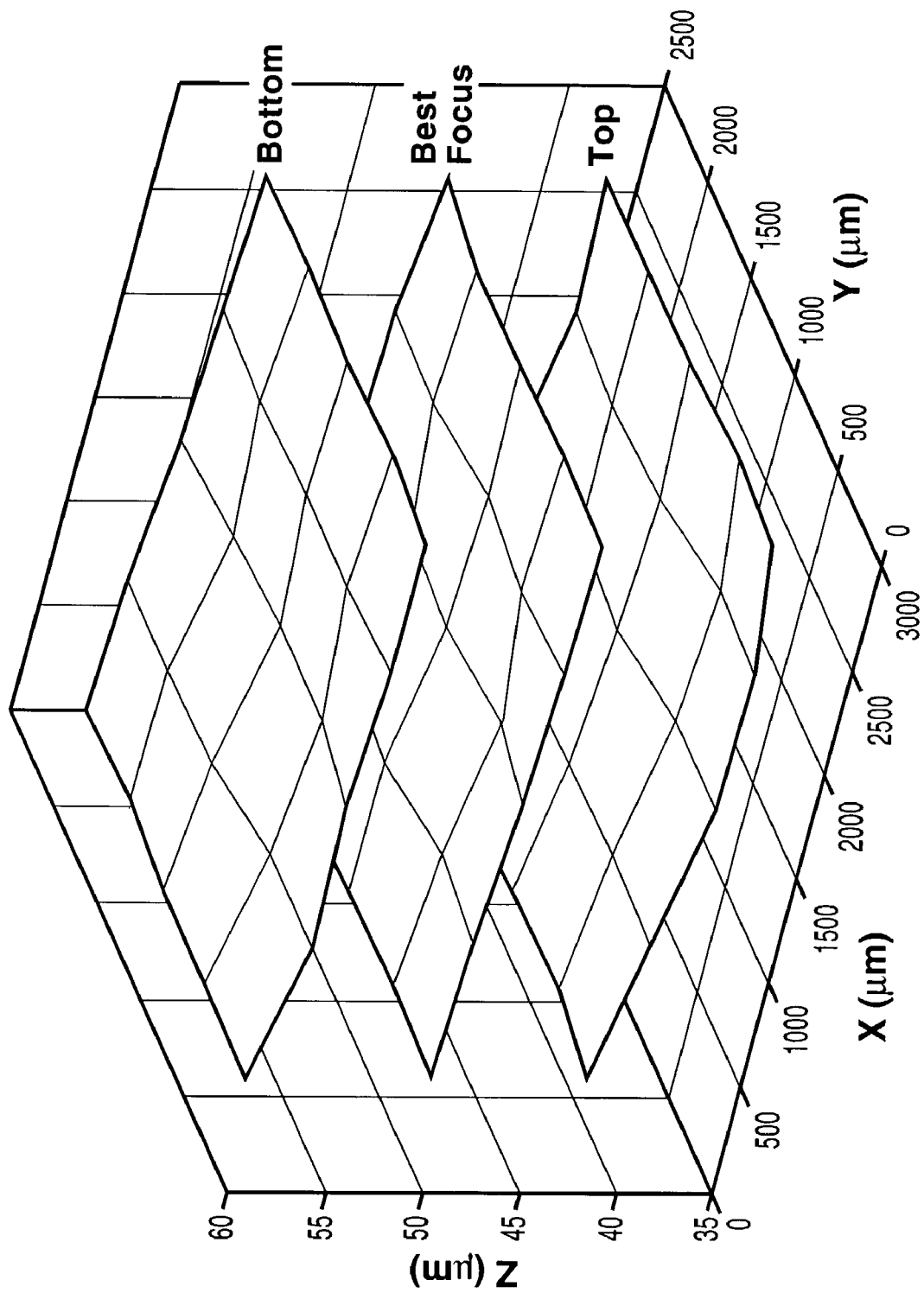
FIG. 25 is a plot of surface locations for the top and bottom along with best focus determined by detection methods according to aspects of the present invention.

FIG. 25 illustrates surface locations for the top, best focus, and bottom planes of a 15 µm (nominal) hamster liver section, in which each point in the mesh represents a single field of view. The best focus can be seen in the plot to lie intermediate the upper and lower surfaces.

7. Least Squares Contrast-Enhancing FIR Filters.

Confocal cell images often have low contrast due to both inherently low signal-to-noise ratios and high cell-cell contrast ratios that can occupy much of the available imaging dynamic range. Most current segmentation techniques designed to meet these challenges are iterative and/or require operator intervention.

A contrast-enhancing technique previously developed for 2D images of fluorescent cell nuclei was extended for 3D confocal images (stacks of 2D image slices) to enable fast single-step segmentation. Edge sharpening and contrast-enhancement were achieved by filtering with an FIR filter. Optimal FIR filters ranging in size from 3×3×3 to 13×13×13 were designed by utilizing the perceptron criterion and nonlinear least squares on confocal training datasets derived from fluorescent microbeads. The advantage of beads With known shapes and sizes is that the ideal (or standard) segmented image is known a priori. Design of 3D FIR filters is computationally intensive and parallel processing algorithms were developed to achieve practical speed.

Parallel processing with fourteen CPUs reduced the processing time for designing a 13×13×13 filter from 21.9 days to 2.4 days. Filters designed via the perceptron criterion dramatically enhanced the contrast of 3D images of beads and DAPI-stained NIH 3T3 and bovine cartilage cell nuclei. Surface-rendered images of DAPI-stained cell nuclei further demonstrated enhanced detail.

The results achieved, therefore, support the hypothesis that this technique provides accurate segmentation of 3D images.

Three-dimensional microscopes facilitate observation of biological specimens through techniques that generate high axial resolution. Multiphoton fluorescence and confocal microscopy both allow for more truthful visualization of single cells, groups of cells, or entire tissue sections than either 2D microscopy or serial sectioning. In a 3D microscopy Z-series, the entire specimen volume is recorded and represented in a 3D array of volume picture elements, or voxels. Size and volume measurements from this 3D data are more accurate than with estimates from 2D images. The 3D nature of the data enables direct observation of structural relationships in tissues, measurement and analyses of cells that would as individuals normally be grouped by overlapping in 2D image projections, and accurate reconstruction of higher level cellular relationships in native tissue. On the other hand, slow speed coupled with limited automation and demands for large data storage, management, and processing have traditionally limited 3D microscopy to relatively qualitative observations of a few cells at a time as compared with flow cytometers and recent 2D image cytometers.

Advances in high-speed confocal microscopy, data storage, and computational power, aspects of which are described herein, are overcoming some of these limitations and are paving the way for practical 3D cytometry. The single-spot laser scanning technique most commonly employed in confocal and multiphoton systems has fundamentally hampered signal-to-noise ratios (SNRs) at high acquisition rates, such as optical sectioning at or above thirty Hertz. Parallel systems, creating tens to tens of thousands of spots arrayed simultaneously on a specimen, offer orders of magnitude higher combinations of sensitivity and speed than single-spot scanning. Parallel 3D microscopy techniques are based on variations of the Nipkow disk, spatial light modulators such as the Texas Instruments Digital Light Processor (DLP) and multifocal multiphoton microscopy. These parallel techniques are capable of providing high-resolution optical sections rates of 10-1000 Hz with orders of magnitude greater SNRs single-spot scanning laser confocal microscopes. The cost of hard-drive based storage has dropped faster than computing power for the last several years. The development of larger capacity, higher data transfer rates, and lower manufacturing costs have reduced the cost of hard-drive based storage to where the storing of terabyte quantities is now practical. In addition, competition between microprocessor manufactures and the development of new manufacturing techniques have reduced the cost of various processing resources, such as the x86 family processors and DSP chips. The advances in these three areas will simplify and lower the cost of fully automated 3D cytometers to allow utilization in a wide range of research and clinical applications.

For 3D cytometry to achieve the ubiquitous use of a flow cytometer or become practical from the point of view of say a pathologist analyzing tens to thousands of tissue sections per day, high-speed acquisition must be combined with walk-away automation. Automated 3D cytometry requires unattended scanning and reassembly of many 3D fields-of-view, mechanized tracking of laterally undulating tissue sections, and accurate segmentation of 3D cell images.

Accurate and fast 3D segmentation is an important and challenging step toward providing "walk-away" automation. Image segmentation creates a data structure of binary masks that locate the image points (pixels or voxels) describing each object. Segmenting the image: (1) is the first step in making cell measurements; (2) enables the data reduction option of storing only the regions of interest (ROIs) containing the cell images, which has proven useful in 2D cytometry and may be even more critical for handling massive 3D images; and (3) provides the basis for rapid image-to-data and data-to-image relational database operations critical for intelligent and fast gating, sorting and visualization of cell types. Segmentation of biological microscope images is difficult because cells are amorphous in size and shape, and various subcellular regions often differ dramatically in intensity, creating images that occupy essentially the entire dynamic range. The task of analyzing even a small tissue section may involve processing and measuring millions of cells and demands real-time computation. In addition, regardless of the ongoing imaging sensitivity and dynamic range improvements, the motivation to provide faster imaging generally gives a substantial advantage to the segmentation that performs most robustly and accurately even on low signal-to-noise (SNR) images.

The difficulty in segmenting microscope images has limited most techniques to highly iterative techniques that are not well suited for real-time operation and/or require operator assistance. In previously developed 2D segmentation, a key to providing segmentation was found in performing contrast enhancement achieved through convolution of the raw image data with an FIR filter designed by supervised nonlinear least squares. This FIR filter boosts the intensities of the foreground object pixels while suppressing the intensities of the background pixels. In 2D operation, the filter stretches the contrast to enable automatic global thresholding. For image G, FIR filter K, and image segment S, the segmentation operations were described previously in Eq. 1. The operations within Eq. 1 represent a two-class linear classifier with class separation enhanced by an FIR filter. Given an image G and the corresponding ideally segmented image $I_S$, the FIR filter is designed so that it best maps G into $I_S$. The objective of the filter design is to minimize the pixel-to-pixel error between the ideal image $I_S$ and the filtered image F. The perceptron criterion, commonly used in neural network and other classification techniques, is the error measure for filter design, as described previously in Eq. 2, in which the error E is non-zero only when the filtered image F has not achieved the contrast enhancement defined by [A,B]. Minimization of E produces the filter K that creates the best contrast for subsequent threshold within [A,B]. Relaxing the requirement that background and object pixels achieve an exact value (i.e., 0 and 255 respectively for 8-bit fluorescence images) by defining zero error outside [A,B] was found to dramatically improve the resulting contrast in the previous 2D segmentation work. With the contrast enhancement provided by this filter, the subsequent thresholding step was automatic and non-iterative in 2D and may achieve similarly simple operation in 3D.

The supervised portion of this filter design technique was labor-intensive in 2D and similar manual delineation of the surfaces of nuclei in 3D images would have been more challenging. Therefore, in addition to extending this technique to 3D, spherical fluorescence beads of known size were introduced to provide a priori knowledge of the ideal segment. Use of standard objects in 2D was not thought practical largely because known specimens thin enough to fit within the depth of field of high-resolution optics are not widely available; beads of sufficient area to mimic cell objects also extend axially outside the depth of field and generate blurry images. With these modifications, we present preliminary evaluation of 3D least squares filter design for segmentation of fluorescent confocal images of cell nuclei.

Fluorescent micro-beads embedded in pulverized mouse liver tissue were used to simulate cells in biological tissue. Knowledge of the bead dimensions and the conditions under which the data was obtained allowed for precise definition of the ideal data in the filter design process. For each microscope slide, a mouse liver tissue weighting approximately 0.5 g was pulverized with a mortar and pestle into a paste. One hundred fifty micro-liters of unfixed liver paste were deposited onto a well-slide (i.e. Part No. 12-560A from Fisher Research® of Pittsburgh, Pa.). Five micro-liters of 4 μm and 10 μm diameter fluorescent micro-beads (i.e. Part No. F-8834 with excitation peak at 580 nm and emission peak 605 nm from Molecular Probes Inc.® of Eugene, Oreg.) were then injected and mixed into the liver solution with the pipette tip. The fluorescent bead solution was sonicated prior to use to create a uniform slurry. The preparation was then fixed with 90% ethanol, covered with a coverslip, and sealed with nail polish.

The 3D images were acquired through Fluor 20×Ph3DL 0.75 NA, Fluor 40×Ph3DL 0.85 NA and PlanApo 60×1.4 NA oil objectives (Nikon Instruments Inc.® of Melville, N.Y.) with a Bio-Rad® model MRC-1024UV laser scanning confocal system (Bio-Rad Laboratories®, Hercules, Calif.) attached to a Nikon Diaphot 300 inverted microscope. For each data set, a Z-series was collected that contains the entire bead and several empty slices at the top and bottom of the stack. At each axial position in the Z-series, 100 images were collected. One of each of the 100 images was extracted to create the input Z-series (G in equation 1). Each set of 100 optical sections was then averaged to create a low SNR Z-series. A new Z-series $I_S$ was then artificially constructed from the centroids of the averaged experimental Z-series, the known radii of the beads and the magnification of the system. The magnification was measured with a stage micrometer (i.e. Nikon Instruments Inc., Melville, N.Y.). The stack dimensions were 64×64×36, 152×152×48, and 256×256×64 at sampling frequencies of 0.24×0.24×0.9 μm³, 0.19×0.19×0.5 μm³, and 0.13×0.13×0.2 μm³ for 20×, 40×, and 60× magnifications, respectively, with each stack comprising one bead. The procedure, equipment, and dimensions recited above being given by way of illustrative example, and not by way of a limitation on practice of the invention.

Solving for the FIR filter utilized the Levenberg-Marquardt nonlinear least-squares routine to design 3×3×3 to 13×13×13 FIR filters by minimizing the error of Eq. 2. The filter coefficients were initially set to zero. Error minimization was stopped when the improvement was less than one percent and it had decreased in the previous seven iterations. Empirically, seven successive improvements ensured convergence. Under these conditions, ten to twenty iterations were required to design the filters. For comparison, linear least squares solutions were also found by forcing foreground pixels to 255 and background pixels to 0; equation 2 was converted to $E=\Sigma(I_S-F)^2$.

Computer implementation of the technique is particularly well suited for parallel processing as nonlinear least squares design of 3D FIR filters is computationally intensive. Solving for 2197 (13×13×13) coefficients of the filter using a 256×256×64 dataset on a conventional desktop PC takes weeks to complete. Filter design, therefore, has been sped-up by parallel implementation of the algorithm on a virtual parallel computer made up of fourteen Intel-based workstations, ranging from a Pentium Pro 200 MHz to Pentium III 733 MHz. It will be appreciated that a number of parallel processing platforms having any desired number of processing elements connected in a desired parallel processing arrangement may be alternatively utilized without departing from the teachings of the present invention. The processors in these workstations were configured into nodes linked together by the network interface cards (NIC) via a network. The message passing interface (i.e. MPICH from Argonne National Laboratory® in Argonne, Ill.) provided communication and synchronization between the multiple processing nodes. The virtual parallel computer was set up in a master-slave configuration. The master node was responsible for checking the status of the slave nodes, distributing the work, collecting and compiling results, and optimizing work distribution to processors of different speeds. During each iteration, the master divided the data into segments and assigned each node one data segment at a time. As each node completed a data segment, it reported the results to the master node and began work on a new segment of the data. This task distribution scheme allowed the workload to be distributed in proportional to processing speed; faster nodes being expected to accomplished more that slower nodes. To minimize data transfer bottlenecks, each node was capable of retrieving the entire dataset, which for this example was stored at each given node. During filter design, the master sent the filter coefficients and the two endpoints of each work segment and each slave node sent back the curvature matrix and the beta vector at completion of a data segment.

An example of cell staining with image segmentation and visualization utilized DAPI stained NIH 3T3 mouse fibroblasts (i.e. ATCC CRL 1658) which were cultured at 37° C. on #1.5 22×60 mm$^2$ washed and autoclaved coverslips in 5% $CO_2$ and Minimal Essential Medium with Earle's salts, 10% fetal bovine serum, 100 g/ml gentamicin, and 0.26 mg/ml L-glutamine for several days prior to fixation and staining to create an evenly distributed monolayer. These samples were then fixed for two hours in 95% ethanol and air-dried. The slides were stained for two hours with a 4',6-diamidino-2-phenylindole dihydrochloride (DAPI) nuclear stain solution consisting of 100 ng/ml DAPI, 10 mM Tris, 10 mM EDTA, 100 mM NaCl, and 2% 2-mercaptoethanol. The coverslips were then laid down on cleaned microscope slides with excess DAPI solution, and sealed with nail polish. The above process and solutions being provided by way of example and not of limitation.

In a study of DAPI-stained bovine calf cartilage tissue, knee joint cartilage tissue was harvested from a three-week old bovine calf. The cartilage tissue was sectioned into 2×5× 0.2 mm$^3$ blocks. These were fixed with 4% paraformaldehyde for one day and stained with previously described DAPI solution for four days. These blocks were mounted on microscope slides with mounting medium containing DAPI (i.e. Vectashield H-1200 from Vector Laboratories® of Burlingame, Calif.) and sealed with nail polish.

In performing the imaging, processing, and visualization, the Z-series of the nuclei were collected from the two specimens and processed to subjectively evaluate the contrast enhancement of filters designed on beads. Each contrast-enhanced Z-series was converted to a binary image by thresholding with the first minimum in the histogram after the background peak. For visualization, stereo pair images were created using a confocal imaging application, such as Confocal Assistant version 4.02 from Todd Clark Brelje from the University of Minnesota, Minn., and 3D surface renderings of the segmented regions were created, such as in MATLAB Release 12.1 from Mathworks® of Natick, Mass. The raw Z-series' were thresholded and surface rendered the same way for visual comparison.

From these experiments one can begin to visualize the potential for 3D image segmentation by least squares designed 3D FIR filters. The report includes measurements of the advantages of distributed processing and an evaluation of the appearance of the resulting contrast-enhanced images and segments.

It will be appreciated that the performance achieved with parallel processing can be task-dependent and typically scales only partially in response to the number of processors utilized due to interprocessor communication latencies and the additional computation required to reassemble the distributed results.

Figure 26:
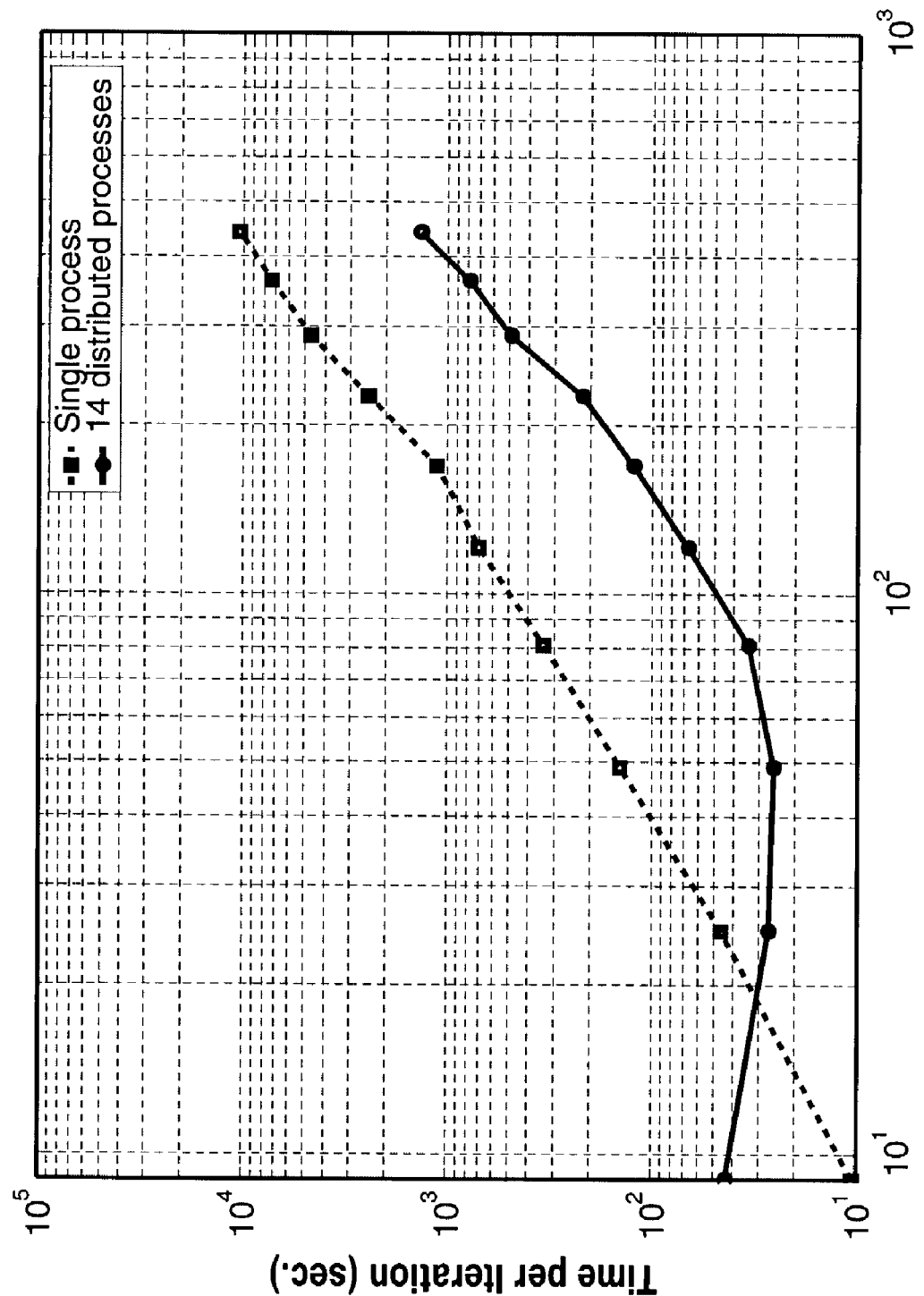
FIG. 26 is a plot of processing time in response to the number of filter coefficients utilized comparing single processor execution and multiple processor execution according to an aspect of the present invention.

FIG. 26 depicts processing time comparisons between a single-processor and fourteen processors when performing the least squares design of filters ranging in size from 27 to 2197 coefficients and a 152×152×48 image. The figure shows a processing time comparison of Levenberg-Marquardt nonlinear least squares method for the design of contrast-enhancing FIR filters of sizes 3×3×3 to 13×13×13 on a $1.1 \times 10^6$-voxel dataset (152×152×48-voxel image). Computational speed improved about an order of magnitude when utilizing greater than 729 coefficients. However, additional communication and network latency was found to outweigh the benefit of parallel processing on lower numbers of coefficients. By way of example the single-processor tests were performed on a Pentium III 533 MHz CPU, while the parallel-processor tests were performed on fourteen processors ranging from a Pentium Pro 200 MHz to Pentium III 733 MHz.

The processing time is actually longer under parallel processing when less than 125 filter coefficients are considered although the parallel processing advantage increases to about an order of magnitude (10-fold) at 729 coefficients. This order of magnitude speed advantage is consistently maintained up through the 13×13×13 filter with 2197 coefficients. As is typical, the speed increases shown in FIG. 26 are less than might be thought possible from simply multiplying by the number of processors, in response to the additional overhead and communication latencies incurred. The effects of additional overhead are especially apparent in the case of small FIR kernels for which the extra overhead dominates. Early results indicated that filters of at least 9×9×9 were needed to perform good contrast enhancement.

On a single processor, filters from 9×9×9 to 13×13×13 required 4.6 and 21.9 days, respectively. Thus, the ten-fold speed gain realized by combining fourteen CPUs to create this virtual multi-processing computer proved to substantially reduce the execution time.

Figure 27:
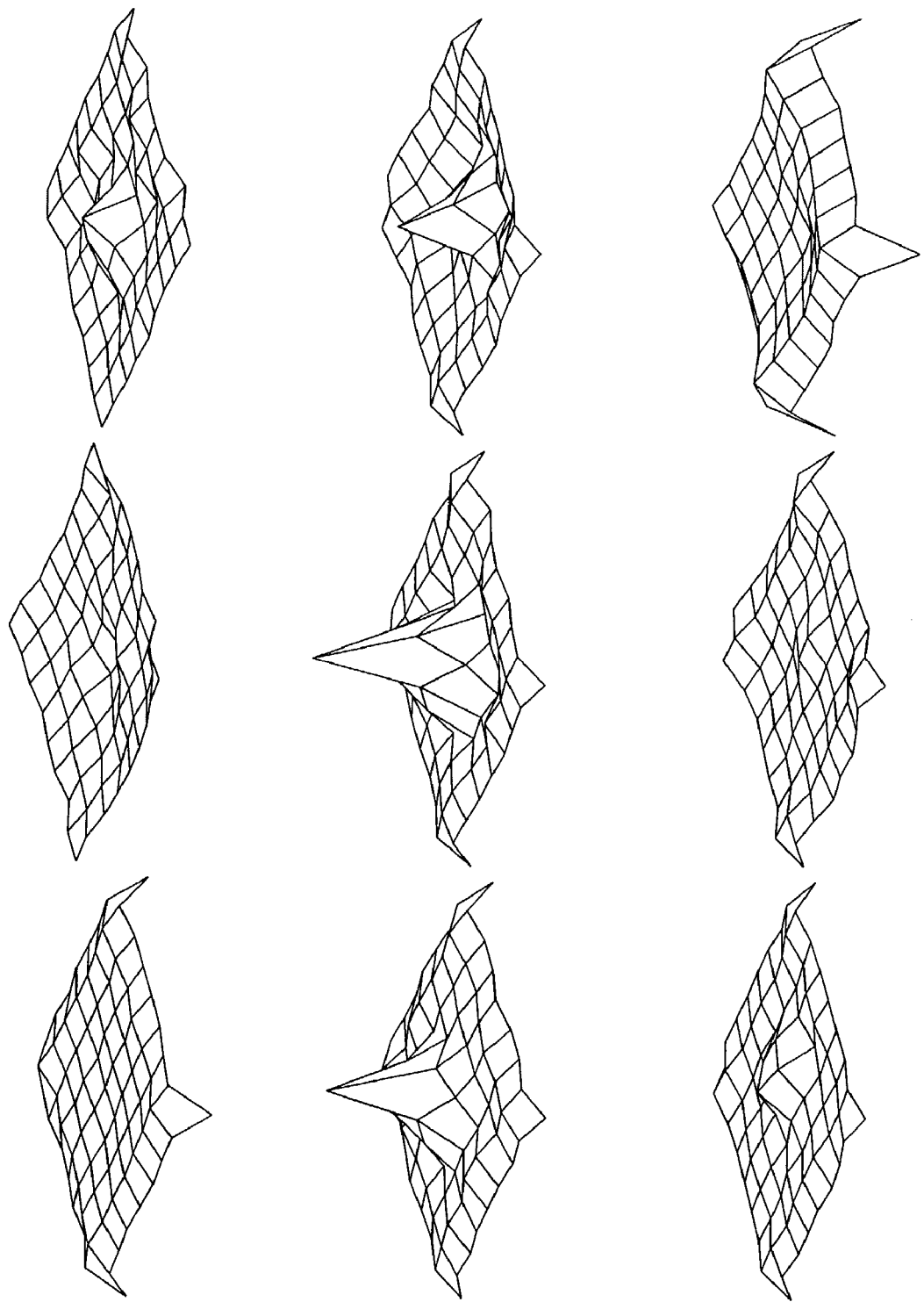
FIG. 27 is a plot of least squares FIR filters designed according to an aspect of the present invention, showing top layers (top), middle layers (middle), and bottom layers (bottom).

FIG. 27 illustrates mesh plots exemplifying a 9×9×9 nonlinear least squares designed FIR filter, whose coefficients are listed in Table 5. Within the mesh plot layers 1-3 are shown on the top, layers 4-6 are shown on the middle, and layers 7-9 are shown on the bottom. The FIR filter has some characteristics analogous to a sharpening filter.

Considerations of linear fit in relation to a nonlinear fit (perceptron criterion) are not described. The computational requirement for an exact fit to the ideal image segment is dramatically less than for the perceptron-defined error of Eq. 2 because it is solved by single-step linear least squares. The difference between the contrast-enhancement provided by linearly and nonlinearly designed 7×7×7 filters was compared to evaluate the need for the extra computation.

Figure 28:
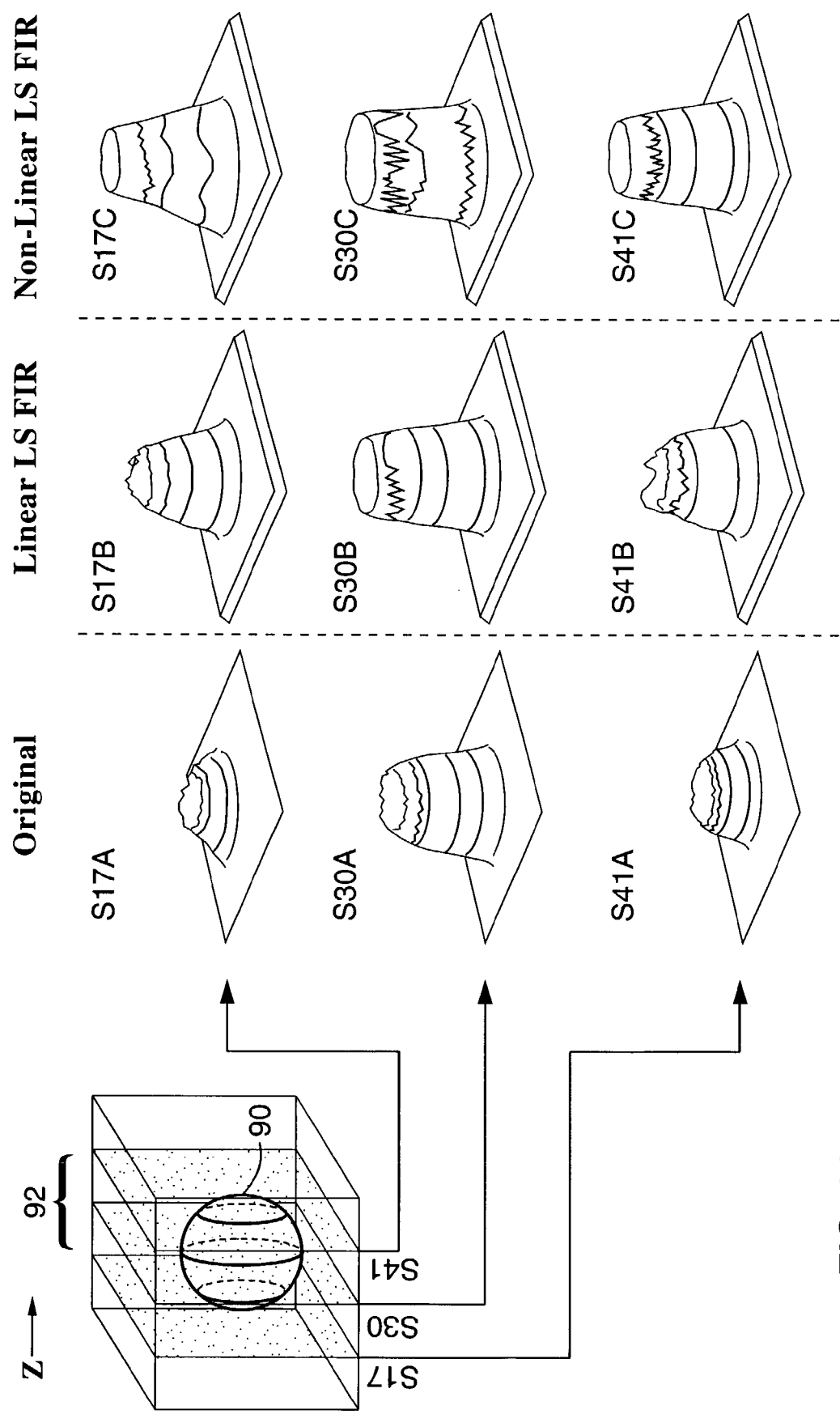
FIG. 28 are mesh plots of intensity of three optical sections of a 4 μm diameter fluorescent bead according to an aspect of the present invention, shown taken at sections 17, 30, and 41.
Figure 29A:
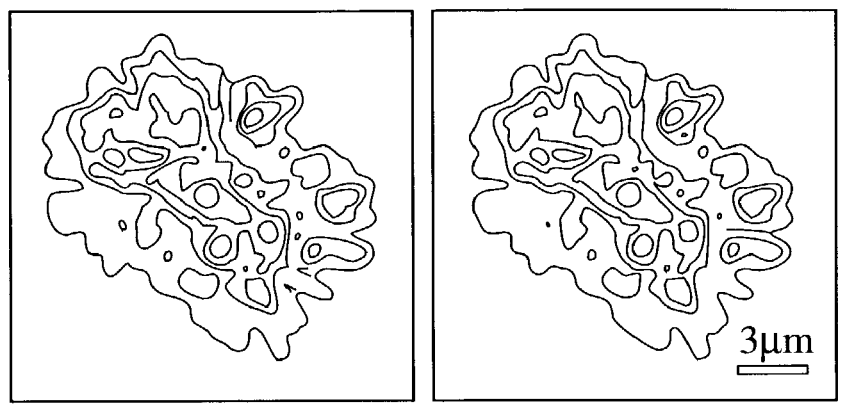
FIG. 29A-29D are stereo image pair representations of a DAPI stained mitotic nucleus to which image filtering is applied according to an aspect of the present invention.
Figure 29B:
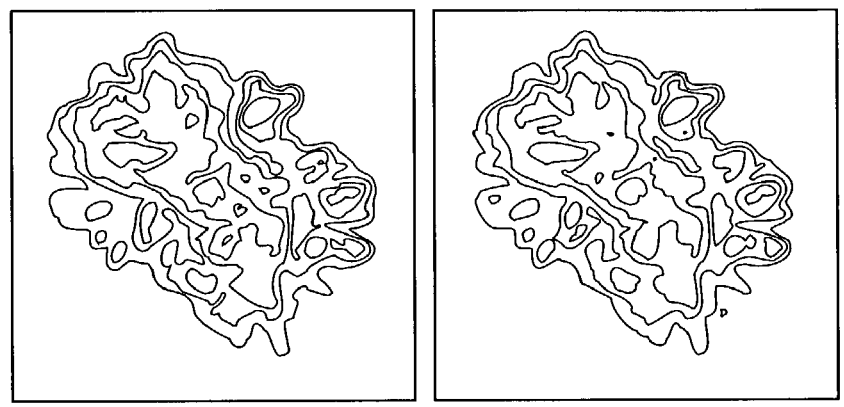
Figure 29C:
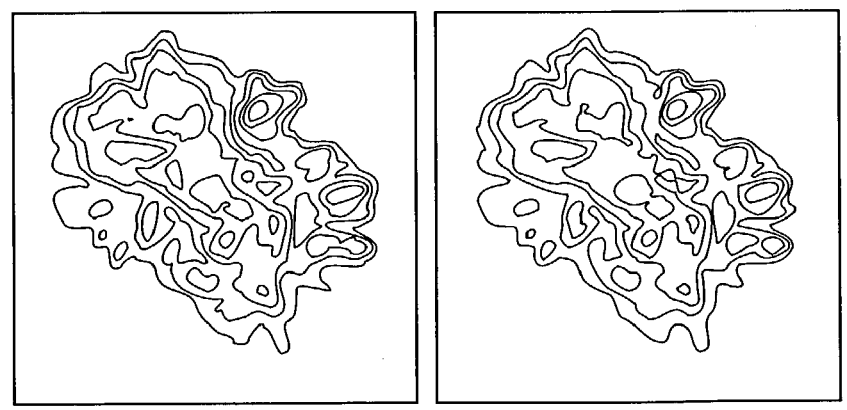
Figure 29D:
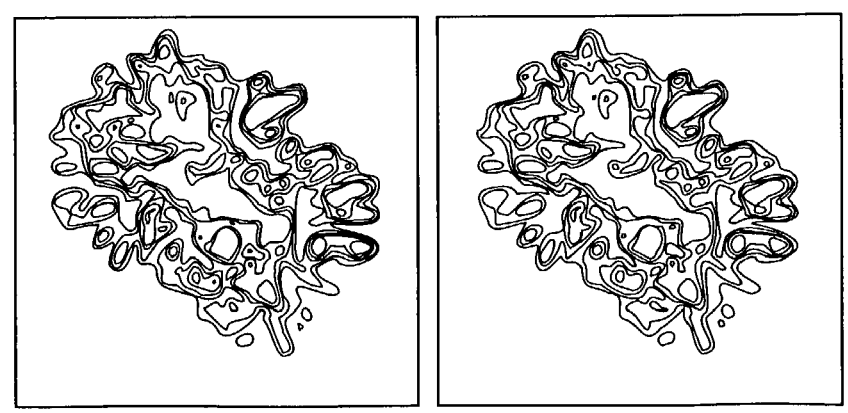

FIG. 28 depicts three dimensional mesh plots of selected optical sections from the original and filtered versions of the confocal image of a 4 μm fluorescent bead 90 imaged with three sections 92 being shown for simplicity comprising S17, S30, S41. The intensity mesh plots of the figure show optical sections {17, 30 and 41} from a 55×53×55-voxel image of a 4 μm diameter fluorescent bead. The "A" images (17A, 30A, 41A) are the original images, with the "B" images being results from a 7×7×7 linearly designed exact fit filter, while the "C" images are the results from a 7×7×7 nonlinearly designed classifier fit filter. Plots for "B" and "C" images were clipped at 0, 255 to magnify the threshold region and the optical sections in the original images "A" were acquired within the eight-bit dynamic range. The image stack was acquired on a Bio-Rad model MRC-1024 Confocal Microscope with a 60×1.4 NA Nikon objective at 0.2×0.2×0.2 μm$^3$ sampling.

The contrast is visibly improved in the mesh plots of optical sections from both the linearly- and nonlinearly-designed FIR filters (shown in the columns B and C, respectively), as compared to the mesh plots of the original images in column A. The contrast enhancement of the filter designed by nonlinear least squares is also better than that of the linear least squares filter, which is particularly visible in the optical sections 17 and 41 near the top and bottom of the bead. The improvement in contrast by the nonlinearly designed filter is similar to that observed for 2D image segmentation in the earlier study. Thus, the advantage gained by the iterative nonlinear filter design is valuable.

Filters designed according to Eq. 1 and Eq. 2 were applied to confocal images of cell nuclei stained with DAPI to visualize the contrast enhancement. For comparison, regular 2D sharpening and unsharp-mask filters were also applied to each layer of the dataset.

FIG. 29A through FIG. 29D depict projections/stereo pairs of the original and filtered Z-series' of a metaphase nucleus. (The figure contains line draw renderings made of captured images). The figure depicts stereo-pairs of a DAPI stained mitotic nucleus, with FIG. 29A of the original, FIG. 29B of the 3×3 sharpening filter, FIG. 29C of the 3×3 unsharp-masking filter, and FIG. 29D in which contrast is enhanced with a 9×9×9 nonlinearly designed filter. In the sharpening and unsharp-masking versions, contrast is slightly improved and noise is also amplified. On the other hand, in the contrast enhanced version with nonlinearly designed filter the edges are much better defined and both dim and bright regions exhibit more detail; some of the dim chromosome arms are much more clearly defined after filtering while noise is not significantly increased. The image was collected on a Bio-Rad model MRC-1024 Confocal Microscope with a 60×1.4 NA Nikon objective at 0.1×0.1×0.2 μm$^3$ sampling, while the stereo pairs were created with 0° and 15° views.

The image enhanced with the nonlinear least squares designed filter demonstrates the largest contrast enhancement in which the details of the chromosome arms are much more clearly delineated. Note that although the edges of the chromosomes appear sharper, the noise in this filtered image appears substantially less than the other two filtered images, indicating that the filters designed by this method reduce the apparent noise in addition to their advantages of image sharpening. It should be noted that both the brighter and dimmer portions of the nucleus show increased detail and contrast, indicating successful achievement of the goal of improving contrast for the purpose of simpler single-threshold segmentation.

Figure 30A:
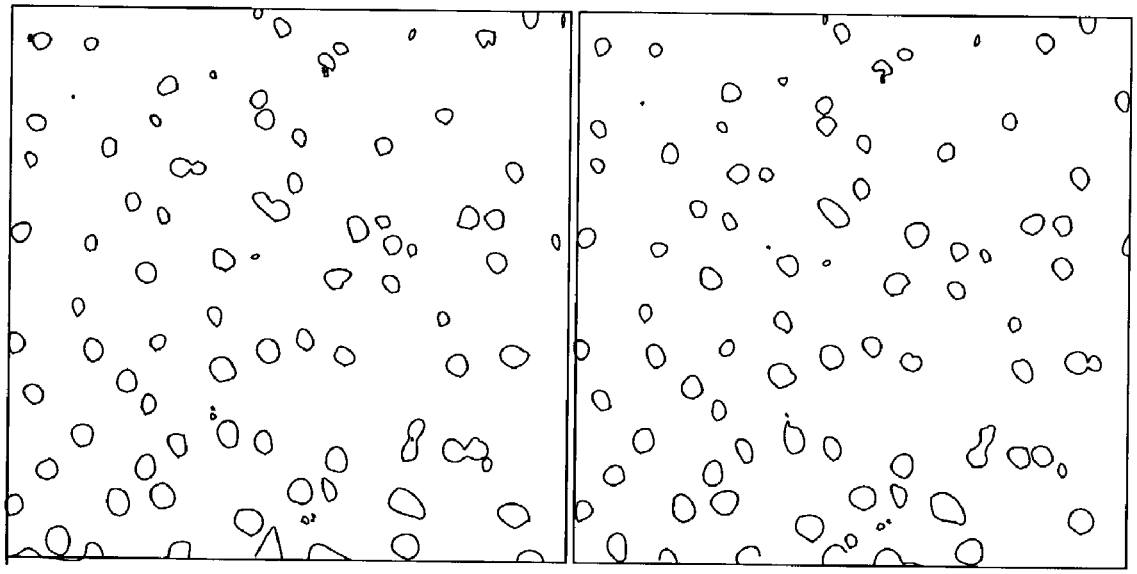
FIGS. 30A, 30B are stereo image pair representations of DAPI stained bovine cartilage tissue which have been imaged directly (raw) and after image enhancement according to aspects of the present invention.
Figure 30B:
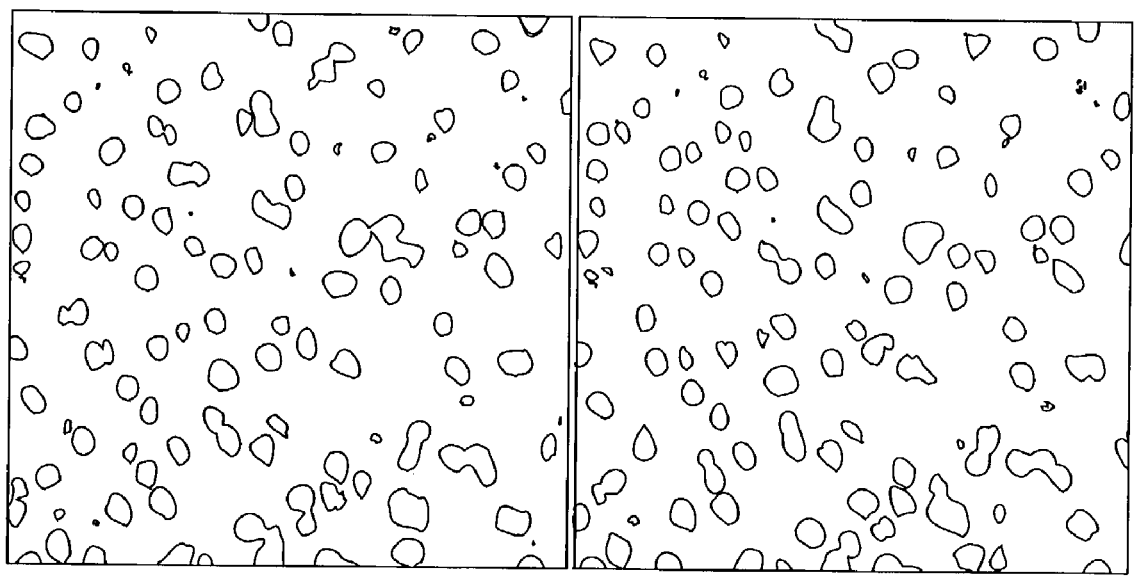

FIG. 30A and FIG. 30B illustrate examples of stereo image pairs of a 163 μm thick bovine cartilage tissue which shows similar results, in which the contrast was enhanced, saturating most cell nuclei (at a digital intensity of 255) without increasing the noise. FIG. 30A is a stereo-pair-image depicting a DAPI stained bovine cartilage tissue with FIG. 30B depicting a contrast enhanced image with a 9×9×9 nonlinearly designed filter, coefficients for which are listed in Table 5. In the filtered version, the contrast was noticeably enhanced saturating most cell nuclei. The 512×512×326 voxel image was collected on a Bio-Rad model MRC-1024 Confocal Microscope with a 40×0.85 NA Nikon objective at 0.266×0.266×0.5 μm$^3$ sampling, with the stereo pairs being created from ±6° views.

Images captured of deep tissue can be very dim in confocal microscopy and the deepest cells in FIG. 30B do not appear as well enhanced. If enhancement of deep tissues is desired, then the gain may be corrected in response to depth, wherein image enhancement will be extended to a greater depth.

To more easily visualize the differences between the original and filtered images that might be expected in automated image segmentation, surfaces were rendered after thresholding. Intensity histograms of the confocal volumes were analyzed and the threshold chosen as the first minimum after the largest (background intensity) peak for both filtered and unfiltered images.

Figure 31A:
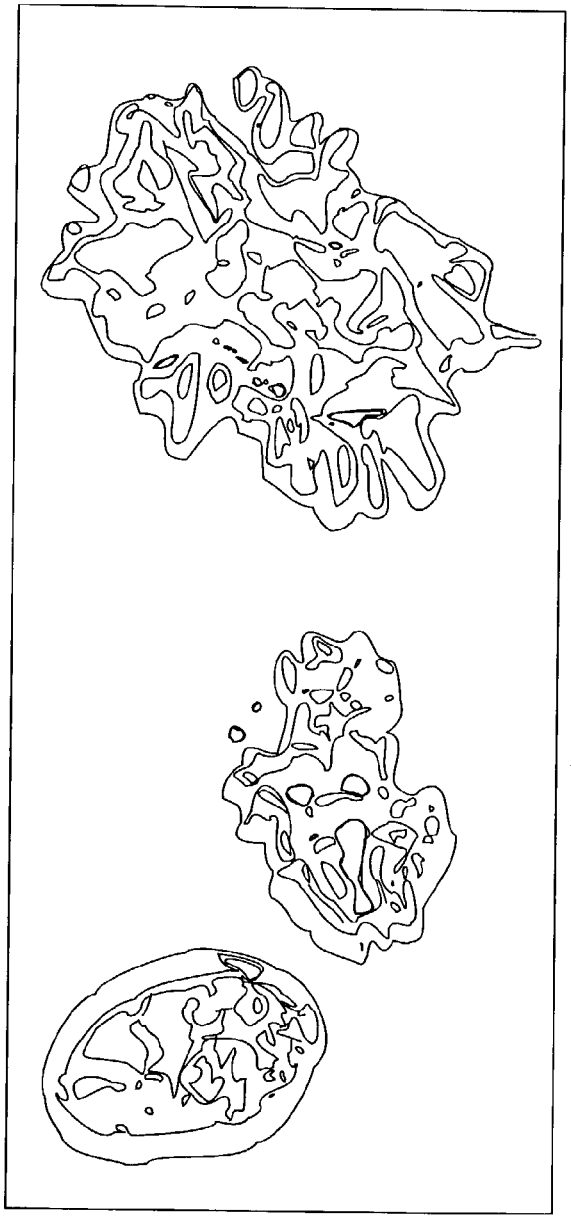
FIGS. 31A, 31B are surface image representations of three nuclei which have been imaged directly (raw) and after image enhancement according to an aspect of the present invention.
Figure 31B:
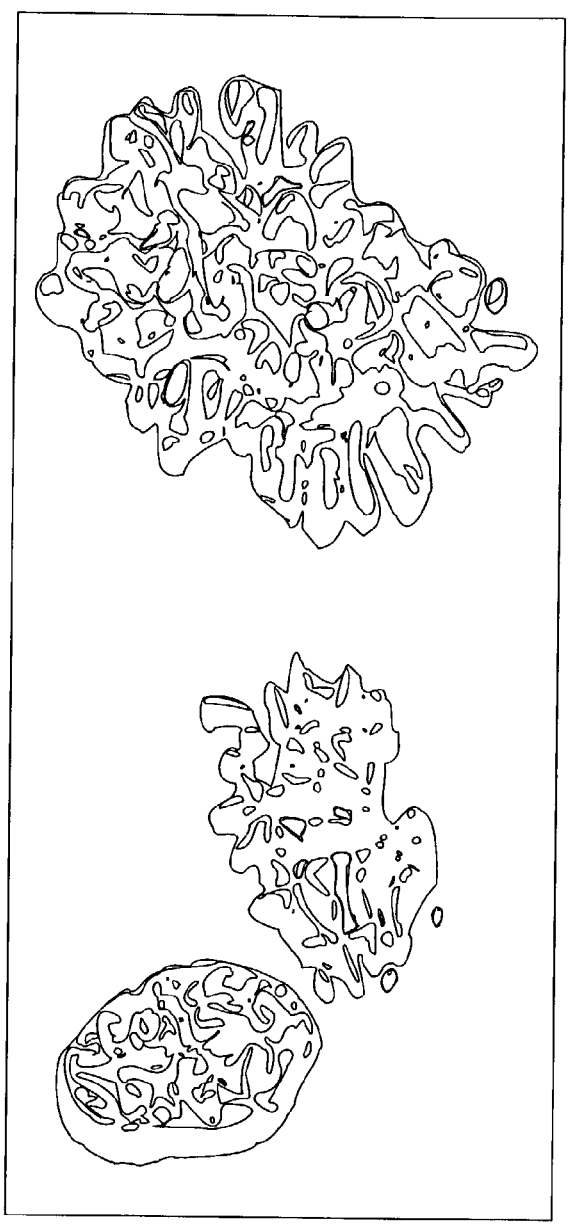

FIGS. 31A and 31B depict a comparison between surface renderings of the resulting segmented original and filtered Z-series' of three nuclei stained with DAPI. Surface renderings of three nuclei from the raw data are shown in FIG. 31A and contrast-enhancing filtered images are shown in FIG. 31B. The data associated with both sets of renditions were thresholded using the first minimum after the largest (background) peak in the intensity histogram. The nuclei shown in FIG. 31B show increased surface detail in relation to those of FIG. 31A. By appearance, underselected regions (from dim portions of the image) on FIG. 31A are more appropriately represented within FIG. 31B and overselected regions (from bright portions) within FIG. 31A are exhibited with more detail in FIG. 31B.

Portions of the original images contain dim regions that were underselected and bright regions that were overselected. Improvement in both underselected chromosome arms and overselected central regions can be seen in the filtered versions.

FIG. 32A and FIG. 32B shows similar results with the Z-series' of bovine cartilage tissue with surface renderings of nuclei from the raw image of a 136×136×163 μm$^3$ region of bovine cartilage tissue in FIG. 32A and after contrast-enhancement in FIG. 32B. Both sets of images were thresholded using the first minimum after the largest (background) peak in the intensity histogram. In the raw image, brighter nuclei at the top of the stack are large and appear to be overselected and dimmer ones deeper in the stack are smaller and appear to be underselected. In the enhanced image, bright overselected nuclei are smaller and show more surface details (nuclei 1-6, 9, 12, and 15) whereas dim underselected nuclei are larger (nuclei 7, 8, 11, 19-21, and 24). The remaining nuclei in the insets appear to have the same size but with much more surface details in the enhanced version. It is contemplated that a substantial portion of the size variation may be corrected utilizing gain correction techniques operating in response to depth. Small processing artifacts present in the enhanced image (e.g., the object below nuclei 16 and 17) may be easily eliminated using an object-size threshold. Brighter nuclei were overselected and dimmer nuclei were underselected in the original image. In the filtered version, all cells show much more consistent surface details, nuclei that were overselected became smaller and ones that were underselected became larger.

Figure 33:
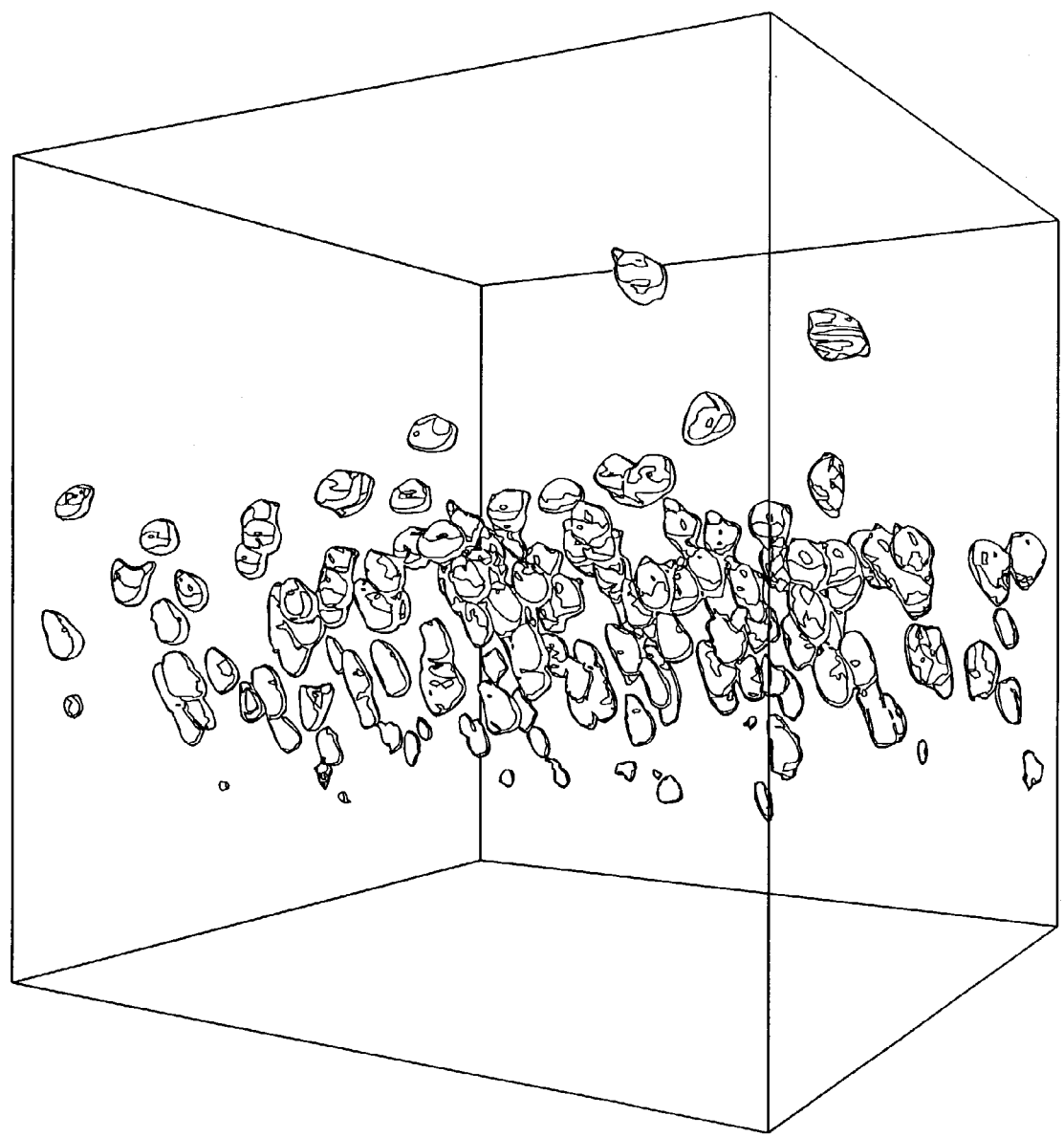
FIG. 33 is a contrast enhanced surface image representation of a plurality of nuclei with contrast-enhanced images according to an aspect of the present invention being superimposed upon the raw images.

In FIG. 33, the raw image of FIG. 32A was superimposed on the contrast enhanced image of FIG. 32B are superimposed. In a graphics system it is preferred that each image be shown in a contrasting manner so the individual contributions may be seen, for example showing the contribution from FIG. 32A in yellow and from FIG. 32B in red. The outer surfaces of the upper halves of the nuclei are predominantly result from the original image while the outer surfaces of the lower halves primarily result from the contrast-enhanced image. This may indicate that the upper portion of a nucleus is dense enough to routinely shade the lower portion in confocal microscopy.

It is also interesting to note that contrast enhancement appears to predominantly shrink the upper halves of the images and expand the lower halves of the nuclei. This is consistent with considerations of the upper portion of the object shading the lower portion. This raises the question of whether or not bright objects are routinely distorted by shading in confocal microscopy. In either case, the 3D contrast enhancement in these examples appears to substantially improve image segmentation.

This initial evaluation of nonlinearly designed 3D FIR filters demonstrated contrast enhancement that may lead to the same kind of accurate, fully automated 3D image segmentation that was observed in earlier work on 2D image segmentation. The use of fluorescent beads in constructing the ideal image segments for design of the FIR filters is important because it substantially reduces preparation time and may offer the opportunity to completely automate the process and eliminate supervision. The computational challenge in designing these filters was met by taking advantage of a ten-fold speed improvement from the use of a virtual parallel computer having fourteen processors. Real time operation of these filters on 3D images produced by fast 3D microscopy systems, such as operating at 100 Hz or above, require about 80 GOPS and can be achieved by implementation on a bank of DSP chips. In view of Moore's law, which generally describes available computer speed doubling every eighteen months, the cost of real-time implementation of the present invention should continue to drop rapidly. The results demonstrated substantial promise for real-time automated 3D image segmentation and motivate further study.

RELATED LITERATURE

The following publications are incorporated herein by reference.

1. L K Nguyen, M Bravo-Zanoguera, A L Kellner, J H Price, "Magnification Corrected Optical Image Splitting Module for Simultaneous Multiplanar Acquisition," *Proc. Of SPIE, Optical Diagnostics of Living Cells III*, 3921:31-40, 2000.
2. M Bravo-Zanoguera, B v Massenbach, J H Price, "Automatic on-the-fly focusing for continuous image acquisition in high-resolution microscopy," *SPIE Proc. Optical Diagnostics of Biological Fluids and Advanced Techniques Analytical Cytology*, San Jose, 3604:243-252, January 1999.
3. M E Bravo-Zanoguera, J H Price. "Simultaneous Multiplanar Image Acquisition in Light Microscopy," *SPIE Proc. Optical Diagnostics of Biological Fluids and Advanced Techniques Analytical Cytology* 3260, 1998.
4. J H Price, "Autofocus System for Scanning Microscopy Having a Volume Image Formation," U.S. Pat. No. 5,932,872, 41 pages, Aug. 3, 1999.
5. M E Bravo-Zanoguera, "Autofocus for High Speed Scanning in Image Cytometry," Ph.D. Dissertation, Department of Bioengineering, University of California, San Diego, 202 pages, 2001.
6. J. H. Price and D. A. Gough, "Comparison of Digital Autofocus Functions for Phase-Contrast and Fluorescence Scanning Microscopy," *Cytometry,* 16(4), 283-297, Aug. 1, 1994.
7. M E Bravo-Zanoguera, J H Price. "Analog Autofocus Circuit Design for Scanning Microscopy," *SPIE Proc. Optical Diagnostics of Biological Fluids and Advanced Techniques Analytical Cytology* 2982: 468-475, 1997.
8. M Oliva, M E Bravo-Zanoguera and J H Price. "Autofocus for phase-contrast microscopy: an investigation into the cause of nonunimodality," *SPIE Proc. Optical Diagnostics of Biological Fluids and Advanced Techniques Analytical Cytology* 3260, 1998.
9. M Oliva, M E Bravo-Zanoguera, J H Price, "Filtering out contrast reversals for microscopy autofocus," *Applied Optics, Optical Tech. & Biomed. Optics,* 38(4):638-646, 1999. Issue Cover.
10. M Bravo-Zanoguera, B von Massenbach, A L Kellner and J H Price, "High Performance Autofocus Circuit for Biological Microscopy," *Review of Scientific Instruments,* 69(11):3966-3977, 1998.
11. M Bravo-Zanoguera, J H Price, "Analog Circuit for an Autofocus Microscope System," U.S. Pat. No. 5,995,143, 15 pages, Nov. 30, 1999.
12. J H Price, D A Gough, "Autofocus System for Scanning Microscopy," U.S. Pat. No. 5,790,710, 35 pages, Aug. 4, 1998.
13. J H Price, D A Gough, "Operator Independent Image Cytometer," U.S. Pat. No. 5,548,661, Aug. 20, 1996.
14. J H Price, "Scanning Cytometry for Cell Monolayers," Ph.D. Dissertation, Applied Mechanics and Engineering Sciences, Bioengineering, University of California San Diego, 1990.
15. F Shen, J H Price, "Laser Ablation Cell Sorting in Scanning Cytometry," SPIE Photonics West, BIOS 2001 vol. 4260A, 11 pages, January 2001.
16. J. H. Price and D. A. Gough, "Nuclear Recognition in Images of Fluorescent Stained Cell Monolayers," International Society for Optical Engineering (SPIE), Applications of Digital Image Processing XIII, vol. 1349, pp. 294-300, Jul. 12, 1990.
17. J. H. Price, E. A. Hunter, and D. A. Gough. "Accuracy of Least Squares Designed Spatial FIR Filters for Segmentation of Images of Fluorescence Stained Cell Nuclei," *Cytometry* 25(4): 303-316, 1996. Annual Cytometry cover for 1998. Cover of UCSD Institute for Biomedical Engineering Brochure, 1998. Cover for ISAC Congress, 2000.
18. J H Price, D A Gough, "Method and Means of Least Squares Designed Filters for Image Segmentation in Scanning Cytometry," U.S. Pat. No. 5,790,692, 32 pages, Aug. 4, 1998.
19. Heynen S., Hunter E. A., Price J. H.: "Review of cell nuclear features for classification from fluorescence images," *Proceedings of SPIE* 3921: 54-64, 2000.
20. Mackin, R. W., Jr., Newton, L. M., Turner, J. N., Holmes, T. J., Roysam, B.: "Accuracy of nuclear classification in cervical smear images. Quantitative impact of computational deconvolution and 3-D feature computation," *Analytical and Quantitative Cytology and Histology* 20 (2): 77-91, 1998.
21. Mackin, R. W: "High-Speed Three-Dimensional Imaging, and Automated Three-Dimensional Image Analysis of Thick and Overlapped Clusters in Cytologic Preparations: Application to Pap Smears," PhD Thesis, Rensselaer Polytechnic Institute, 1995.
22. Heynen S., Price J. H.: "Evaluation of scanning cytometer fluorometry performance," *Proceedings of SPIE* 3604: 237-241, 1999.
23. Duda, R. O., Hart, P. E.: "Pattern classification and scene analysis," Wiley, New York, 1973.
24. Duda, R. O., Hart, P. E., Stork, D. G.: "Pattern Classification," Wiley, New York, 2000.
25. Hudson, D. L., Cohen, M. E.: "Neural networks and artificial intelligence for biomedical engineering," IEEE Press series in biomedical engineering, New York, 2000.
26. S Cha, P Lin, L Zhu, E L Botvinick, P C Sun, Y Fainman, "3D profilometry using a dynamically configurable confocal microscope," SPIE Proceedings, Photonics West. 3640: 246-253, 1999.
27. M Liang, R L Stehr, A W Krause, "Confocal pattern period in multiple-aperture confocal imaging systems with coherent illumination," Opt. Lett. 22:751-753, 1997.
28. Q S Hanley, P J Verveer, T M Jovin, "Optical sectioning fluorescence spectroscopy in a programmable array microscope," *Applied Spectroscopy* 52(6):783-789, 1998.
29. P J Verveer, Q S Hanley, P W Verbeek, L J Van Vliet and T M Jovin, "Theory of confocal fluorescence imaging in the programmable array microscope (PAM)," J. Microsc. 189(3):192-198, 1998.
30. E L Botvinick, S Cha, F F Li, D A Gough, Y Fainman, J H Price, "In-vivo confocal microscopy based on the Texas Instruments Digital Micromirror Device," *Proc. Of SPIE, Optical Diagnostics of Living Cells III*, San Jose, 3921: 12-19, 2000.
31. Q S Hanley, P J Verveer, M J Gemkow, D Arndt-Jovin, T M Jovin, "An optical sectioning programmable array microscope implemented with a digital micromirror device," Journal of Microscopy 196(3): 317-331, 1999.
32. S Heynen, D A Gough, J H Price, "Optically Stabilized Mercury Vapor Short Arc Lamp as UV-Light Source for Microscopy," SPIE Photonics West '97, vol. 2982: 430-434, Feb. 8-14, 1997.
33. J H Price, D A Gough, "Arc Lamp Stabilization and Intensity Control for Imaging Microscopy," U.S. Pat. No. 5,856,665, 31 pages, Jan. 5, 1999.
34. J H Price, "Autofocus vs. Voxel Projection for Vertical Tracking in Scanning Cytometry," SPIE Photonics West '97, vol. 2982: 485-489, Feb. 8-14, 1997.
35. Denk W, Strickler J H, Webb W W. Two-photon laser scanning fluorescence microscopy. Science 1990; 248:73-76.
36. Minsky M. "Microscopy apparatus," U.S. Pat. No. 3,013, 467; 1961.
37. Petran M, Hadravsky M, Egger M D, Galambos R. Tandem scanning reflected light microscope. Journal of the Optical Society of America. 1968; 58:661-664.
38. Suzuki T, Horikawa Y. Development of a real-time scanning laser microscope for biological use. Applied Optics 1986; 25:4115-4121.
39. Xiao G Q, Corle T R, Kino G S. Real-time confocal scanning optical microscope. Applied Physics Letters 1988; 53:716-718.
40. Tanaami T, Otsuki S, Tomosada N, Kosugi Y, Shimizu M, Ishida H. High-speed 1-frame/ms scanning confocal microscope with a microlens and Nipkow disks. Applied Optics 2002; 41 (22):4704-4708.
41. Liang M, Stehr R L, Krause A W. Confocal pattern period in multiple-aperture confocal imaging systems with coherent illumination. Optics Letters 1997; 22:751-753.
42. Hanley Q S, Verveer P J, Gemkow M J, Arndt-Jovin D, Jovin T M. An optical sectioning programmable array microscope implemented with a digital micromirror device. Journal of Microscopy 1999; 196(3):317-331.
43. Cha S D, Lin P C, Zhu L J, Sun P C, Fainman Y. Non-translational three-dimensional profilometry by chromatic confocal microscopy with dynamically configurable micromirror scanning. Applied Optics 2000; 39(16):2605-2613.
44. Botvinick E L, Li F, C ha S, Gough D A, Fainman Y, Price J H. In-vivo confocal microscopy based on the Texas Instruments digital micromirror device. Proceedings of the SPIE 2000; 3921:12-19.
45. Lane P M, Dlugan L P, Richards-Kortum R, MacAulay C E. Fiber-optic confocal microscopy using a spatial light modulator. Optics Letters 2000; 25(24):1780-1782.
46. Smith P J, Taylov C M, Shaw A J, McCabe E M. Programmable array microscopy with a ferroelectric liquid-crystal spatial light modulator. Applied Optics 2000; 39(16):2664-2669.
47. Buist A H, Müller M, Squier J, Brakenhoff G J. Real time two photon absorption microscopy using multipoint excitation. Journal of Microscopy. 1998; 192:217-226.
48. Fittinghoff D N, Wiseman P W, Squier J A. Widefield multiphoton and temporally decorrelated multifocal multiphoton microscopy. Optics Express 2000; 7:273-279.
49. Andresen V, Egner A, Hell S W. Time-multiplexed multifocal multiphoton microscope. Optics Letters 2001; 26:75-77.
50. Kononen J, Bubendorf L, Kallioniemi A, et at. Tissue microarrays for high-throughput molecular profiling of tumor specimens. Nat Med 1998; 4:844-847.
51. Skacel M. S., Skilton B., Pettay J. D., Tubbs R. R.: Tissue microarrays: a powerful tool for high-throughput analysis of clinical Specimens. Applied Immunohistochemistry & Molecular Morphology 2002; 10(1):1-6.
52. Irinopoulou T, Vassy J, Beil M, Nicolopoulou P, Encaoua D, Rigaut J P. Three-dimensional DNA image cytometry by confocal scanning laser microscopy in thick tissue blocks of prostatic lesions. Cytometry 1997; 27:99-105.
53. Rigaut J P, Vassy J, Herlin P, Duigou F, Masson E, Briane D, Foucrier J, Carvajal-Gonzalez S, Downs A M, Mandard A M. Three-Dimensional DNA image cytometry by confocal scanning laser microscopy in thick tissue blocks. Cytometry 1991; 12:511-524.
54. Irinopoulou T, Vassy J, Rigaut J P. Application of confocal scanning laser microscopy to 3-D DNA image cytometry of prostatic lesions. Analytical and Quantitative Cytology and Histology 1998; 20:351-357.
55. Teloka P, Baak J P A, van Ginkel H A H M, Belien J A M, van Diest P J, Broeckaert M A M, Schuurmans L T. Three-dimensional confocal laser scanning DNA ploidy cytometry in thick histological sections. Journal of Pathology 1996; 180:214-222.
56. Price J H, Hunter E A, Gough D A. Accuracy of least squares designed spatial FIR filters for segmentation of images of fluorescence stained cell nuclei. Cytometry 1996; 25:303-316.

57. Press W H, Teukolsky S A, Vetterling W T, Flannery B P. Numerical Recipes in C. $2^{nd}$ edition. Cambridge: Cambridge University Press; 1992. p 681-688.
58. Gropp W, Lusk E, Skjellum A. Using MPI: portable parallel programming with the message-passing interface. Cambridge: MIT Press; 1994. 307 p.
59. Gropp W, Lusk E, Thakur R. Using MPI-2: advanced features of the message-passing interface. Cambridge: MIT Press; 1999. 382 p.
60. The Message Passing Interface (MPI) standard, hftp://www-unix.mcs.anl.gov/mpi/.
61. Hamada S, Fujita S. DAPI staining improved for quantitative cytofluorometry. Histochemistry 1983; 79:219-226.
62. Inoue, S. and Spring, K. Video Microscopy (1997) Plenum Press.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for".

TABLE 1

Confusion Matrix for ANN

|  |  | Manual | | |
|---|---|---|---|---|
|  |  | M-Phase | G/S Phase | Other |
| ANN | M-Phase | 0.953 | 0.006 | 0.071 |
|  | G/S-Phase | 0.029 | 0.968 | 0.114 |
|  | Other | 0.018 | 0.026 | 0.814 |

TABLE 2

Confusion Matrix for Quatratic Deterministic Function

|  |  | Manual | | |
|---|---|---|---|---|
|  |  | G-Phase | S-Phase | M-Phase |
| QDF | G-Phase | 0.902 | 0.017 | 0.118 |
|  | S-Phase | 0.073 | 0.972 | 0.102 |
|  | M-Phase | 0.024 | 0.011 | 0.779 |

TABLE 3

3 × 3 Sharpening Filter $$\begin{bmatrix} -1 & -1 & -1 \\ -1 & 9 & -1 \\ -1 & -1 & -1 \end{bmatrix}$$

TABLE 4

3 × 3 Unsharp-Masking Filter $$\begin{bmatrix} -0.1667 & -0.1667 & -0.1667 \\ -0.1667 & 4.3333 & -0.1667 \\ -0.1667 & -0.1667 & -0.1667 \end{bmatrix}$$

TABLE 5

9 × 9 × 9 Nonlinear Least Squares FIR Filter
(Arranged below in spilt 9 row segments)

| | | | | |
|---|---|---|---|---|
| −3.062029e−001 | 1.713080e−002 | 2.597867e−002 | −5.835911e−002 | −4.175686e−002... |
| −1.016949e−002 | 8.197341e−002 | −8.182430e−003 | 1.960848e−002 | 3.837845e−002... |
| −8.680541e−003 | 5.024256e−002 | −2.759659e−003 | −1.481702e−002 | 1.152746e−002... |
| −2.807057e−002 | 2.779911e−002 | 4.407599e−003 | −2.507592e−002 | 1.616759e−002... |
| −9.579467e−003 | −5.367288e−003 | 3.240653e−002 | −6.131347e−002 | −1.820988e−002... |
| 1.460546e−002 | 2.786210e−002 | −8.654079e−003 | −7.880011e−002 | −5.355504e−002... |
| −1.326176e−002 | 5.099670e−002 | 2.483405e−002 | −2.526362e−003 | −1.557905e−003... |
| −2.324384e−002 | 7.128027e−002 | 3.590470e−002 | 3.235948e−002 | 2.056791e−002... |
| −2.307897e−001 | 6.196344e−003 | −3.541205e−002 | −3.825723e−002 | −1.642519e−002... |
| −2.542170e−002 | −3.801160e−002 | 1.106052e−002 | 2.431734e−001 | |
| 1.183914e−002 | 3.324781e−002 | 7.635876e−002 | −1.982201e−002 | |
| 1.524976e−002 | 1.191554e−002 | 4.311521e−002 | −4.630267e−002 | |
| 2.204827e−003 | 2.423944e−002 | 1.074946e−002 | −3.613940e−002 | |
| −1.059488e−002 | 3.544612e−003 | 5.131611e−002 | −3.761526e−002 | |
| 1.636971e−002 | 1.180144e−002 | 4.355877e−002 | −5.987504e−002 | |
| −1.932957e−002 | 3.263786e−002 | 4.732018e−002 | −2.672643e−002 | |
| 2.356361e−002 | 2.895187e−002 | 8.083912e−002 | −4.334129e−002 | |
| −3.736368e−002 | −1.244633e−002 | −2.578301e−002 | −2.336846e−001 | |

TABLE 5-continued

9 × 9 × 9 Nonlinear Least Squares FIR Filter
(Arranged below in split 9 row segments)

| | | | | |
|---|---|---|---|---|
| 1.051879e−001 | 8.810322e−002 | 4.203590e−002 | 5.156760e−002 | 1.207569e−002... |
| 1.151672e−001 | 4.915073e−002 | 6.819471e−003 | 3.579188e−003 | −9.059820e−003... |
| 3.313324e−002 | 3.424941e−003 | −3.430485e−002 | −7.300449e−002 | −3.103675e−002... |
| 1.388789e−002 | 1.548753e−002 | −2.911696e−002 | 4.283278e−003 | −4.339384e−002... |
| −3.143792e−002 | −5.073880e−002 | −3.972328e−002 | −7.630699e−002 | −1.916575e−001... |
| −5.733863e−003 | −8.215088e−002 | −9.627551e−002 | 1.227357e−001 | −1.386373e−001... |
| 1.821729e−002 | −1.902347e−002 | 1.225947e−001 | 1.116397e−001 | −8.087711e−002... |
| 1.086836e−001 | 6.612320e−002 | 1.054919e−002 | −1.440648e−002 | −3.100639e−002... |
| 8.383529e−002 | 8.323595e−002 | 1.704265e−002 | 5.604427e−002 | 3.358423e−002... |
| | 3.705968e−002 | 4.203995e−002 | 1.435513e−001 | 8.299524e−002 |
| | −2.279279e−002 | 8.869092e−005 | −3.405075e−003 | 1.440398e−002 |
| | −1.733749e−002 | −5.742340e−002 | −1.861076e−002 | 4.703500e−002 |
| | −4.670691e−002 | −4.126512e−002 | 1.224570e−002 | 3.661710e−002 |
| | −8.290119e−002 | −7.922882e−002 | 1.247419e−002 | 3.032255e−002 |
| | −1.268219e−001 | −1.080511e−001 | −3.146021e−002 | 7.449254e−002 |
| | −3.455047e−002 | −8.657534e−002 | −1.390595e−002 | 5.159468e−002 |
| | −2.596446e−002 | 4.830738e−003 | 5.275844e−002 | 1.488767e−001 |
| | 1.373530e−002 | 7.583588e−002 | 1.078589e−001 | 1.053085e−001 |
| −5.043806e−002 | −1.576954e−002 | −8.856140e−002 | −3.752988e−002 | −1.807111e−002... |
| −1.179775e−002 | −3.584659e−002 | −4.249378e−002 | 8.828282e−004 | 2.150376e−002... |
| −1.821483e−002 | −1.511241e−002 | −3.924713e−002 | −4.261477e−002 | 7.704313e−002... |
| −3.107928e−002 | 1.362605e−002 | 2.194436e−003 | 1.868291e−002 | 8.240625e−002... |
| −7.903361e−002 | 4.307423e−002 | 1.130572e−001 | 2.836669e−001 | 4.969743e−001... |
| −3.328353e−002 | −3.699494e−003 | 8.346824e−002 | 3.388642e−001 | 5.481404e−001... |
| −6.627608e−002 | −1.329235e−004 | −7.148556e−003 | −2.322956e−002 | 1.551249e−001... |
| −5.581533e−002 | −7.485159e−003 | −3.742376e−002 | −1.864919e−002 | 2.308151e−003... |
| −1.088050e−001 | −4.733852e−002 | −2.216533e−002 | −6.305803e−002 | −4.226969e−002... |
| | −4.023121e−002 | −8.454057e−002 | −3.952005e−003 | −1.224132e−001 |
| | 4.512914e−002 | −2.597505e−002 | −4.136569e−002 | −2.917491e−002 |
| | 3.059076e−003 | −2.693393e−002 | −6.674766e−002 | −5.746466e−002 |
| | 9.394337e−002 | 4.130620e−002 | 1.019254e−002 | 6.632588e−002 |
| | 2.045289e−001 | −5.316082e−003 | −2.733660e−003 | −3.578571e−002 |
| | 2.173162e−001 | 5.452092e−003 | 3.575961e−002 | −5.452018e−002 |
| | 3.856368e−002 | −4.991402e−002 | −1.014870e−001 | −6.467481e−002 |
| | 1.139579e−002 | −8.102296e−002 | −5.253173e−002 | −8.899792e−002 |
| | −7.180802e−002 | −7.631417e−002 | −5.102413e−002 | −1.297372e−001 |
| −8.387671e−002 | 3.159073e−002 | 1.401261e−003 | −1.400774e−002 | 2.906196e−002... |
| 3.213239e−002 | 5.102710e−002 | 3.956708e−002 | −2.181593e−003 | 2.432394e−002... |
| −2.077573e−002 | 2.186341e−003 | −2.839913e−002 | −9.498850e−002 | −8.168882e−002... |
| −3.766536e−002 | −2.637952e−004 | −9.127204e−002 | −1.444988e−001 | 1.894530e−002... |
| −2.677367e−002 | −5.351317e−002 | −1.468572e−001 | 2.101214e−002 | 4.314001e−001... |
| −2.518523e−002 | −4.905662e−002 | −1.588071e−001 | 1.451663e−001 | −1.457046e−001... |
| −3.581747e−002 | −6.960205e−002 | −9.854831e−002 | 1.533509e−001 | −2.037869e−001... |
| −2.731369e−003 | −3.126955e−002 | −6.623082e−002 | −8.027992e−002 | −6.728613e−002... |
| −8.518647e−002 | −1.016742e−003 | −7.007769e−002 | −8.201939e−002 | −5.428733e−002... |
| | −7.667730e−003 | −2.563160e−002 | 8.259110e−002 | −9.631600e−002 |
| | 1.944746e−002 | −2.323293e−002 | 5.866695e−002 | 4.633617e−002 |
| | −7.383950e−002 | −3.475649e−002 | 2.759331e−002 | −3.193085e−002 |
| | −1.673502e−001 | −1.076194e−001 | 1.316474e−002 | −6.289729e−003 |
| | −3.959275e−002 | −2.110190e−001 | 2.019755e−002 | −1.253021e−002 |
| | −1.432970e−002 | −1.724441e−001 | 1.243681e−002 | −3.668029e−002 |
| | −1.154208e−001 | −8.434319e−002 | −4.724362e−003 | −2.047214e−002 |
| | −3.931851e−003 | −1.055697e−002 | 3.892539e−002 | 5.122399e−003 |
| | −6.484163e−002 | −4.991134e−002 | 2.976685e−002 | −9.232853e−002 |
| −8.569531e−002 | 1.885248e−002 | −1.677670e−002 | −2.979985e−002 | 5.539392e−003... |
| −1.220045e−003 | 5.269211e−002 | 5.348551e−002 | 3.194875e−002 | 3.519823e−002... |
| −3.627102e−002 | 1.039374e−003 | 1.617988e−002 | 6.203608e−003 | −3.275461e−002... |
| 2.663181e−002 | 7.354350e−002 | −7.241380e−002 | −1.080573e−002 | 5.212558e−002... |
| 5.015715e−002 | 1.220796e−001 | −1.026251e−001 | 2.420887e−001 | 7.165397e−001... |
| 4.954287e−002 | 4.748686e−002 | −4.765224e−002 | 5.802324e−002 | 3.192875e−001... |
| 2.958767e−002 | 8.856974e−002 | 2.778767e−002 | −9.874666e−002 | −3.048727e−002... |
| 5.091693e−002 | 8.965653e−002 | 7.307344e−002 | 3.596812e−002 | 8.523270e−002... |
| 5.101182e−003 | 7.357116e−002 | 6.006179e−002 | 5.063623e−002 | 5.568215e−002... |
| | 3.395763e−003 | −1.410017e−002 | 6.184224e−002 | −1.232049e−001 |
| | 4.540176e−002 | 2.549863e−002 | 9.188373e−002 | 1.537951e−002 |
| | −1.508487e−002 | 3.017342e−002 | 4.964906e−002 | 7.941807e−003 |
| | −7.446266e−002 | −2.338909e−002 | 7.710830e−002 | 2.109952e−002 |
| | 1.104709e−001 | −9.043239e−002 | 7.310158e−002 | 1.747683e−002 |
| | 2.585491e−002 | 1.641197e−002 | 7.493415e−002 | 9.360582e−003 |
| | −5.686363e−003 | 4.026092e−002 | 1.102788e−001 | 2.564150e−002 |
| | 1.091583e−001 | 8.362534e−002 | 1.465175e−001 | 6.492631e−002 |
| | 7.485697e−002 | 2.023738e−002 | 6.839366e−002 | −8.322084e−002 |
| −8.113211e−002 | 8.501494e−002 | −7.961125e−003 | 2.162322e−002 | 2.618090e−002... |
| 2.977746e−002 | 8.202403e−002 | −7.489514e−003 | 2.048757e−002 | −4.251436e−003... |
| −5.628796e−003 | 4.536276e−002 | 2.110097e−002 | −3.661218e−002 | 8.867557e−003... |
| −6.814439e−003 | 6.685426e−002 | −6.068469e−003 | 1.900355e−002 | 2.199107e−001... |

TABLE 5-continued

9 × 9 × 9 Nonlinear Least Squares FIR Filter
(Arranged below in spilt 9 row segments)

| | | | | |
|---|---|---|---|---|
| −2.134098e−002 | 7.100439e−002 | −2.965331e−002 | 1.261756e−001 | 4.240374e−001... |
| −4.081222e−003 | 5.641698e−002 | 5.818457e−002 | 8.101399e−002 | 5.395809e−002... |
| 1.118098e−002 | 4.718586e−002 | 6.339249e−002 | 4.153578e−002 | 3.140652e−002... |
| 1.648862e−002 | 8.808470e−002 | 6.151982e−002 | 6.690781e−002 | 5.086030e−002... |
| −1.124750e−001 | 3.521733e−002 | 2.287904e−002 | 2.399322e−002 | 5.308196e−002... |
| | 5.397899e−003 | −2.395100e−002 | 7.342080e−002 | −1.238183e−001 |
| | 2.599022e−002 | 6.600723e−003 | 6.761404e−002 | 6.078978e−002 |
| | −5.910352e−002 | −1.147655e−002 | 1.863215e−002 | −1.494345e−002 |
| | 1.041655e−001 | −8.537366e−002 | −7.801892e−003 | 1.967932e−003 |
| | 1.405227e−001 | −3.566265e−002 | 1.953541e−002 | 5.262511e−003 |
| | −3.189713e−002 | −1.547452e−002 | 9.557411e−003 | 3.204922e−002 |
| | −3.714700e−002 | −3.643742e−002 | 2.208842e−002 | 2.590902e−002 |
| | 5.057505e−002 | 1.328991e−002 | 8.465383e−002 | 4.693796e−002 |
| | 1.022614e−002 | 1.855187e−002 | 7.760667e−002 | −2.806166e−002 |
| −1.095870e−001 | 4.731039e−003 | −4.684576e−002 | −2.906020e−002 | −3.194049e−002... |
| −5.258163e−004 | −7.392173e−004 | −5.060920e−002 | −9.295444e−003 | −1.666575e−002... |
| −5.242114e−002 | −3.061689e−002 | −3.359274e−002 | −7.349113e−002 | −6.827904e−002... |
| −4.654102e−002 | 2.333181e−002 | −4.242286e−002 | −2.085043e−002 | 2.428300e−001... |
| −3.204503e−002 | 2.472466e−002 | −4.769153e−002 | 6.366719e−002 | 3.427251e−001... |
| −3.776116e−002 | 1.711716e−002 | −1.048407e−002 | −2.214921e−002 | 4.571425e−002... |
| −4.060864e−002 | 2.761823e−002 | −1.203550e−002 | 1.913514e−003 | −3.429225e−002... |
| −2.595880e−002 | 3.122497e−002 | −2.266706e−002 | 8.668885e−003 | 2.220909e−002... |
| −1.921386e−001 | 9.609680e−003 | −3.618693e−002 | −3.271029e−002 | −3.541981e−002... |
| | −3.489528e−002 | −3.523861e−002 | 3.501873e−002 | −1.467880e−001 |
| | −2.155717e−002 | −6.461816e−002 | 2.831562e−002 | −4.715854e−003 |
| | −4.562497e−003 | −5.966000e−002 | −1.233551e−002 | −5.767091e−002 |
| | 1.293980e−001 | 3.049272e−004 | −2.611339e−002 | −2.187913e−002 |
| | 1.992084e−001 | −6.729344e−004 | −1.103520e−002 | −2.225822e−002 |
| | 3.871039e−002 | −2.577576e−002 | 2.843974e−002 | −7.683540e−002 |
| | −3.276200e−002 | −2.559543e−002 | −5.579257e−002 | −7.974239e−002 |
| | −3.780277e−002 | −5.006012e−002 | 1.376533e−003 | −4.895961e−002 |
| | −5.369900e−002 | −3.897659e−002 | −2.214771e−002 | −1.705062e−001 |
| 2.750314e−002 | 8.461956e−002 | 3.704538e−003 | 2.705722e−003 | −2.733694e−003... |
| 1.365584e−001 | 1.056584e−001 | 1.052617e−004 | 7.511364e−003 | 9.219435e−003... |
| 5.652872e−002 | 6.365564e−003 | −4.944519e−002 | −3.808802e−002 | 6.366892e−004... |
| 1.400308e−004 | 2.725364e−002 | −4.192823e−002 | −5.163159e−002 | 1.753534e−001... |
| −5.618740e−003 | 9.216977e−003 | −1.021168e−001 | −E.236979e−002 | 1.373361e−001... |
| −8.711238e−003 | −5.877331e−003 | −5.388367e−002 | −4.656988e−002 | −3.270329e−002... |
| 6.725459e−002 | 1.574068e−002 | −1.069586e−002 | 4.706069e−003 | −2.565487e−002... |
| 1.192337e−001 | 1.074489e−001 | −1.709446e−002 | −3.988571e−002 | 7.982592e−003... |
| 6.164884e−003 | 1.240274e−001 | 4.630913e−002 | 6.648286e−002 | 2.357046e−003... |
| | 3.338853e−003 | 6.424997e−002 | 1.480025e−001 | −6.541092e−002 |
| | −1.459218e−002 | 6.924991e−003 | 1.368665e−001 | 1.004381e−001 |
| | −3.648729e−002 | −7.397051e−002 | 4.678517e−003 | 6.278002e−002 |
| | 1.053770e−001 | −1.000103e−001 | −3.044222e−002 | 5.898667e−004 |
| | 9.232106e−002 | −2.997570e−003 | 2.183847e−002 | 2.270738e−002 |
| | −1.744081e−002 | −1.362095e−002 | 4.263103e−002 | 4.592729e−002 |
| | −6.624193e−002 | −2.740071e−002 | 4.187603e−002 | 6.665460e−002 |
| | −1.500874e−002 | 2.187869e−002 | 1.484740e−001 | 1.067082e−001 |
| | 2.242132e−002 | 8.987668e−002 | 1.466278e−001 | 6.529785e−002 |
| −4.531853e−001 | −3.492841e−002 | −7.180204e−002 | −1.228832e−001 | −8.667742e−002... |
| −6.939659e−002 | 1.418218e−001 | 1.025540e−001 | 6.272756e−002 | 5.245060e−002... |
| −6.055093e−002 | 9.237222e−002 | 2.345693e−002 | 2.782038e−002 | 6.285770e−002... |
| −5.267095e−002 | 7.585954e−002 | 1.889956e−003 | −3.542653e−002 | 6.328024e−002... |
| −1.010957e−001 | 3.689981e−002 | −1.986134e−002 | 6.705403e−002 | −4.943908e−003... |
| −8.945438e−002 | 5.367993e−002 | 1.143971e−002 | 9.559330e−003 | −3.642463e−002... |
| −7.215440e−002 | 9.141000e−002 | 1.562556e−002 | 3.653468e−002 | −3.167553e−003... |
| −2.664319e−002 | 1.762187e−001 | 4.384476e−002 | 2.363957e−002 | 4.429676e−002... |
| −4.425591e−001 | 1.063365e−002 | −4.935303e−002 | −7.706291e−002 | −7.510871e−002... |
| | −1.578058e−001 | −7.914372e−002 | −1.284970e−001 | −4.892146e−001 |
| | 4.372354e−002 | 1.117198e−001 | 1.919738e−001 | −9.822817e−002 |
| | 3.934281e−002 | 8.453830e−002 | 1.217507e−001 | −1.146394e−001 |
| | 8.196209e−002 | 1.451575e−002 | 4.713271e−002 | −1.097693e−001 |
| | −6.072183e−004 | 1.590508e−002 | 8.029268e−002 | −1.383875e−001 |
| | −5.072229e−002 | 1.796757e−002 | 6.569247e−002 | −1.280614e−001 |
| | −6.992426e−003 | 4.517332e−002 | 1.015840e−001 | −9.209926e−002 |
| | −6.737961e−004 | 8.778365e−002 | 1.445490e−001 | 1.483138e−001 |
| | −8.654095e−002 | −5.568483e−002 | −1.313605e−001 | −2.404858e−001 |

What is claimed is:

1. A method of distinguishing a 3D object from a background, the method comprising:
retrieving an acquired 3D image of a sample volume;
executing, on a computing device, programming for carrying out the steps comprising:
enhancing object-to-background contrast ratios for said 3D image;
thresholding said 3D image to delineate object boundaries; and
generating information about said delineated 3D objects;
wherein said thresholding is performed in response to analyzing confocal volumes.

2. A method as recited in claim 1, wherein said generating information comprises rendering surfaces of objects based on said object boundaries.

3. A method as recited in claim 1, wherein said generating information comprises generating quantitative information about objects based on said object boundaries.

4. A method as recited in claim 1, wherein said thresholding is performed by selecting a minimum after the largest background intensity peak.

5. A method as recited in claim 4, wherein said minimum comprises a first minimum.

6. A method as recited in claim 1, wherein said enhancing object-to-background contrast is performed utilizing image filters.

7. A method as recited in claim 6, wherein said image filters comprise finite impulse response (FIR) filters.

8. A method as recited in claim 7, wherein said image filters are created based upon ideal image sections collected from a 3D object.

9. A method of distinguishing a 3D object from a background, comprising:
retrieving acquired 3D images of a sample volume; executing, on a computing device, programming for carrying out the steps comprising:
enhancing object-to-background contrast ratios for said 3D image by applying least squares finite impulse response (FIR) filters;
thresholding said 3D image in response to confocal volumes to delineate object boundaries; and
generating information about said delineated 3D objects.

* * * * *